(12) United States Patent
Someya et al.

(10) Patent No.: US 9,334,352 B2
(45) Date of Patent: May 10, 2016

(54) SEMI-CURED PRODUCT, CURED PRODUCT AND METHOD FOR PRODUCING THESE, OPTICAL COMPONENT, CURABLE RESIN COMPOSITION, AND COMPOUND

(71) Applicant: FUJIFILM Corporation, Tokyo (JP)

(72) Inventors: Ayumi Someya, Ashigarakami-gun (JP); Masataka Yoshizawa, Ashigarakami-gun (JP); Tatsuhiko Obayashi, Ashigarakami-gun (JP); Hiroyuki Naitou, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 14/668,474

(22) Filed: Mar. 25, 2015

(65) Prior Publication Data
US 2015/0197592 A1    Jul. 16, 2015

Related U.S. Application Data

(63) Continuation of application No. PCT/JP2013/075283, filed on Sep. 19, 2013.

(30) Foreign Application Priority Data

Sep. 26, 2012 (JP) ................................. 2012-211856
Jul. 1, 2013 (JP) ................................. 2013-138415

(51) Int. Cl.
| | | |
|---|---|---|
| C08F 2/46 | (2006.01) | |
| C08G 61/04 | (2006.01) | |
| C08F 222/20 | (2006.01) | |
| C07C 69/54 | (2006.01) | |
| C08F 220/30 | (2006.01) | |

(Continued)

(52) U.S. Cl.
CPC .............. *C08F 222/20* (2013.01); *C07C 13/66* (2013.01); *C07C 69/54* (2013.01); *C07C 69/602* (2013.01); *C07C 233/20* (2013.01); *C07C 323/19* (2013.01); *C07C 323/66* (2013.01); *C07D 209/58* (2013.01); *C07D 263/52* (2013.01); *C07D 277/60* (2013.01); *C07D 307/77* (2013.01); *C07D 311/96* (2013.01); *C07D 333/78* (2013.01); *C08F 12/26* (2013.01); *C08F 12/32* (2013.01); *C08F 12/34* (2013.01); *C08F 212/32* (2013.01); *C08F 212/34* (2013.01); *C08F 220/30* (2013.01); *C08F 222/1006* (2013.01); *C09D 125/16* (2013.01); *G02B 1/041* (2013.01); *C07C 2103/40* (2013.01); *C07C 2103/52* (2013.01)

(58) Field of Classification Search
CPC ............... C08F 222/20; C08F 212/34; C08F 222/1006; C08F 220/30; C08F 12/26; C08F 12/34; C08F 2222/205; C08F 12/32; G02B 1/041; C07D 333/78; C07D 277/60; C07D 307/77; C07D 311/96; C07D 263/52; C07D 209/58; C07C 69/602; C07C 13/66; C07C 323/66; C07C 2103/40; C07C 69/54; C07C 323/19; C07C 233/20; C07C 2103/52; C09D 125/16; C08L 45/20
USPC .................. 522/33, 6, 71, 189, 184, 1; 520/1
See application file for complete search history.

(56) References Cited

U.S. PATENT DOCUMENTS

| | | | | |
|---|---|---|---|---|
| 5,109,097 A | * | 4/1992 | Klun et al. ...................... | 528/75 |
| 8,952,079 B2 | | 2/2015 | Morooka et al. | |

(Continued)

FOREIGN PATENT DOCUMENTS

| | | | |
|---|---|---|---|
| JP | 2001-122828 | * | 5/2001 |
| JP | 2001-172339 | * | 6/2001 |

(Continued)

OTHER PUBLICATIONS

Fujishiro et al, Oct. 5, 2000, WO 20000-058788 Machine Translation.*

(Continued)

*Primary Examiner* — Ling Choi
*Assistant Examiner* — Jessica E Whiteley
(74) *Attorney, Agent, or Firm* — Sughrue Mion, PLLC

(57) ABSTRACT

A curable resin composition containing a compound of formula (1), a compound of formula (2) and a thermal- or photoradical polymerization initiator is capable of producing a cured product having a low Abbe's number and capable of realizing burr reduction in molding the composition. $Ar^1$ to $Ar^4$ represent aryl or heteroaryl, at least one of $Ar^1$ to $Ar^4$ is aromatic condensed ring, and two or more of $Ar^1$ to $Ar^4$ have a polymerizable group, and at least one of $R^{21}$ to $R^{26}$ forms a ring, or at least two bond to each other to form a ring:

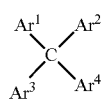

(1)

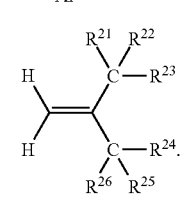

(2)

14 Claims, 5 Drawing Sheets

(51) Int. Cl.

| | |
|---|---|
| *G02B 1/04* | (2006.01) |
| *C08F 222/10* | (2006.01) |
| *C07C 13/66* | (2006.01) |
| *C07D 311/96* | (2006.01) |
| *C07D 333/78* | (2006.01) |
| *C07D 263/52* | (2006.01) |
| *C07D 277/60* | (2006.01) |
| *C07D 209/58* | (2006.01) |
| *C07D 307/77* | (2006.01) |
| *C07C 323/19* | (2006.01) |
| *C07C 323/66* | (2006.01) |
| *C07C 233/20* | (2006.01) |
| *C07C 69/602* | (2006.01) |
| *C08F 212/34* | (2006.01) |
| *C08F 12/26* | (2006.01) |
| *C08F 12/32* | (2006.01) |
| *C08F 12/34* | (2006.01) |
| *C08F 212/32* | (2006.01) |
| *C09D 125/16* | (2006.01) |

(56) References Cited

U.S. PATENT DOCUMENTS

| | | | |
|---|---|---|---|
| 2005/0014088 A1* | 1/2005 | Nakamura et al. | 430/270.1 |
| 2010/0068537 A1* | 3/2010 | Kano et al. | 428/446 |
| 2012/0196949 A1* | 8/2012 | Heo et al. | 522/63 |
| 2013/0237630 A1 | 9/2013 | Morooka et al. | |

FOREIGN PATENT DOCUMENTS

| | | | |
|---|---|---|---|
| JP | 2004-196965 | * | 7/2004 |
| JP | 2009-173648 A | | 8/2009 |
| JP | 2011-068624 | * | 4/2011 |
| JP | 2011-068624 A | | 4/2011 |
| JP | 2011-126991 | * | 6/2011 |
| JP | 2012-082386 A | | 4/2012 |
| JP | 4908781 B2 | | 4/2012 |
| JP | 2012-107191 A | | 6/2012 |
| JP | 2012-206968 | * | 10/2012 |
| WO | 00-58788 | * | 10/2000 |
| WO | 2012/057071 A1 | | 5/2012 |
| WO | 2012-255914 | * | 12/2012 |

OTHER PUBLICATIONS

Tanitsu et al, May 8, 2001, JP 2001-122828 Machine Translation.*
Takatori et al, Jun. 26, 2001, JP 2001-172339 Machine Translation.*
Matsunami et al, Jul. 15, 2004, JP 2004-196965 Machine Translation.*
Miyauchi et al, Apr. 7, 2011, JP 2011-068624 Machine Translation.*
Aoki et al, Jun. 30, 2011, JP 2011-126991 Machine Translation.*
Fukunishi et al, Oct. 25, 2012, JP 2012-206968 Machine Translation.*
Kawashima et al, Dec. 27, 2012, JP 2012-255914 Machine Translation.*
International Search Report of PCT/JP2013/075283 dated Dec. 17, 2013.
Office Action dated Oct. 6, 2015 from the Japanese Patent Office in counterpart Japanese Application No. 2013-138415.
International Preliminary Report on Patentability dated Apr. 9, 2015, issued by the International Bureau in corresponding PCT International Application No. PCT/JP2013/075283.
Office Action dated Dec. 10, 2015 from the State Intellectual Property Office of the P.R.C. in counterpart Chinese Application No. 201380050345.1.

* cited by examiner

SEMI-CURED PRODUCT, CURED PRODUCT AND METHOD FOR PRODUCING THESE, OPTICAL COMPONENT, CURABLE RESIN COMPOSITION, AND COMPOUND

CROSS-REFERENCE TO RELATED APPLICATIONS

This application is a Continuation of PCT International Application No. PCT/JP2013/075283, filed on Sep. 19, 2013, which claims priority under 35 U.S.C. Section 119 (a) to Japanese Patent Application No. 2012-211856 filed on Sep. 26, 2012 and Japanese Patent Application No. 2013-138415 filed on Jul. 1, 2013. Each of the above applications is hereby expressly incorporated by reference, in its entirety, into the present application.

BACKGROUND OF THE INVENTION

1. Field of the Invention

The present invention relates to a semi-cured product, a cured product and a method for producing these, and to an optical component, a curable resin composition and a compound.

2. Background Art

An imaging module is used in cameras, video cameras, camera cell-phones, TV telephones, camera intercoms, etc. Recently, the optical system for use in such image modules is especially required to be downsized. Downsizing optical systems may bring about a serious problem of chromatic aberration in those optical systems.

Glass heretofore used as a material in optical systems can realize various necessary optical characteristics and is excellent in environmental tolerance, but has a problem in that the workability thereof is poor.

As opposed to this, a resin cured product that is inexpensive as compared with a glass material and is excellent in workability has become used in optical components. There is known a method of adding various additives to a curable resin composition to change the properties of the cured products, and recently, it has become known to make a material composition have an increased refractive index and a reduced Abbe's number and therefore to make the composition highly dispersible for chromatic aberration correction.

Here, as a monomer for use in a curable resin composition for producing optical components, a compound having a fluorene skeleton has been generally used for the reason of high refractivity thereof.

For example, Patent Reference 1 describes a (meth)acrylate compound having a 9,9-bisphenylfluorene skeleton, saying that the compound can provide a high-refractivity composition usable as an optical material.

Patent Reference 2 describes a method for producing alcohols, epoxies and (meth)acrylates having a fluorene skeleton, saying that the method can provide compounds that are colored very little. Patent Reference 2 discloses (meth)acrylates having a 9,9-bisphenylfluorene skeleton, and (meth)acrylates having a 9,9-bisnaphthylfluorene skeleton.

However, Patent Reference 1 and Patent Reference 2 do not describe a method of reducing the Abbe's number of a cured product when a fluorene skeleton-having monomer.

On the other hand, Patent Reference 3 describes a technique of burr reduction in molding to increase the good-quality ratio of molded products by semi-curing a composition containing an alicyclic structure-having (meth)acrylate monomer and a non-conjugated vinylidene group-containing compound. However, Patent Reference 3 has no description of suggesting use of a monomer having an aromatic ring structure. In addition, Patent Reference 3 does not describe a method of reducing the Abbe's number of cured products.

On the other hand, Patent Reference 4 describes a technique of providing an optical material having a small Abbe's number by using a polyester polymer that contains, as one copolymerization component therein, an alcohol having a fluorene skeleton.

CITATION LIST

Patent References

Patent Reference 1: JP-A 2012-82386
Patent Reference 2: JP-A 2011-68624
Patent Reference 3: JP-A 2012-107191
Patent Reference 4: Japanese Patent 4908781

SUMMARY OF INVENTION

The present inventors have found that, when a lens is produced using a composition that contains 9,9-bis[6-(2-hydroxyethoxy)-2-naphthyl]fluorene diacrylate described in Example 28 in Patent Reference 2, there occurs a problem of burr'formation in molding. Further, the inventors tried Example 1 in Patent Reference 3 in which a composition containing an alicyclic structure-having (meth)acrylate monomer and a non-conjugated vinylidene group-containing compound is semi-cured, and have known that the resultant product has an extremely high-Abbe's number and therefore it is desired to further reduce the Abbe's number of the product.

The present invention is to solve the above-mentioned problems. Specifically, the technical problem with the present invention is to provide a curable resin composition capable of producing a cured product having a low Abbe's number and capable of realizing burr reduction in molding the composition.

The present inventors have assiduously studied and, as a result, have found that, when an lens is produced using a composition containing a 9,9-bisphenylfluorene skeleton-containing monomer of the compound (19) in Patent Reference 1 and containing, as added thereto, a non-conjugated vinylidene group-containing compound described in Patent Reference 3, then the Abbe's number of the lens is still high and therefore it is desired to further reduce the Abbe's number of the product.

Given the situation, the inventors have known that a curable resin composition that contains a monomer having a specific structure of having at least one aromatic condensed ring skeleton and having a number of polymerizable groups, and a non-conjugated vinylidene group-containing compound having a specific structure can solve the problem of burr formation in molding and can produce a cured product having a low Abbe's number. Specifically, the present inventors have found that the above-mentioned problems can be solved by the following constitution and have completed the present invention.

[1] A curable resin composition containing a condensed ring-containing compound represented by the following general formula (1), a non-conjugated vinylidene group-containing compound represented by the following general formula (2), and at least one of a thermal- or photo-radical polymerization initiator:

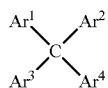

General Formula (1)

In the general formula (1), $Ar^1$ to $Ar^4$ each independently represent an aryl group optionally having a substituent or a heteroaryl group optionally having a substituent, at least one of $Ar^1$ to $Ar^4$ is an aromatic condensed ring group optionally having a substituent, and two or more of $Ar^1$ to $Ar^4$ contain a substituent having a polymerizable group. $Ar^1$ to $Ar^4$ may bond to each other.

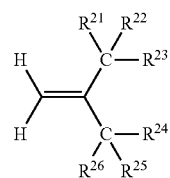

General Formula (2)

In the general formula (2), $R^{21}$ to $R^{26}$ each independently represent a substituent, at least one of $R^{21}$ to $R^{26}$ forms a ring, or at least two bond to each other to form a ring.

[2] The curable resin composition according to [1], wherein the condensed ring-containing compound represented by the general formula (1) is preferably represented by the following general formula (3):

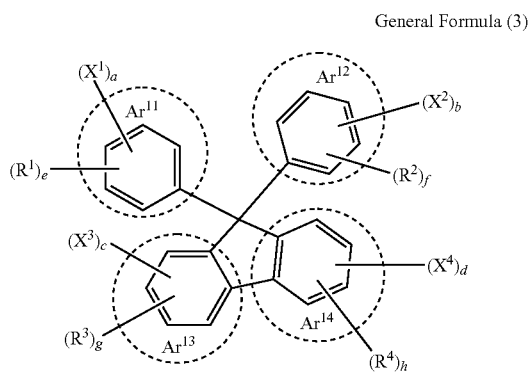

General Formula (3)

In the general formula (3), $Ar^{11}$ to $Ar^{14}$ each independently represent an aryl or heteroaryl group containing the benzene ring surrounded by the broken line, and at least one of $Ar^{11}$ to $Ar^{14}$ is an aromatic condensed ring group containing the benzene ring surrounded by the broken line as one condensed ring therein. $X^1$ to $X^4$ each independently represent a substituent having a polymerizable group, and the carbon atom in the substituent may be substituted with a hetero atom. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, and the upper limit of e, f, g and h each is a value calculated by subtracting a, b, c or d from the possible maximum number of the substituents that $Ar^{11}$ to $Ar^{14}$ each may have. However, in a case where $Ar^{11}$ to $Ar^{14}$ each are an aromatic condensed ring group containing the benzene ring surrounded by the broken line as one condensed ring therein, $X^1$ to $X^4$ and $R^1$ to $R^4$ each may independently substitute on the benzene ring surrounded by the broken line or on any other ring than the benzene ring surrounded by the broken line.

[3] The curable resin composition according to [1] or [2], wherein the condensed ring-containing compound represented by the general formula (1) is preferably represented by the following general formula (4):

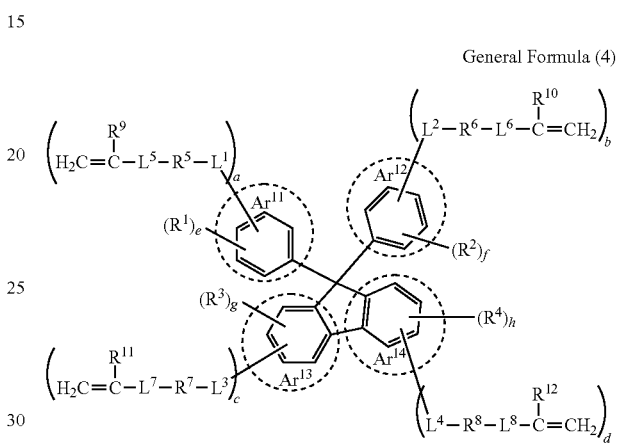

General Formula (4)

In the general formula (4), $Ar^{11}$ to $Ar^{14}$ each independently represent an aryl or heteroaryl group containing the benzene ring surrounded by the broken line, and at least one of $Ar^{11}$ to $Ar^{14}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, and the upper limit of e, f, g and h each is a value calculated by subtracting a, b, c or d from the possible maximum number of the substituents that $Ar^{11}$ to $Ar^{14}$ each may have. However, in a case where $Ar^{11}$ to $Ar^{14}$ each are an aromatic condensed ring group containing the benzene ring surrounded by the broken line as one condensed ring therein, the structures surrounded by a's, b's, c's or d's parentheses as well as $R^1$ to $R^4$ each may independently substitute on the benzene ring surrounded by the broken line or on any other ring than the benzene ring surrounded by the broken line.

[4] The curable resin composition according to any one of [1] to [3]; wherein the condensed ring-containing compound represented by the general formula (1) is preferably represented by the following general formula (5):

General Formula (5)

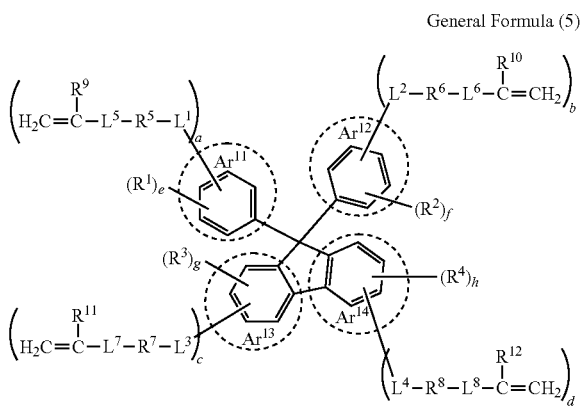

In the general formula (5), Ar and $Ar^{12}$ each independently represent an aryl or heteroaryl group containing the benzene ring surrounded by the broken line, $Ar^{13}$ and $Ar^{14}$ each independently represent an aryl or heteroaryl group containing the benzene ring surrounded by the broken line, and at least one of $Ar^{13}$ and $Ar^{14}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, the upper limit of e and f each is 5-a and 5-b, respectively, the upper limit of g and h each is a value calculated by subtracting c or d from the possible maximum number of the substituents that $Ar^{13}$ and $Ar^{14}$ each may have. However, in a case where $Ar^{13}$ and $Ar^{14}$ each are an aromatic condensed ring group containing the benzene ring surrounded by the broken line as one condensed ring therein, the structures surrounded by c's or d's parentheses as well as $R^3$ and $R^4$ each may independently substitute on the benzene ring surrounded by the broken line or on any other ring than the benzene ring surrounded by the broken line.

[5] The curable resin composition according to [3] or [4], wherein $Ar^{13}$ and $Ar^{14}$ in the condensed ring-containing compound represented by the general formula (4) or (5) each are preferably an aromatic hydrocarbon group containing the benzene' ring surrounded by the broken line and having from 6 to 10 carbon atoms.

[6] The curable resin composition according to any one of [1] to [5], wherein the condensed ring-containing compound represented by the general formula (1) is preferably represented by any of the following general formulae (6) to (9)

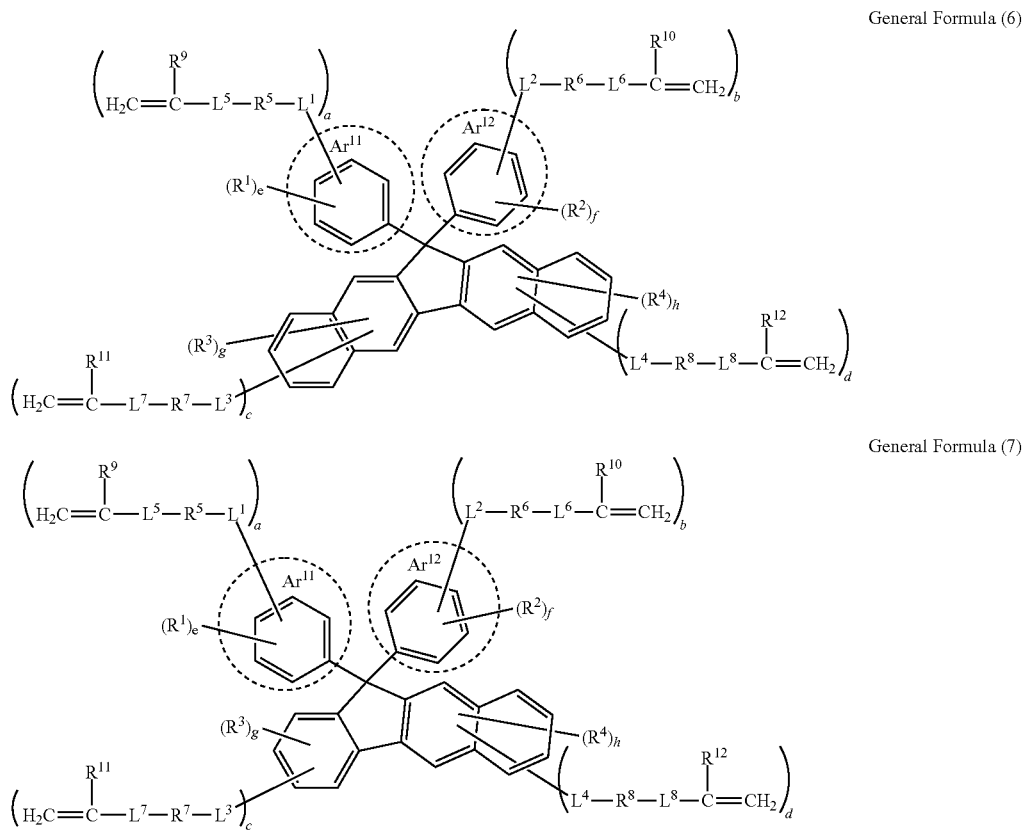

General Formula (6)

General Formula (7)

General Formula (8)

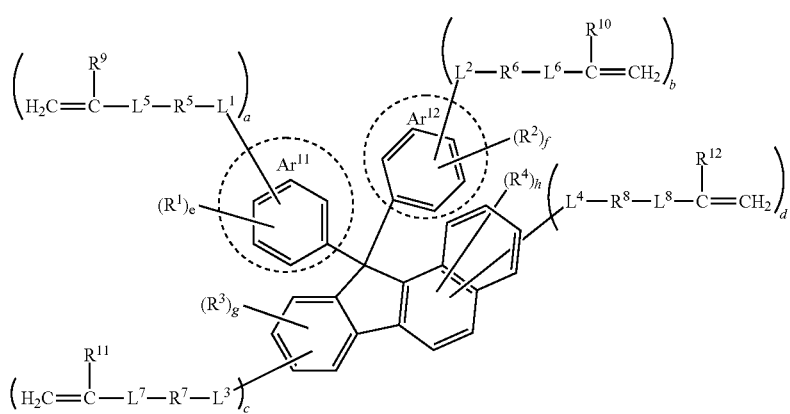

General Formula (9)

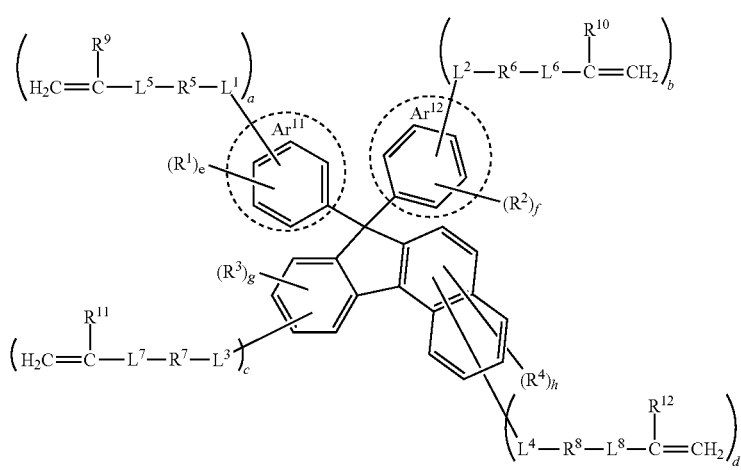

In the general formulae (6) to (9), $Ar^{11}$ and $Ar^{12}$ each independently represent an aryl or heteroaryl group containing the benzene ring surrounded by the broken line, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more.

However, in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

[7] The curable resin composition according to [6], wherein the condensed ring-containing compound represented by the general formulae (6) to (9) is preferably represented by any of the following formulae (6A), (7A), (8A), (9A), (6B), (7B), (8B) and (9B)

General Formula (6A)

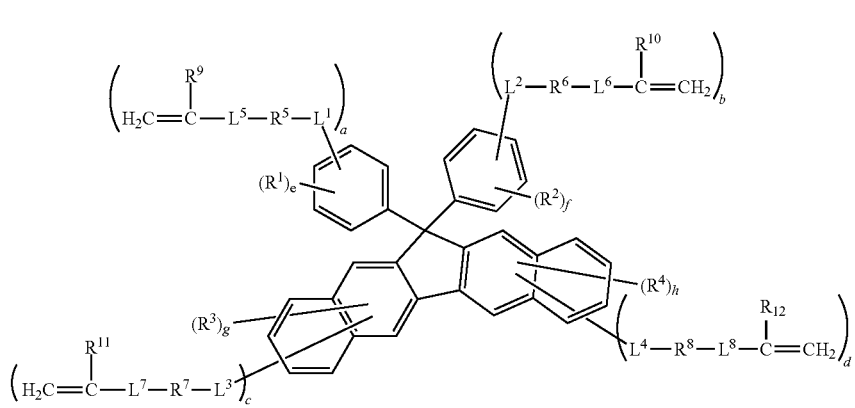

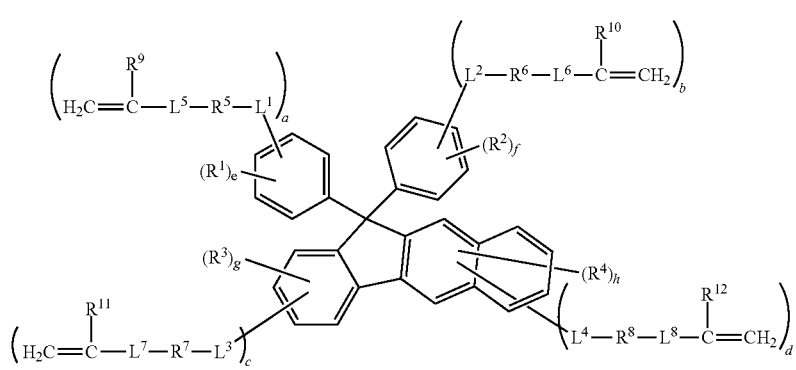

General Formula (7A)

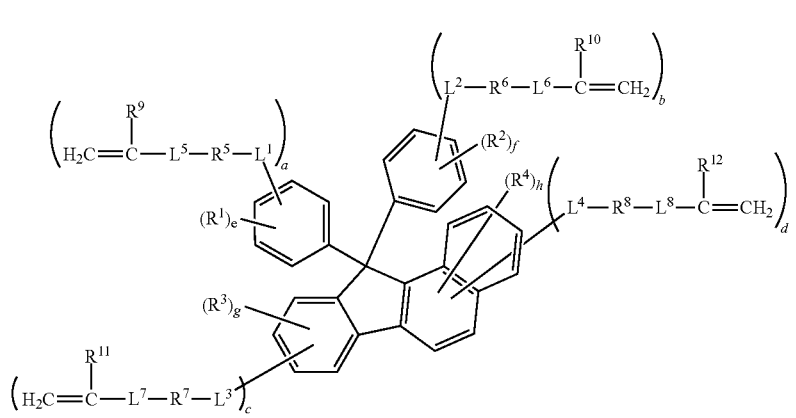

General Formula (8A)

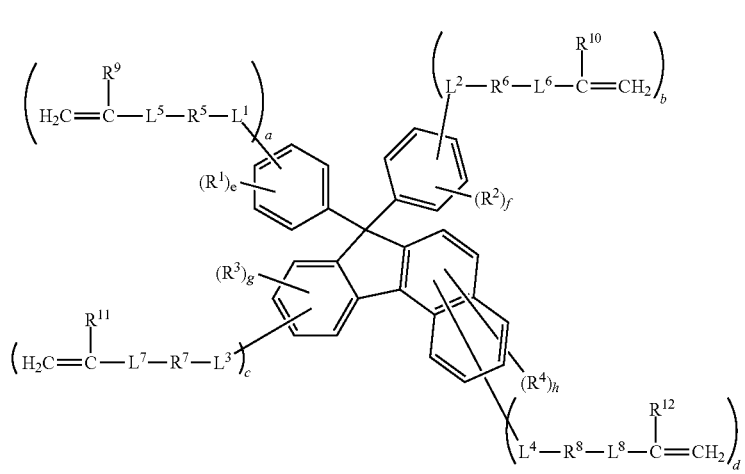

General Formula (9A)

In the general formulae (6A), (7A), (8A) and (9A), $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, and e, f, g and h each independently indicate an integer of 0 or more.

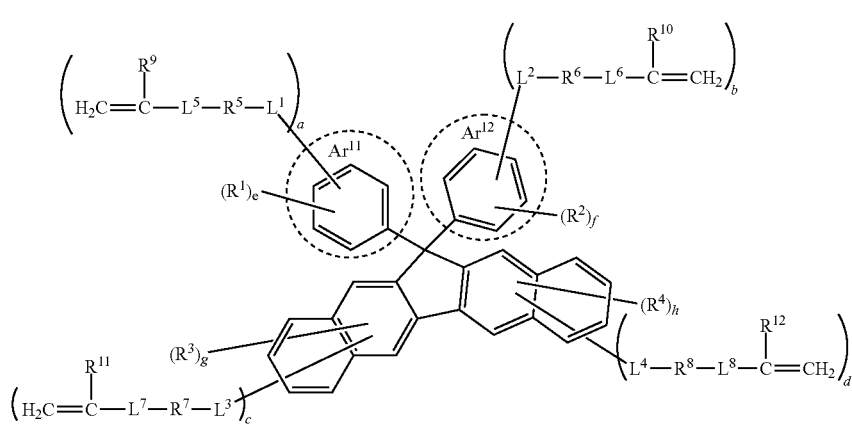
General Formula (6B)
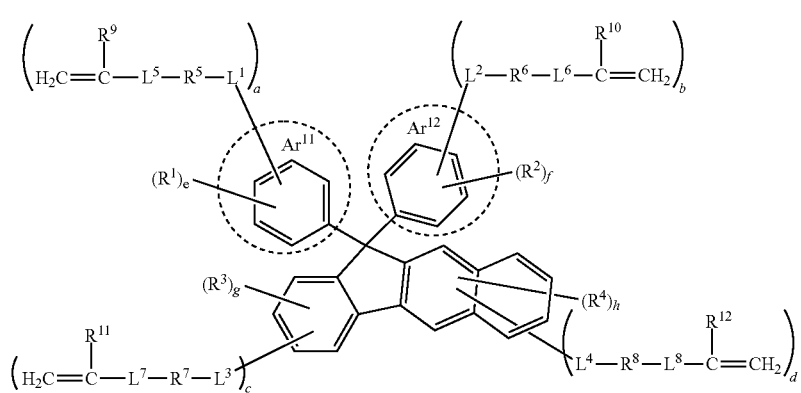
General Formula (7B)
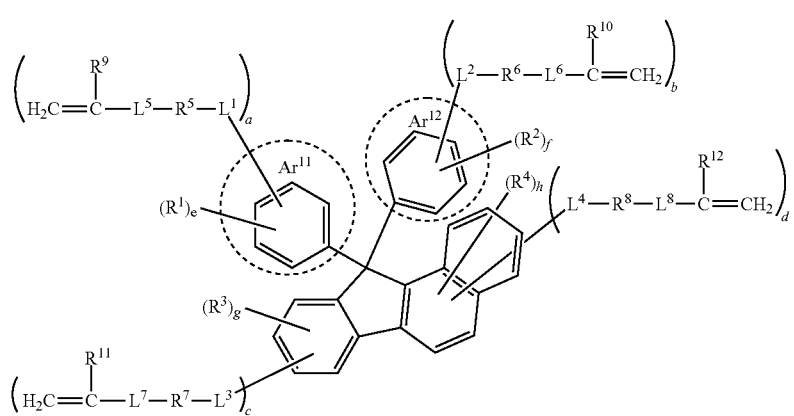
General Formula (8B)
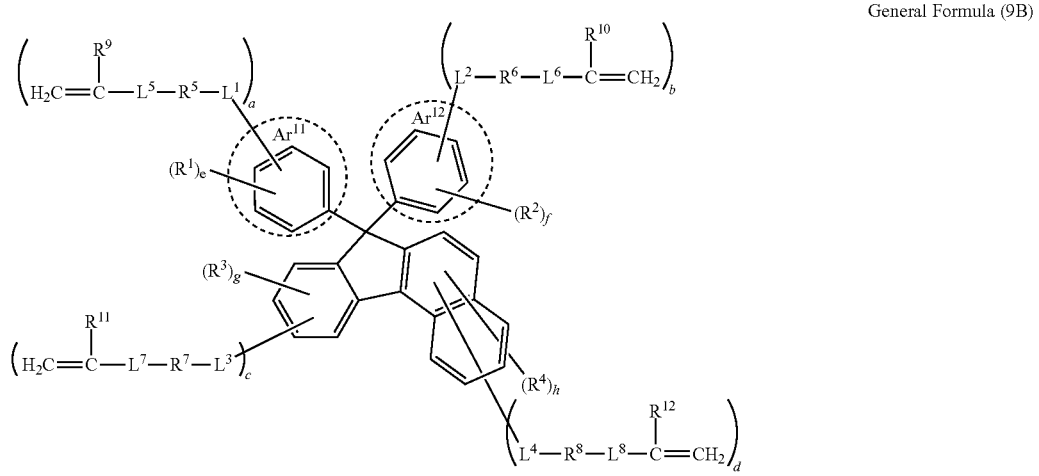
General Formula (9B)

In the general formulae (6B), (7B), (8B) and (9B), $Ar^{11}$ and $Ar^{12}$ each independently represent an aryl or heteroaryl group containing the benzene ring surrounded by the broken line, and at least one of $Ar^{11}$ and $Ar^{12}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more. However, in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

[8] The curable resin composition according to any one of [3] to [7], wherein in the condensed ring-containing compound represented by any of the general formulae (4) to (9), (6A), (7A), (8A), (9A), (6B), (7B), (8B) and (9B), preferably, $L^1$ to $L^4$ each are independently an oxygen atom or a sulfur atom, $L^5$ to $L^8$ each are independently an ester bond, a thioester bond or an amide bond, and $R^5$ to $R^8$ each are independently an alkylene group optionally having a substituent.

[9] The curable resin composition according to any one of [3] to [8], wherein in the condensed ring-containing compound represented by any of the general formulae (4) to (9), (6A), (7A), (8A), (9A), (6B), (7B), (8B) and (9B), preferably, c and d are both 0.

[10] The curable resin composition according to any one of [1] to [9], wherein the condensed ring-containing compound represented by the general formula (1) is preferably any of the following Xa-4 to Xa-15.

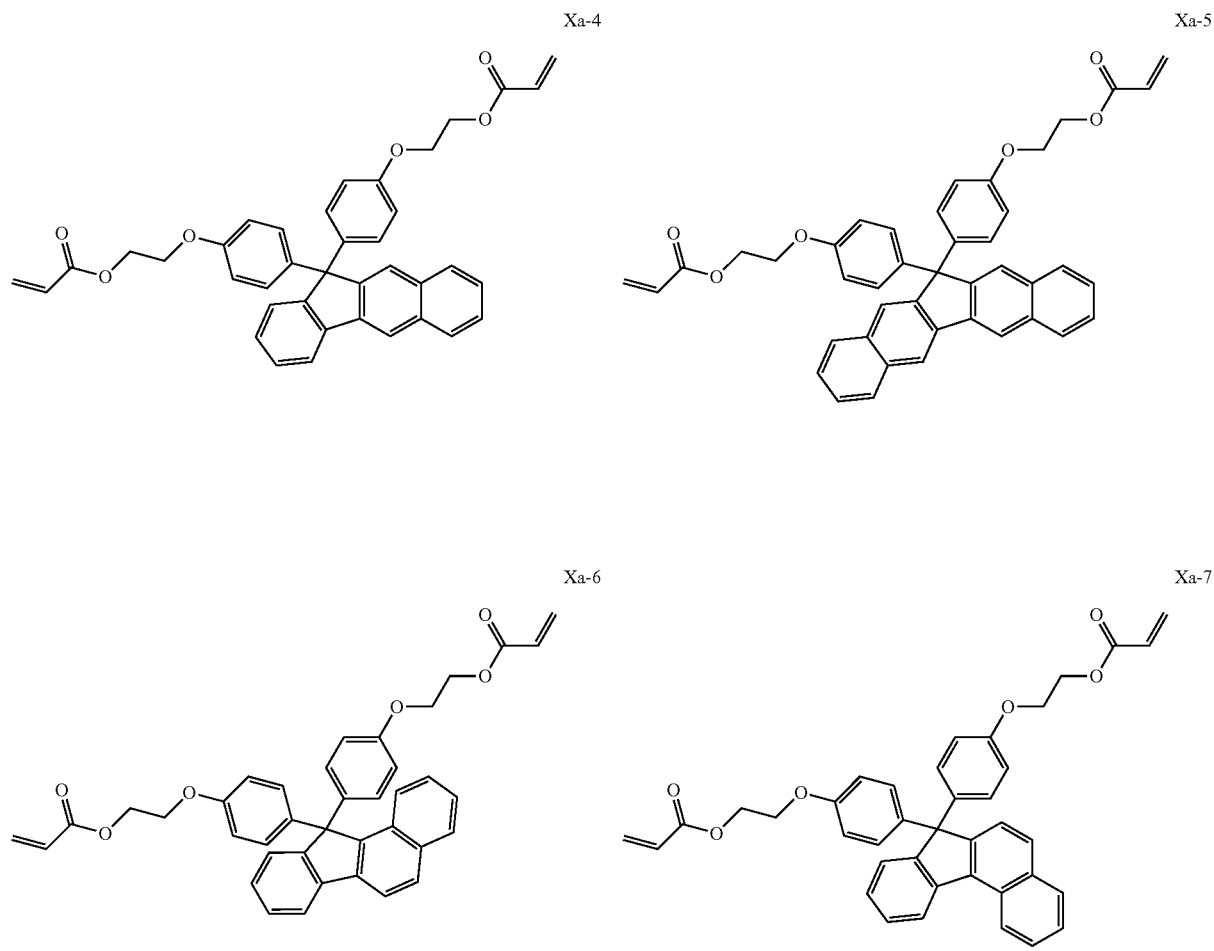

Xa-8
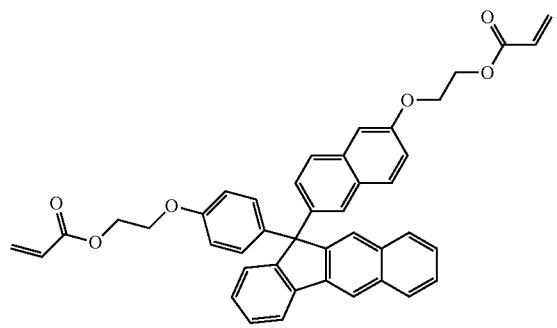
Xa-9
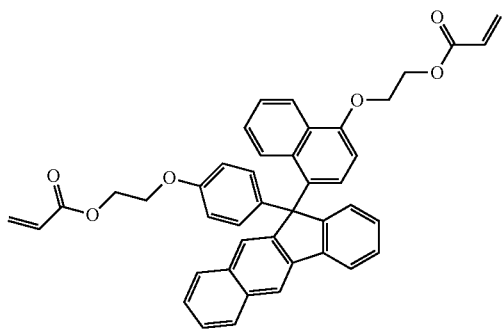
Xa-10
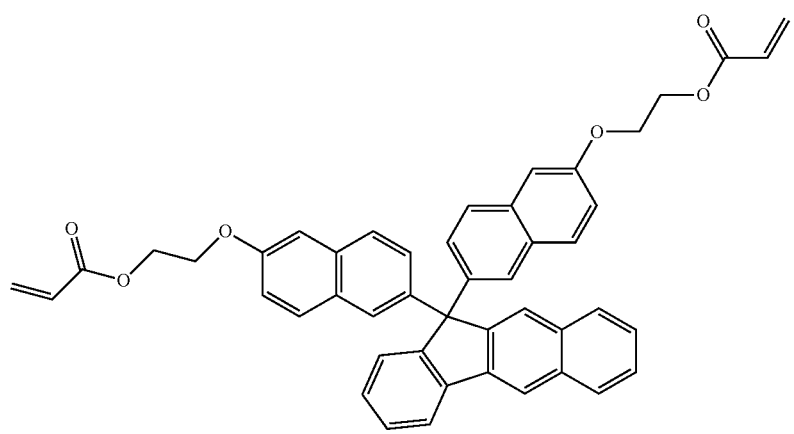
Xa-11
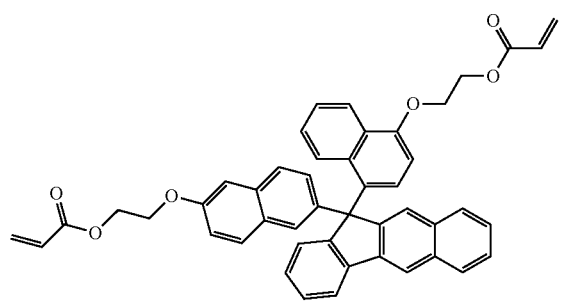
Xa-12
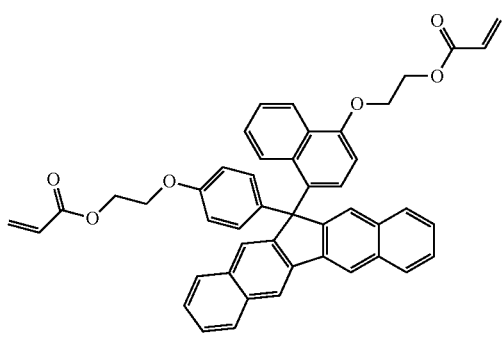
Xa-13
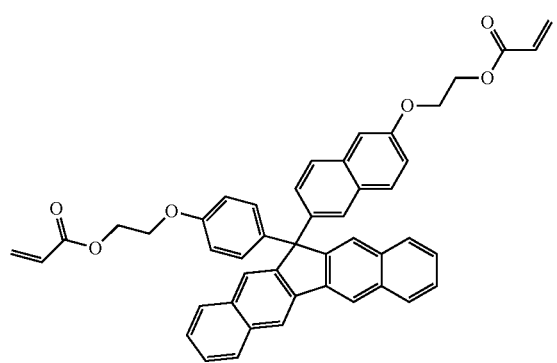
Xa-14
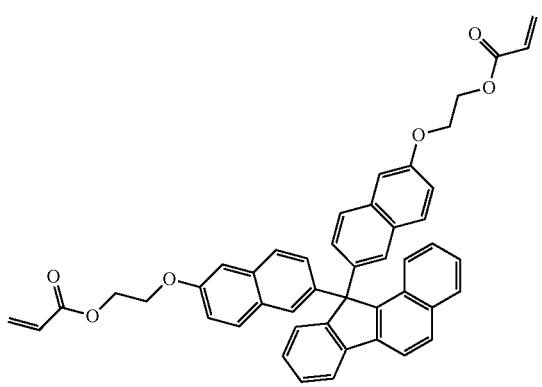

Xa-15

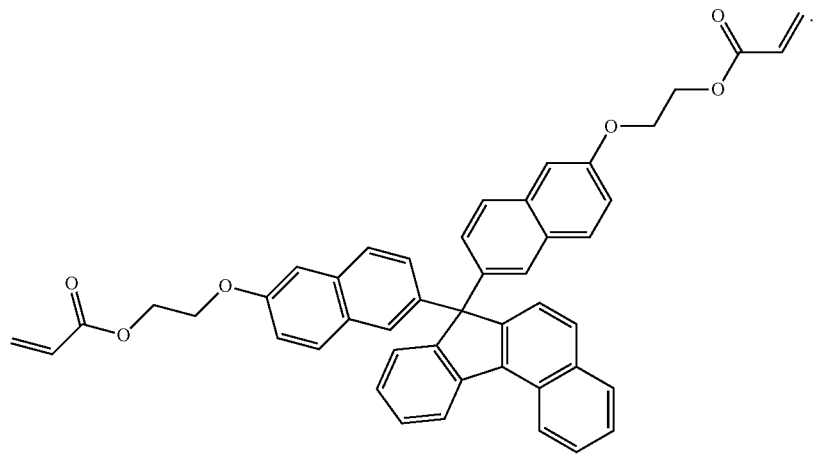

[11] The curable resin composition according to any one of [1] to [10], containing the non-conjugated vinylidene group-containing compound represented by the general formula (2) preferably in an amount of from 2 to 50% by mass relative to the condensed ring-containing compound represented by the general formula (1).

[12] The curable resin composition according to any one of [1] to [11], preferably containing a thermal-radical polymerization initiator and a photoradical polymerization initiator.

[13] The curable resin composition according to any one of [1] to [12], preferably further containing a monofunctional (meth)acrylate monomer, in which the content of the monofunctional (meth)acrylate monomer is preferably from 10 to 80% by mass relative to the condensed ring-containing compound represented by the general formula (1).

[14] A method for producing a semi-cured product, including curing the curable resin composition of any one of [1] to [13].

[15] The method for producing a semi-cured product according to [14], preferably including photoirradiating the curable resin composition.

[16] The method for producing a semi-cured product according to [14] or [15], wherein the curable resin composition is photoirradiated preferably to give a semi-cured product having a complex viscosity of from $10^5$ to $10^8$ mPa·s at 25° C. and at a frequency of 10 Hz.

[17] A semi-cured product produced according to the method for producing a semi-cured product of any one of [14] to [16].

[18] A method for producing a cured product, including a thermal polymerization step of putting the semi-cured product produced according to the method for producing a semi-cured product according to any one of [14] to [16], in a forming die for pressure formation therein, and heating it therein for thermal polymerization to give a cured product.

[19] A cured product produced according to the production method for a cured product of [18].

[20] An optical component using the cured product of [19].

[21] A lens using the cured product of [19].

[22] A compound represented by the following general formula (5):

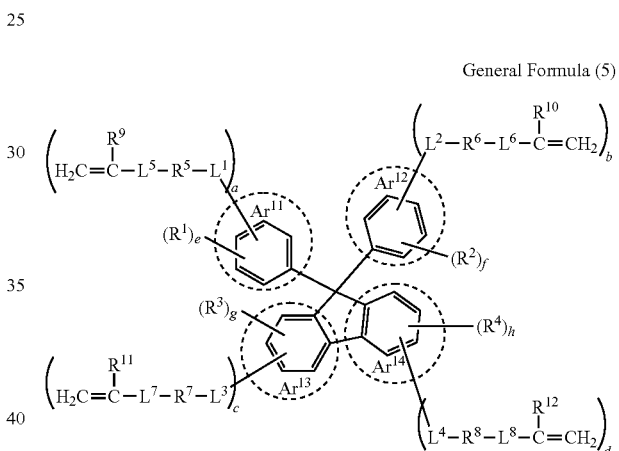

General Formula (5)

In the general formula (5), $Ar^{11}$ and $Ar^{12}$ each independently represent an aryl or heteroaryl group containing the benzene ring surrounded by the broken line, $Ar^{13}$ and $Ar^{14}$ each independently represent an aryl or heteroaryl group containing the benzene ring surrounded by the broken line, and at least one of $Ar^{13}$ and $Ar^{14}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, the upper limit of e and f each is 5-a and 5-b, respectively, the upper limit of g and h each is a value calculated by subtracting c or d from the possible maximum number of the substituents that $Ar^{13}$ and Ar[14] each may have. However, in a case where Ar[13] and Ar[14] each are an aromatic condensed ring group containing the benzene ring surrounded by the broken line as one condensed ring therein, the structures surrounded by c's or d's parentheses as well as R[3] and R[4] each may independently substitute on the benzene ring surrounded by the broken line or on any other ring than the benzene ring surrounded by the broken line.

[23] The compound according to [22], wherein in the general formula (5), preferably, Ar[13] and Ar[14] each are independently an aromatic hydrocarbon group having from 6 to 10 carbon atoms and containing the benzene ring surrounded by the broken line.

[24] The compound according to [22] or [23], wherein the compound represented by the general formula (5) is preferably represented by any of the following general formulae (6) to (9)

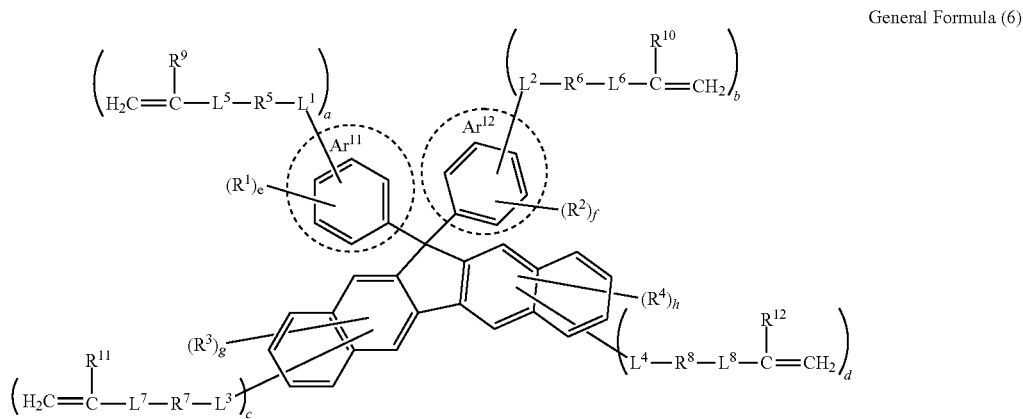

General Formula (6)

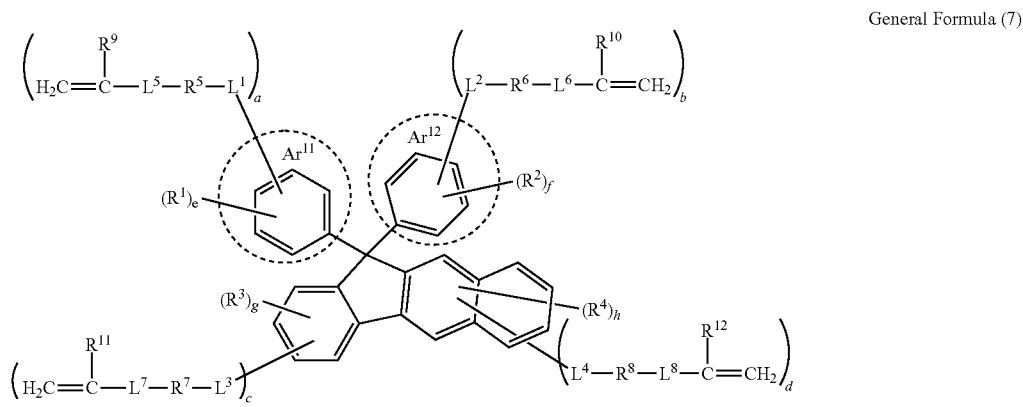

General Formula (7)

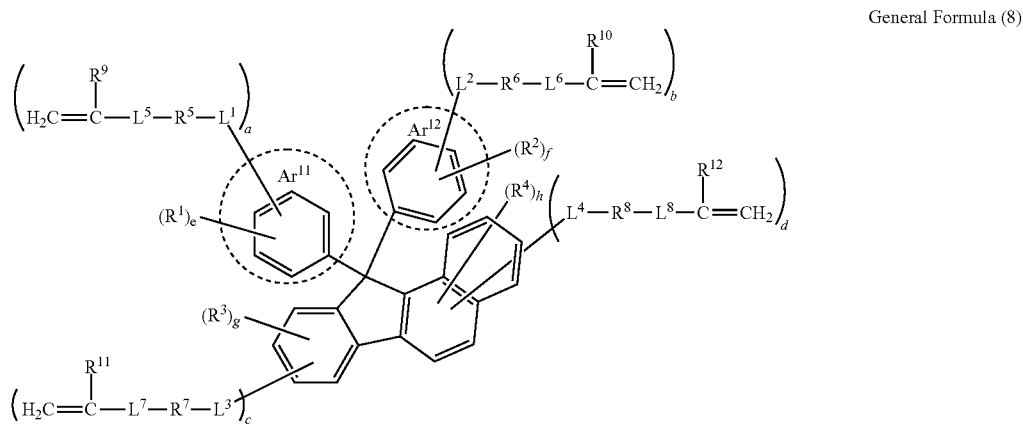

General Formula (8)

General Formula (9)

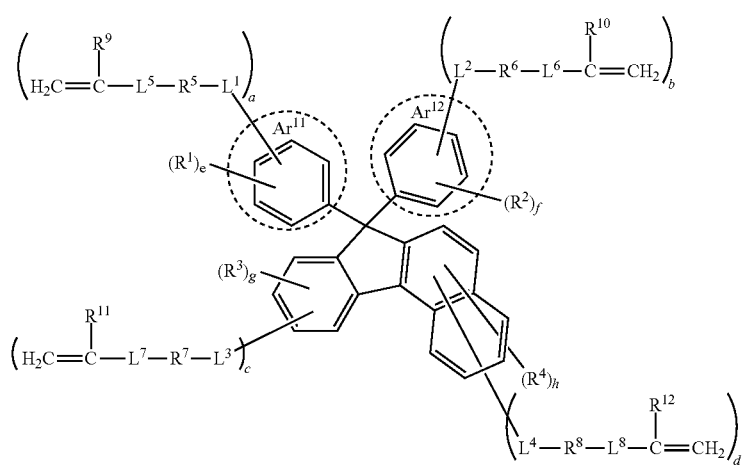

In the general formulae (6) to (9), $Ar^{11}$ and $Ar^{12}$ each independently represent an aryl or heteroaryl group containing the benzene ring surrounded by the broken line, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more. However, in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

[25] The compound according to [24], wherein the compound represented by the general formulae (6) to (9) is preferably represented by any of the following formulae (6A), (7A), (8A), (9A), (6B), (7B), (8B) and (9B):

General Formula (6A)

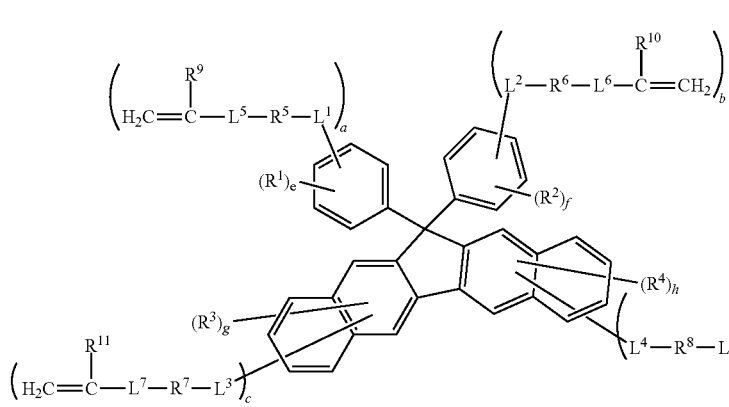

General Formula (7A)

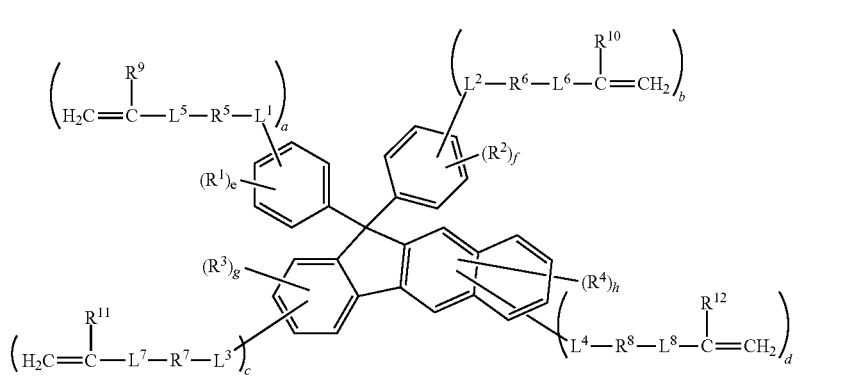

General Formula (8A)

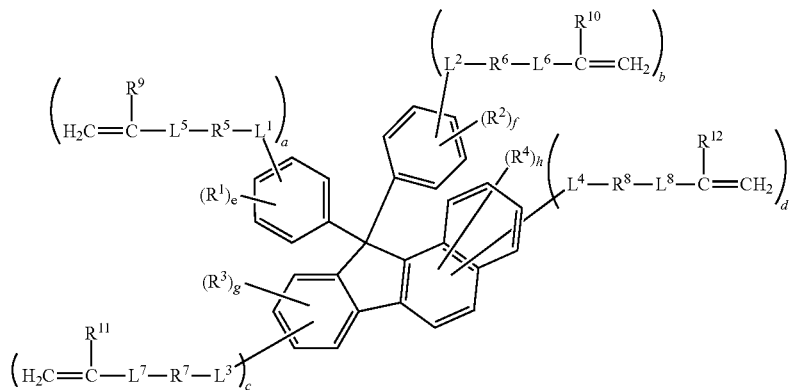

General Formula (9A)

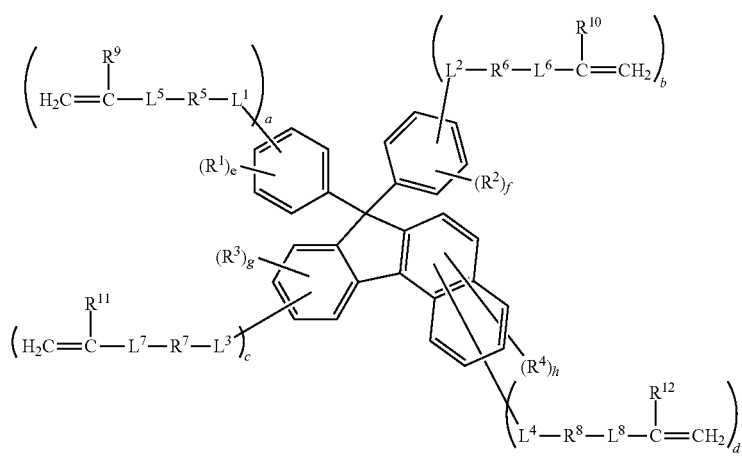

In the general formulae (6A), (7A), (8A) and (9A), $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, and e, f, g and h each independently indicate an integer of 0 or more.

General Formula (6B)

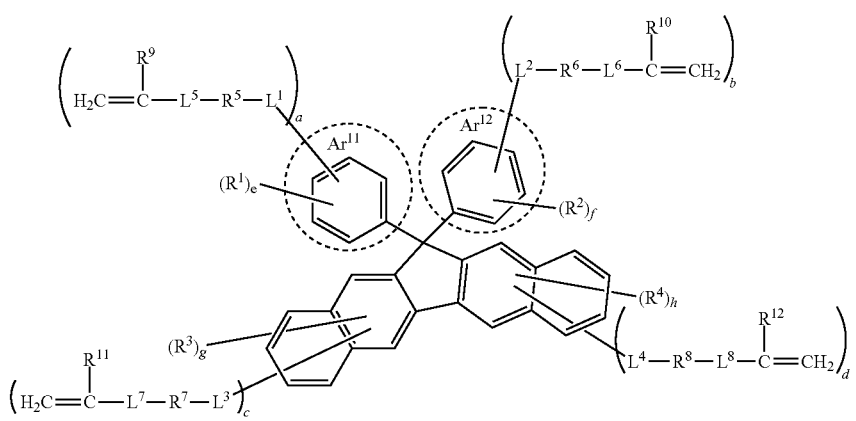

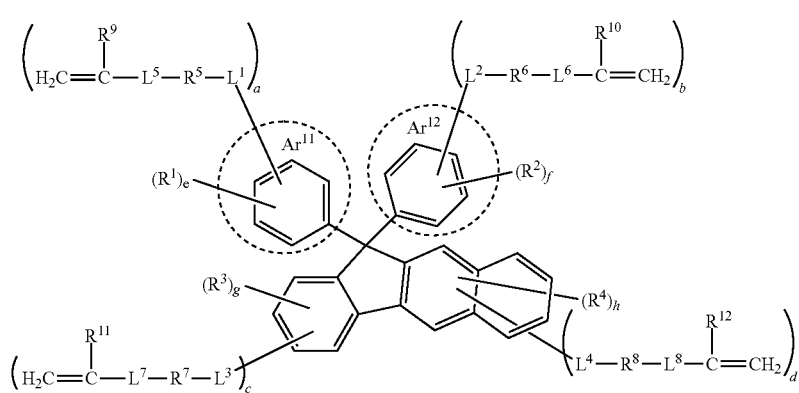

General Formula (7B)

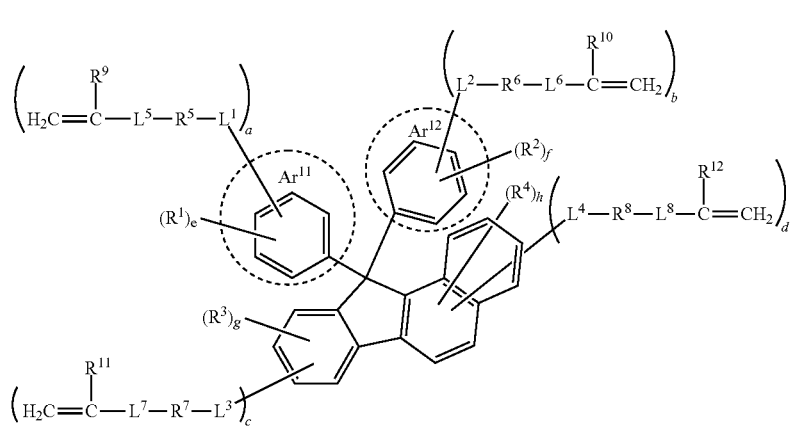

General Formula (8B)

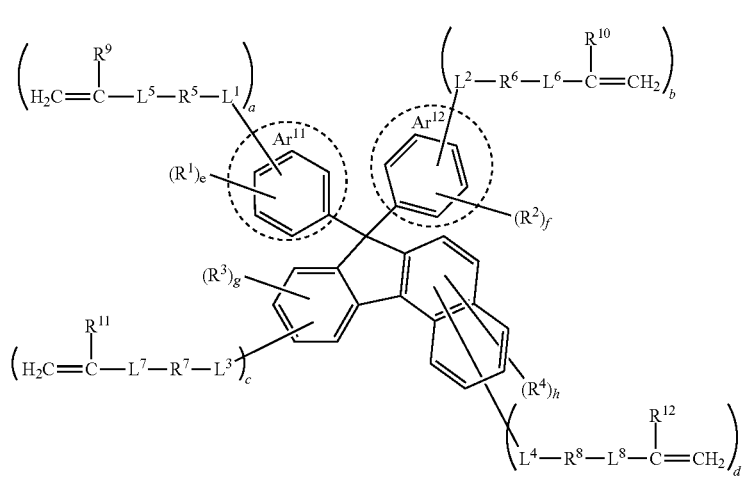

General Formula (9B)

In the general formulae (6B), (7B), (8B) and (9B), $Ar^{11}$ and $Ar^{12}$ each independently represent an aryl or heteroaryl group containing the benzene ring surrounded by the broken line, and at least one of $Ar^{11}$ and $Ar^{12}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more. However, in a case where Ar[11] and Ar[12] each are an aromatic condensed ring group containing the benzene ring surrounded by the broken line as one condensed ring therein, the structures surrounded by a's or b's parentheses as well as R[1] and R[2] each may independently substitute on the benzene ring surrounded by the broken line or on any other ring than the benzene ring surrounded by the broken line.

[26] The compound according to any one of [22] to [25], wherein in the general formulae (5) to (9), (6A), (7A), (8A), (9A), (6B), (7B), (8B) and (9B), preferably, $L^1$ to $L^4$ each are independently an oxygen atom or a sulfur atom, $L^5$ to $L^8$ each are independently an ester bond, a thioester bond or an amide bond, and $R^5$ to $R^8$ each are independently an alkylene group optionally having a substituent.

[27] The compound according to any one of [22] to [26], wherein in any of the general formulae (5) to (9), (6A), (7A), (8A), (9A), (6B), (7B), (8B) and (9B), preferably, c and d are both 0.

[28] The compound according to any one of [22] to [27], wherein the compound represented by the general formula (5) is preferably any of the following Xa-4 to Xa-15.

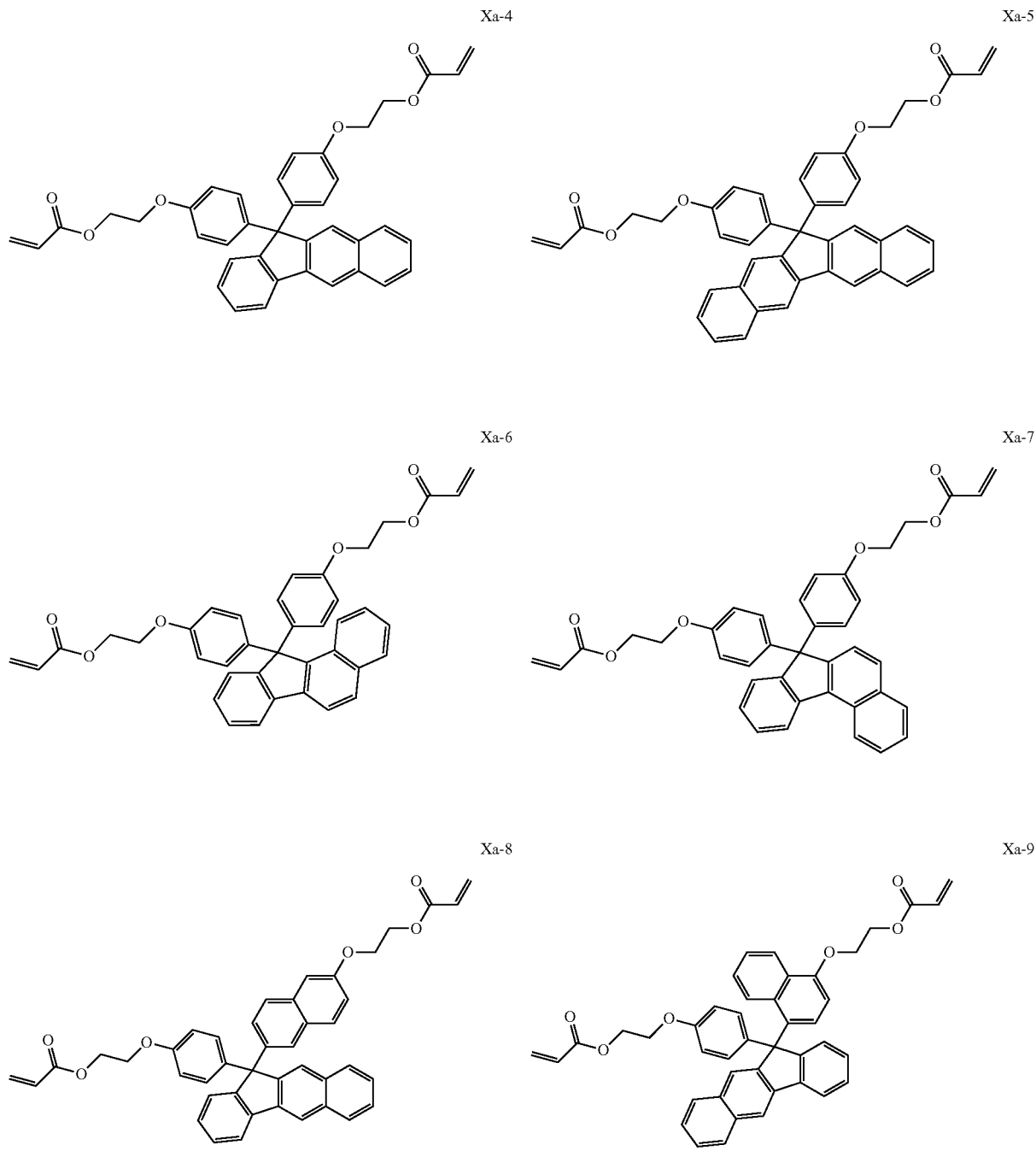

-continued
Xa-10
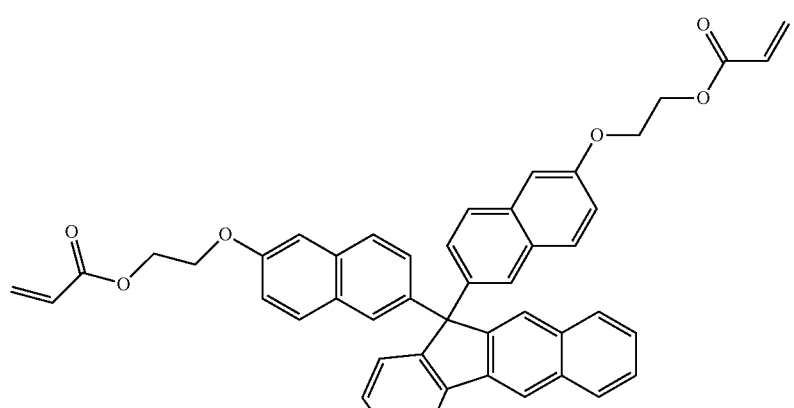
Xa-11
Xa-12
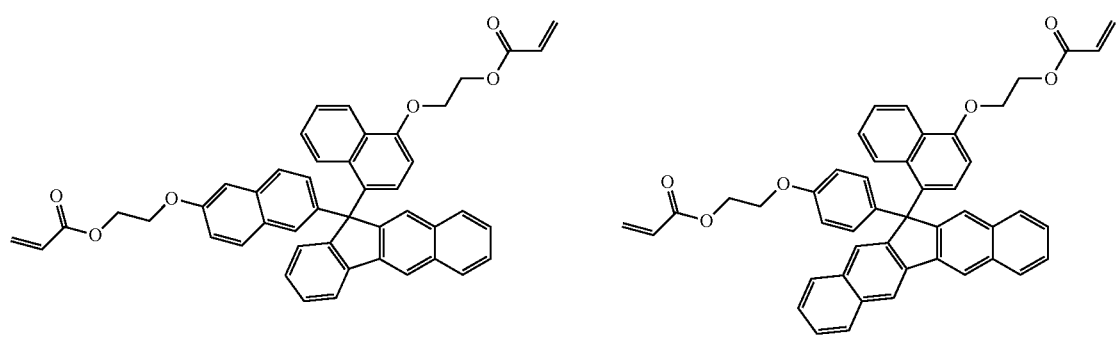
Xa-13
Xa-14
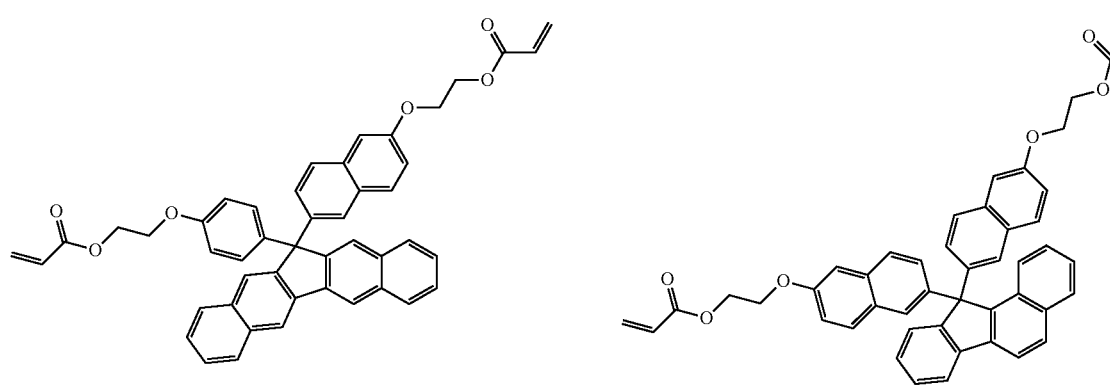
Xa-15
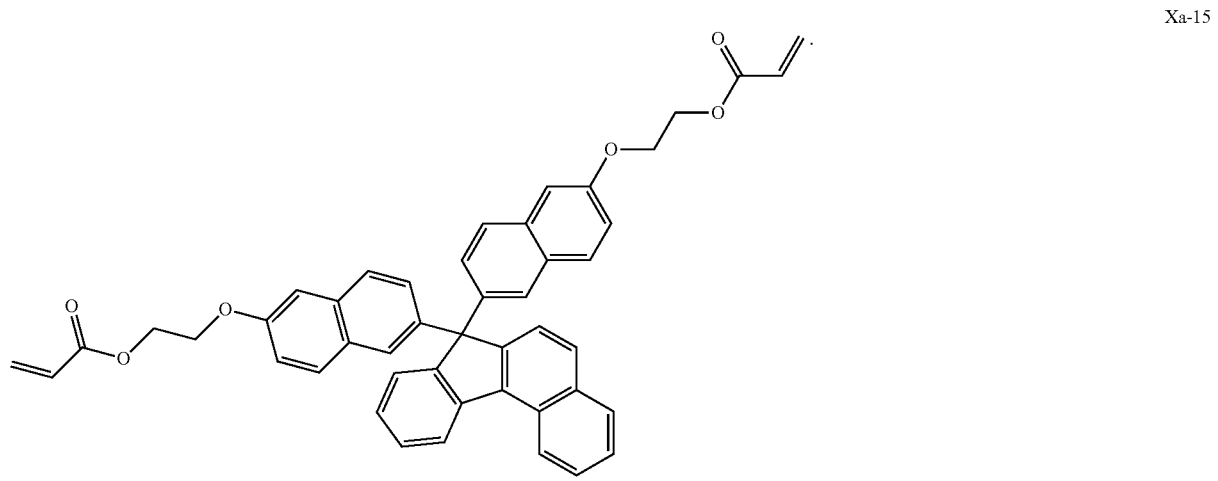

According to the invention, there is provided a curable resin composition capable of producing a cured product having a low Abbe's number and capable of realizing burr reduction in molding the composition.

DESCRIPTION OF EMBODIMENTS

Figure 1:
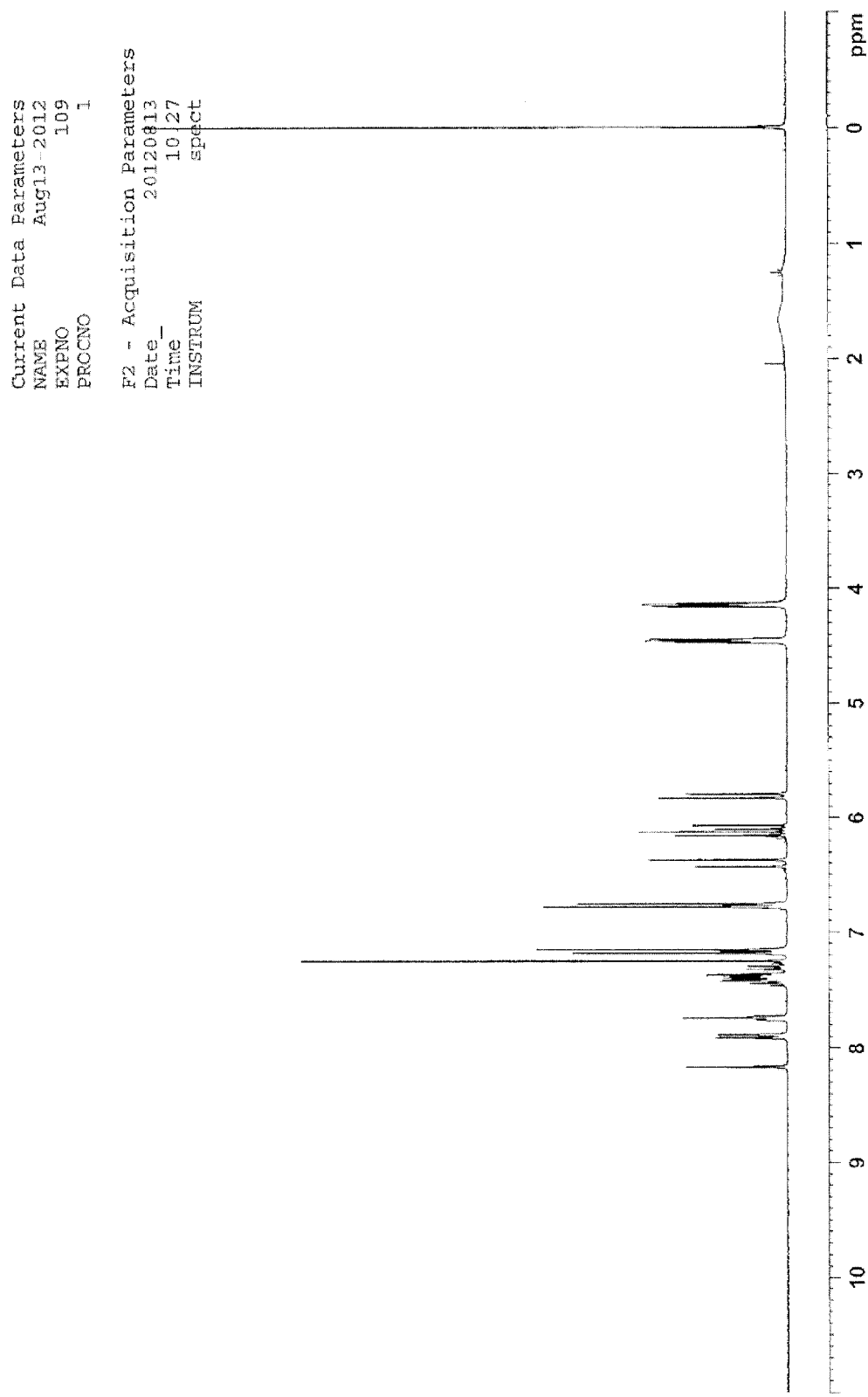
FIG. 1 is a $^1$H-NMR chart of the condensed ring-containing compound Xa-4.

The curable resin composition of the present invention, and the semi-cured product, the cured product and the method for producing these of the present invention, and the materials to be used in these are described in detail hereinunder.

The description of the constitutive elements of the invention given hereinunder is for some typical embodiments of the invention, to which, however, the invention should not be limited. In this description, the numerical range expressed by the wording "a number to another number" means the range that falls between the former number indicating the lower limit of the range and the latter number indicating the upper limit thereof.

[Curable Resin Composition]

The curable resin composition of the present invention contains a condensed ring-containing compound represented by the following general formula (1), a non-conjugated vinylidene group-containing compound represented by the following general formula (2), and at least one of a thermal- or optical-radical polymerization initiator.

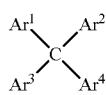

General Formula (1)

In the general formula (1), $Ar^1$ to $Ar^4$ each independently represent an aryl group optionally having a substituent or a heteroaryl group optionally having a substituent, at least one of $Ar^1$ to $Ar^4$ is an aromatic condensed ring group optionally having a substituent, and two or more of $Ar^1$ to $Ar^4$ contain a substituent having a polymerizable group. $Ar^1$ to $Ar^4$ may bond to each other.

The condensed ring-containing compound represented by the general formula (1) is preferred from the viewpoint of the ability thereof to remarkably better the mold releasability of the composition.

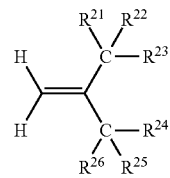

General Formula (2)

In the general formula (2), $R^{21}$ to $R^{26}$ each independently represent a substituent, at least one of $R^{21}$ to $R^{26}$ forms a ring, or at least two bond to each other to form a ring.

Having the constitution as above, the curable resin composition of the present invention can produce a cured product having a low Abbe's number while realizing burr reduction during molding. Not adhering to any theory, use of the condensed ring-containing compound represented by the general formula (1), which has at least one aromatic condensed ring skeleton and has two or more polymerizable groups, as a monomer lowers the Abbe s number of the cured product, and the formability of the semi-cured product can be given by controlling the three-dimensional structure thereof through chain transfer during polymerization with the non-conjugated vinylidene group-containing compound represented by the general formula (2), thereby realizing burr reduction to solve the above-mentioned problems.

Here, use of an aromatic ring-having monomer gives optical components having a low Abbe's number, and this is described in Quarterly Review of Chemistry (No. 39), Refractivity Control of Transparent Polymer, edited by the Chemical Society of Japan, pp. 174-177, etc. Concretely, an aromatic ring-having monomer has absorption at around 250 to 300 nm, and use of the monomer of the type lower the Abbe's number than in the case of using an aliphatic monomer having absorption at around 120 to 200 nm.

The condensed ring-containing compound represented by the general formula (1) has a long conjugated system. Extending the conjugated system to be longer lowers the Abbe's number and increases refractivity. A compound having a long conjugated system may absorb visible light.

Further, use of the condensed ring-containing compound represented by the general formula (1) enhances mold releasability in producing a cured product from the curable resin composition.

In this description, "(meth)acrylate" expresses acrylate and methacrylate; "(meth)acryl" expresses acryl and methacryl; and "(meth)acryloyl" expresses acryloyl and methacryloyl. In this description, monomer is differentiated from oligomer and polymer and is a compound having a weight-average molecular weight of at most 1,000.

<Condensed Ring-Containing Compound Represented by General Formula (1)>

The condensed ring-containing compound represented by the general formula (1) is described.

General Formula (1)

In the general formula (1), $Ar^1$ to $Ar^4$ each independently represent an aryl group optionally having a substituent or a heteroaryl group optionally having a substituent, at least one of $Ar^1$ to $Ar^4$ is an aromatic condensed ring group optionally having a substituent, and two or more of $Ar^1$ to $Ar^4$ contain a substituent having a polymerizable group. $Ar^1$ to $Ar^4$ may bond to each other.

The aryl group optionally having a substituent represented by $Ar^1$ to $Ar^4$ is preferably an aryl group having from 6 to 18 carbon atoms, more preferably an aryl group having from 6 to 14 carbon atoms, even more preferably an aryl group having from 6 to 10 carbon atoms.

The heteroaryl group optionally having a substituent represented by $Ar^1$ to $Ar^4$ is preferably a 4-membered to 12-membered heteroaryl group, more preferably a 6-membered to 10-membered heteroaryl group, even more preferably a 9-membered heteroaryl group. The hetero atom that constitutes the heteroaryl group optionally having a substituent represented by $Ar^1$ to $Ar^4$ includes a nitrogen atom, an oxygen atom, and a sulfur atom.

Preferably, $Ar^1$ to $Ar^4$ each are independently an aryl group optionally having a substituent.

The aromatic condensed ring group optionally having a substituent represented by $Ar^1$ to $Ar^4$ is preferably an aryl group having from 9 to 12 carbon atoms, or a 4-membered to 12-membered heteroaryl group, more preferably an aryl group having from 9 to 10 carbon atoms, or a 6-membered to 10-membered heteroaryl group, and is even more preferably a naphthyl group or a 9-membered heteroaryl group, from the viewpoint of the ability of the compound to prevent discoloration without extending so much the conjugated system. Still more preferably, the group is a naphthyl group, and is especially preferably a β-naphthyl group.

At least one of $Ar^1$ to $Ar^4$ is an aromatic condensed ring group optionally having a substituent, and preferably from 1 to 3 of these each are an aromatic condensed ring group optionally having a substituent. More preferably one or two of these each are an aromatic condensed ring group optionally having a substituent.

The substituent of the aryl group or the heteroaryl group optionally having a substituent represented by $Ar^1$ to $Ar^4$ is not specifically defined except that two or more of $Ar^1$ to $Ar^4$ contain a substituent having a polymerizable group.

The polymerizable group that the substituent for $Ar^1$ to $Ar^4$ has is preferably a polymerizable group capable of undergoing radical polymerization or cationic polymerization (hereinafter referred to as a radical-polymerizable group or a cationic-polymerizable group).

The radical-polymerizable group may be any known radical-polymerizable group, and as a preferred example thereof, there is mentioned a radical-polymerizable, ethylenic unsaturated bond-having polymerizable group. Concretely, the group includes a vinyl group, a (meth)acryloyloxy group, etc. Above all, preferred is a (meth)acryloyloxy group, and more preferred is an acryloyloxy group.

The cationic-polymerizable group may be any known cationic-polymerizable group. Concretely, there are mentioned an alicyclic ether group, a cyclic acetal group, a cyclic lactone group, a cyclic thioether group, a spiro-orthoester group, a vinyloxy group, etc. Above all, preferred are an alicyclic ether group, and a vinyloxy group, and more preferred are an epoxy group, an oxetanyl group, and a vinyloxy group.

The polymerizable group that the substituent for $Ar^1$ to $Ar^4$ has is preferably a radical-polymerizable group.

Two or more of $Ar^1$ to $Ar^4$ contain a substituent having a polymerizable group. Preferably from 2 to 4 of $Ar^1$ to $Ar^4$ contain a substituent having a polymerizable group, more preferably 2 or 3 of $Ar^1$ to $Ar^4$ contain a substituent having a polymerizable group, and even more preferably two of $Ar^1$ to $Ar^4$ contain a substituent having a polymerizable group.

In the general formula (1), $Ar^1$ to $Ar^4$ may bond to each other. The ring to be formed by $Ar^1$ to $Ar^4$ bonding to each other is preferably an alicyclic ring. The linking group via which $Ar^1$ to $Ar^4$ bond to each other includes a single bond, —O—, etc. Preferred is a single bond. The number of the members of the ring to be formed by $Ar^1$ to $Ar^4$ bonding to each other (this means one ring containing the linking group via which $Ar^1$ to $Ar^4$ bond to each other, and is not the whole of the condensed ring formed as a result of bonding of $Ar^1$ to $Ar^4$ to each other) is preferably 5 or 6, and is more preferably 5.

In a case where $Ar^1$ to $Ar^4$ bond to each other, preferably the adjacent two of $Ar^1$ to $Ar^4$ bond to each other, more preferably $Ar^3$ and $Ar^4$ bond to each other, and even more preferably, of $Ar^1$ to $Ar^4$, $Ar^3$ and $Ar^4$ alone bond to each other.

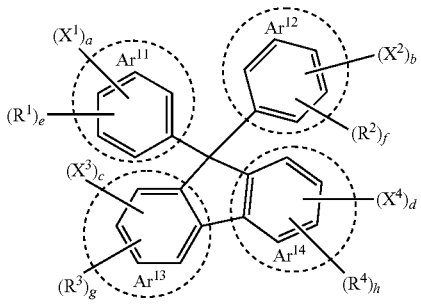

General Formula (3)

In the general formula (3), $Ar^{11}$ to $Ar^{14}$ each independently represent an aryl or heteroaryl group containing the benzene ring surrounded by the broken line, and at least one of $Ar^{11}$ to $Ar^{14}$ is an aromatic condensed ring group containing the benzene ring surrounded by the broken line as one condensed ring therein. $X^1$ to $X^4$ each independently represent a substituent having a polymerizable group, and the carbon atom in the substituent may be substituted with a hetero atom. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, and the upper limit of e, f, g and h each is a value calculated by subtracting a, b, c or d from the possible maximum number of the substituents that $Ar^{11}$ to $Ar^{14}$ each may have. However, in a case where $Ar^{11}$ to $Ar^{14}$ each are an aromatic condensed ring group containing the benzene ring surrounded by the broken line as one condensed ring therein, $X^1$ to $X^4$ and $R^1$ to $R^4$ each may independently substitute on the benzene ring surrounded by the broken line or on any other ring than the benzene ring surrounded by the broken line.

In the general formula (3), the preferred range of the aryl group containing the benzene ring surrounded by the broken line represented by $Ar^{11}$ to $Ar^{14}$ is the same as the preferred range of the aryl group optionally having a substituent represented by $Ar^1$ to $Ar^4$ in the general formula (1).

In the general formula (3), the heteroaryl group containing the benzene ring surrounded by the broken line represented by $Ar^{11}$ to $Ar^{14}$ is preferably a 9-membered to 14-membered heteroaryl group, more preferably a 9-membered to 10-membered heteroaryl group, even more preferably a 9-membered heteroaryl group. The hetero atom that constitutes the heteroaryl group optionally having a substituent represented by $Ar^{11}$ to $Ar^{14}$ is the same as the hetero atom that constitutes the heteroaryl group represented by $Ar^1$ to $Ar^4$ in the general formula (1).

Preferably, $Ar^{11}$ to $Ar^{14}$ each are independently an aryl group containing the benzene ring surrounded by the broken line.

In the general formula (3), the preferred range of the aromatic condensed ring group containing the benzene ring surrounded by the broken line as one condensed ring therein, represented by $Ar^{11}$ to $Ar^{14}$, is the same as the aromatic condensed ring group optionally having a substituent represented by $Ar^1$ to $Ar^4$ in the general formula (1).

In the general formula (3), preferably, $Ar^{11}$ and $Ar^{12}$ each are independently an aromatic hydrocarbon group having from 6 to 10 carbon atoms (and containing the benzene ring surrounded by the broken line) from the viewpoint of reducing the Abbe's number.

In the general formula (3), preferably, $Ar^{13}$ and $Ar^{14}$ each are independently an aromatic hydrocarbon group having from 6 to 10 carbon atoms (and containing the benzene ring surrounded by the broken line) from the viewpoint of reducing the Abbe's number, and more preferably, at least one of $Ar^{13}$ and $Ar^{14}$ is an aromatic hydrocarbon group having 10 carbon atoms (and containing the benzene ring surrounded by the broken line).

In the general formula (3), $X^1$ to $X^4$ each independently represent a substituent having a polymerizable group, and the carbon atom in the substituent may be substituted with a hetero atom. The substituent having a polymerizable group represented by $X^1$ to $X^4$ is not specifically defined, but is preferably an aliphatic group having a polymerizable group.

The aliphatic group having a polymerizable group represented by $X^1$ to $X^4$ is not specifically defined, but is preferably an alkylene group having from 1 to 12 carbon atoms in addition to the polymerizable group, more preferably an aliphatic group having from 2 to 10 carbon atoms, even more preferably an alkylene group having from 2 to 5 carbon atoms.

In the aliphatic group having a polymerizable group represented by $X^1$ to $X^4$ where the aliphatic group is substituted with a hetero atom, preferably, the group is substituted with any of —NR— (where R is a substituent), an oxygen atom and a sulfur atom, more preferably, —$CH_2$— not adjacent to each other in the aliphatic group is substituted with an oxygen atom or a sulfur atom, and even more preferably, —$CH_2$— not adjacent to each other in the aliphatic group is substituted with an oxygen atom. The aliphatic group having a polymerizable group represented by $X^1$ to $X^4$ is preferably substituted with a hetero atom in one or two sites therein, more preferably with a hetero atom in one site, and even more preferably with a hetero atom in one site adjacent to the aryl group containing the benzene ring surrounded by the broken line represented by $Ar^{11}$ to $Ar^{14}$.

In the aliphatic group having a polymerizable group represented by $X^1$ to $X^4$, the preferred range of the polymerizable group is the same as the preferred range of the polymerizable group that the substituent for $Ar^1$ to $Ar^4$ has.

In case where $Ar^{11}$ to $Ar^{14}$ each are independently an aromatic condensed ring group containing the benzene ring surrounded by the broken line as one condensed ring therein, $X_1$ to $X^4$ each may independently substitute on the benzene ring surrounded by the broken line or on any other ring than the benzene ring surrounded by the broken line.

In the general formula (3), a and b each independently indicate an integer of from 1 to 5, preferably 1 or 2, and more preferably, both a and b are one.

In the general formula (3), c and d each independently indicate an integer of from 0 to 5, preferably 0 or 1, and more preferably both c and d are 0.

In the general formula (3), $R^1$ to $R^4$ each independently represent a substituent. The substituent represented by $R^1$ to $R^4$ is not specifically defined, including, for example, a halogen atom, a halogenoalkyl group, an alkyl group, an alkenyl group, an acyl group, a hydroxyl group, a hydroxyalkyl group, a alkoxy group, an aryl group, a heteroaryl group, an alicyclic group, etc. The substituent represented by $R^1$ to $R^4$ is preferably an alkyl group, an alkoxy group or an aryl group, more preferably an alkyl group having from 1 to 5 carbon atoms, an alkoxy group having from 1 to 5 carbon atoms, or a phenyl group, even more preferably a methyl group, a methoxy group or a phenyl group.

In the general formula (3) where $Ar^{11}$ to $Ar^{14}$ are each independently an aromatic condensed ring group containing the benzene ring surrounded by the broken line as one condensed ring therein, $R^1$ to $R^4$ each may independently substitute on the benzene ring surrounded by the broken line or on any other ring than the benzene ring surrounded by the broken line.

In the general formula (3), e, f, g and h each independently indicate an integer of 0 or more, and the upper limit of e, f, g and h each is a value calculated by subtracting a, b, c or d from the possible maximum number of the substituents that $Ar^{11}$ to $Ar^{14}$ each may have.

Preferably, e, f, g and h each are independently from 0 to 8, more preferably from 0 to 2, even more preferably 0.

In case where $Ar^{11}$ to $Ar^{14}$ each are an aromatic condensed ring group containing the benzene ring surrounded by the broken line as one condensed ring therein, preferably, e, f, g and h each are 0 or 1, more preferably 0.

The condensed ring-containing compound represented by the general formula (1) is preferably represented by the following general formula (4):

General Formula (4)

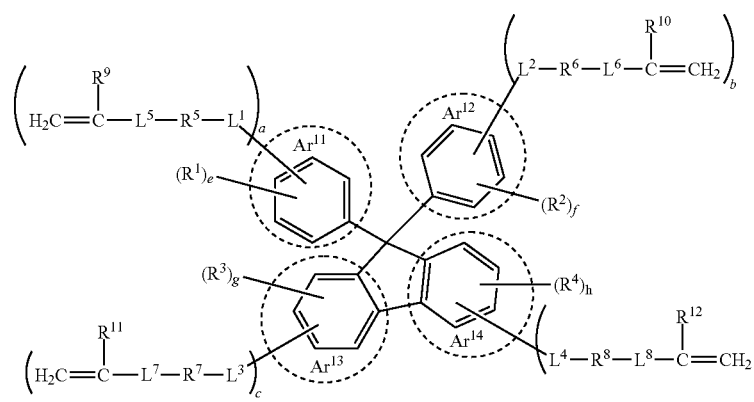

In the general formula (4), $Ar^{11}$ to $Ar^{14}$ each independently represent an aryl or heteroaryl group containing the benzene ring surrounded by the broken line, and at least one of $Ar^{11}$ to $Ar^{14}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, and the upper limit of e, f, g and h each is a value calculated by subtracting a, b, c or d from the possible maximum number of the substituents that $Ar^{11}$ to $Ar^{14}$ each may have. However, in a case where $Ar^{11}$ to $Ar^{14}$ each are an aromatic condensed ring group containing the benzene ring surrounded by the broken line as one condensed ring therein, the structures surrounded by a's, b's, c's or d's parentheses as well as $R^1$ to $R^4$ each may independently substitute on the benzene ring surrounded by the broken line or on any other ring than the benzene ring surrounded by the broken line.

ing a substituent, preferably an alkylene group optionally having a substituent, more preferably an alkylene group having from 1 to 5 carbon atoms and optionally having a substituent, even more preferably an alkylene group having from 1 to 3 carbon atoms and optionally having a substituent, still more preferably an ethylene group optionally having a substituent.

In $R^5$ to $R^8$ each representing an alkylene group optionally having a substituent, the substituent is not specifically defined.

In the general formula (4), $L^5$ to $L^8$ each independently represent a single bond, an ester bond, a thioester bond or an amide bond, preferably an ester bond, a thioester bond or an amide bond, more preferably an ester bond.

When $L^5$ to $L^8$ each are an ester bond, the ester bond may be any of —C(=O)—O— or —O—C(=O)— from the side of the carbon atom to which $R^9$ to $R^{12}$ bond, but is preferably —C(=O)—O—.

In the general formula (4), $R^9$ to $R^{12}$ each independently represent a hydrogen atom or a methyl group, preferably a hydrogen atom.

The condensed ring-containing compound represented by the general formula (1) is preferably represented by the following general formula (5).

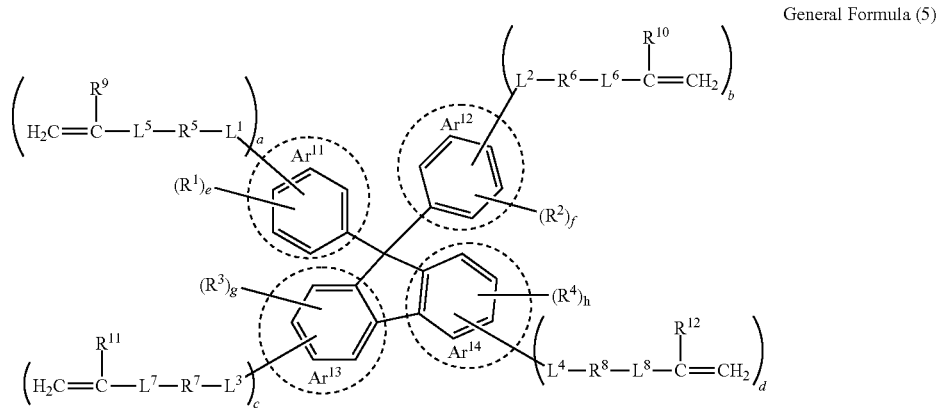

General Formula (5)

The preferred range of $Ar^{11}$ to $Ar^{14}$ in the general formula (4) is the same as the preferred range of $Ar^{11}$ to $Ar^{14}$ in the general formula (3).

The preferred range of $R^1$ to $R^4$ in the general formula (4) is the same as the preferred range of $R^1$ to $R^4$ in the general formula (3).

The preferred range of a and b in the general formula (4) is the same as the preferred range of a and b in the general formula (3).

The preferred range of c and d in the general formula (4) is the same as the preferred range of c and d in the general formula (3).

The preferred range of e, f, g and h in the general formula (4) is the same as the preferred range of e, f, g and h in the general formula (3).

In the general formula (4), $L^1$ to $L^4$ each independently represent a single bond, an oxygen atom or a sulfur atom, preferably an oxygen atom or a sulfur atom, more preferably an oxygen atom.

In the general formula (4), $R^5$ to $R^8$ each independently represent a single bond or an alkylene group optionally hav- In the general formula (5), $Ar^{11}$ and $Ar^{12}$ each independently represent an aryl or heteroaryl group containing the benzene ring surrounded by the broken line, $Ar^{13}$ and $Ar^{14}$ each independently represent an aryl or heteroaryl group containing the benzene ring surrounded by the broken line, and at least one of $Ar^{13}$ and $Ar^{14}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more, the upper limit of e and f each is 5-a and 5-b, respectively, the upper limit of g and h each is a value calculated by subtracting c or d from the possible maximum number of the substituents that $Ar^{13}$ and $Ar^{14}$ each may have. However, in a case where $Ar^{11}$ to $Ar^{14}$ each are an aromatic condensed ring group containing the benzene ring surrounded by the broken line as one condensed ring therein, the structures surrounded by a's, b's, c's or d's parentheses as well as $R^1$ to $R^4$ each may independently substitute on the benzene ring surrounded by the broken line or on any other ring than the benzene ring surrounded by the broken line.

In the general formula (5), the preferred range of $Ar^{11}$ and $Ar^{12}$ is the same as the preferred range of $Ar^{11}$ and $Ar^{12}$ in the general formula (3).

In the general formula (5), the preferred range of $Ar^{13}$ and $Ar^{14}$ is the same as the preferred range of $Ar^{13}$ and $Ar^{14}$ in the general formula (3). However, when $Ar^{11}$ and $Ar^{12}$ are both an aromatic hydrocarbon group having 10 carbon atoms, more preferably, $Ar^{13}$ and $Ar^{14}$ in the general formula (5) are both an aromatic hydrocarbon group having 10 carbon atoms (and containing the benzene ring surrounded by the broken line).

In the general formula (5), the preferred range of $R^1$ to $R^{12}$ is the same as the preferred range of $R^1$ to $R^{12}$ in the general formula (3).

In the general formula (5), the preferred range of $L^1$ to $L^8$ is the same as the preferred range of $L^1$ to $L^4$ in the general formula (4).

In the general formula (5), the preferred range of a and b is the same as the preferred range of a and b in the general formula (3).

In the general formula (5), the preferred range of c and d is the same as the preferred range of c and d in the general formula (3).

In the general formula (5), the preferred range of e, f, g and h is the same as the preferred range of e, f, g and h in the general formula (3).

The condensed ring-containing compound represented by the general formula (5) is preferably represented by any of the following general formulae (6) to (9):

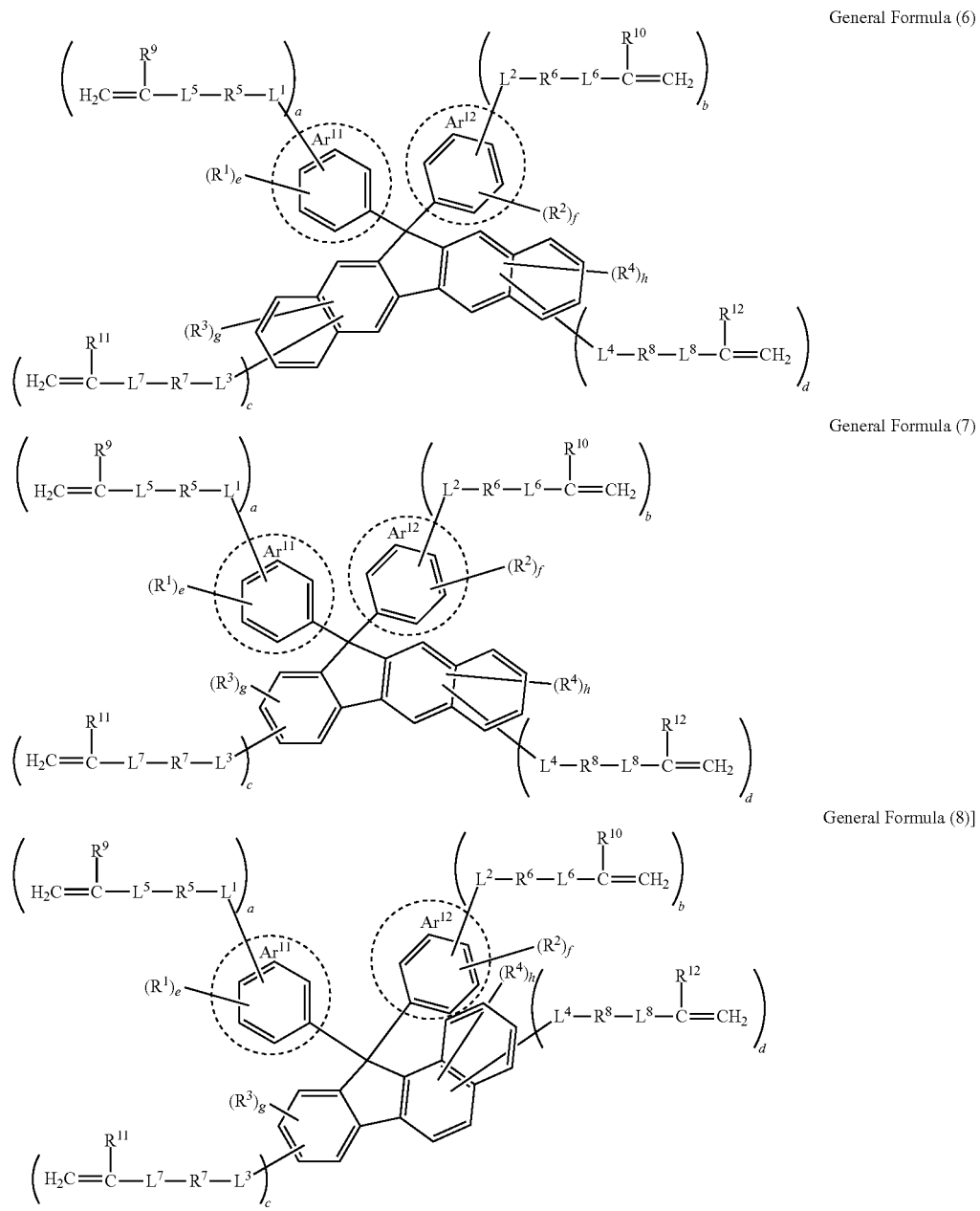

General Formula (6)

General Formula (7)

General Formula (8)]

General Formula (9)

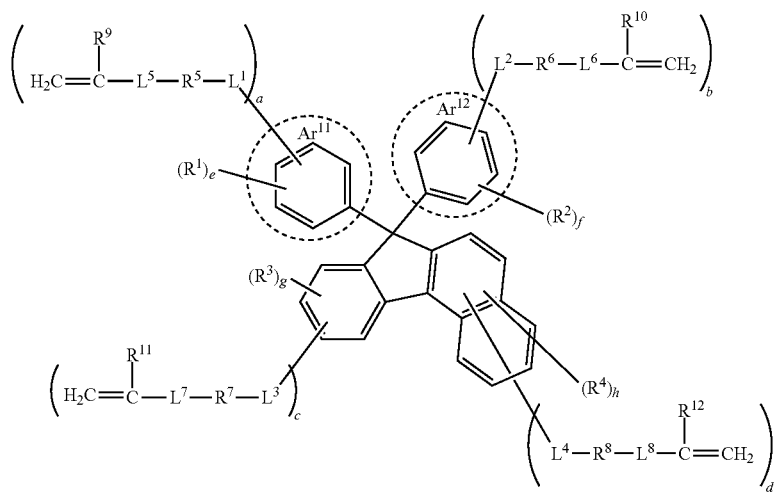

In the general formulae (6) to (9), $Ar^{11}$ and $Ar^{12}$ each independently represent an aryl or heteroaryl group containing the benzene ring surrounded by the broken line, $L^1$ to $L^4$ each independently represent a single bond, an oxygen atom, or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more. However, in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

In the above-mentioned general formulae (6) to (9) and in the general formulae (6A), (7A), (8A), (9A), (6B), (7B), (8B) and (9B) to be mentioned below, the structures surrounded by a's, b's, c's or d's parentheses as well as $R^1$ to $R^4$ substituting on the naphthalene ring each may substitute on any of the two benzene rings constituting the naphthalene ring. For example, $R^3$ in the general formula (6) may substitute on the benzene ring adjacent to the 5-membered ring or on the benzene ring not adjacent to the 5-membered ring.

In the general formulae (6) to (9), the preferred range of $Ar^{11}$ and $Ar^{12}$ is the same as the preferred range of $Ar^{11}$ and $Ar^{12}$ in the general formula (5). However, in the general formulae (6), (8) and (9), more preferably, both $Ar^{11}$ and $Ar^{12}$ are an aromatic hydrocarbon group having 6 carbon atoms (and containing the benzene ring surrounded by the broken line); and in the general formula (7), more preferably, at least one of $Ar^{11}$ and $Ar^{12}$ is an aromatic hydrocarbon group having 10 carbon atoms (and containing the benzene ring surrounded by the broken line).

In the general formulae (6) to (9), the preferred range of $R^1$ to $R^{12}$ is the same as the preferred range of $R^1$ to $R^{12}$ in the general formula (5).

In the general formulae (6) to (9), the preferred range of $L^1$ to $L^8$ is the same as the preferred range of $L^1$ to $L^4$ in the general formula (5).

In the general formulae (6) to (9), the preferred range of a and b is the same as the preferred range of a and b in the general formula (5).

In the general formulae (6) to (9), the preferred range of c and d is the same as the preferred range of c and d in the general formula (5).

In the general formulae (6) to (9), the preferred range of e, f, g and h is the same as the preferred range of e, f, g and h in the general formula (5).

The condensed ring-containing compound represented by the general formulae (6) to (9) is preferably represented by any of the following general formulae (6A), (7A), (8A), (9A), (6B), (7B), (8B) and (9B):

General Formula (6A)

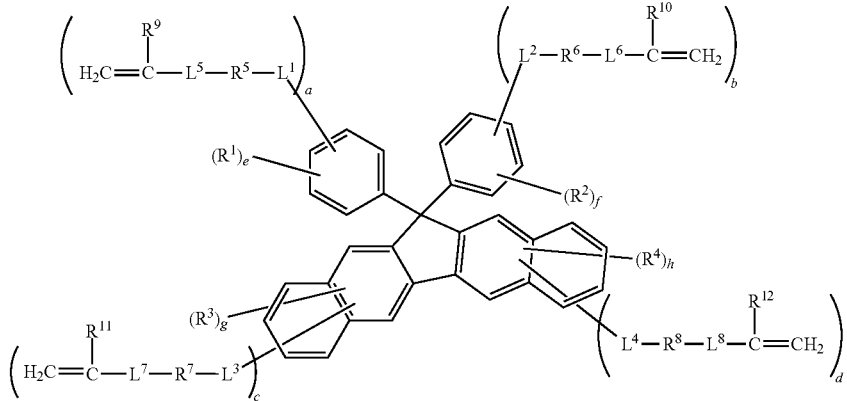

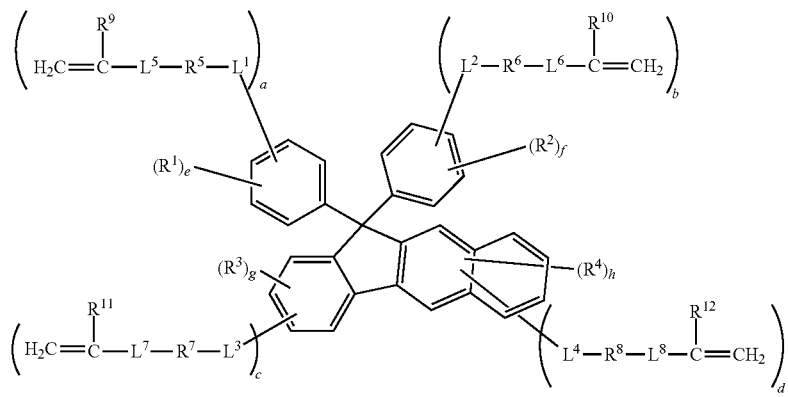

General Formula (7A)

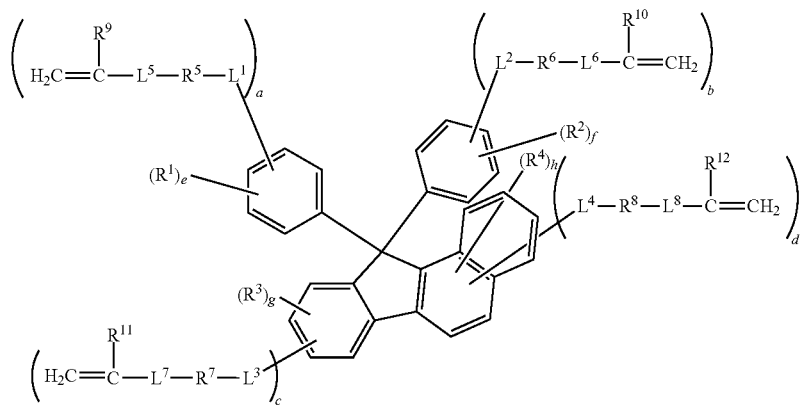

General Formula (8A)

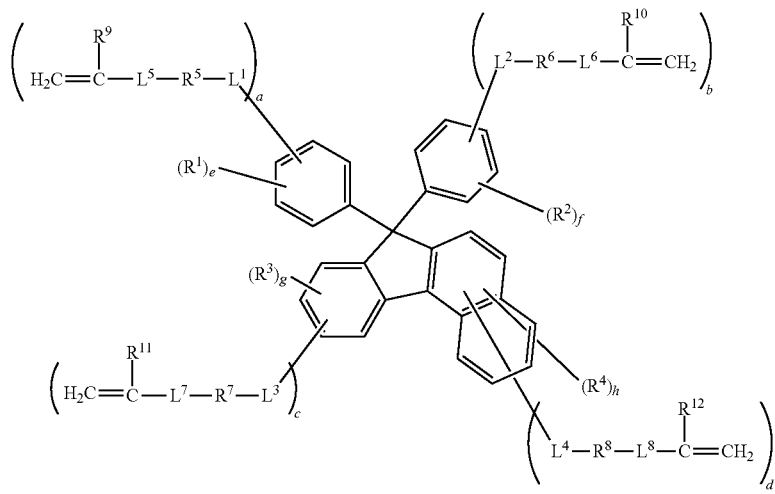

General Formula (9A)

In the general formulae (6A), (7A), (8A) and (9A), $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group. a and b each independently indicate an integer of from 1 to 5, and c and d each independently indicate an integer of from 0 to 5. $R^1$ to $R^4$ each independently represent a substituent, and e, f, g and h each independently indicate an integer of 0 or more.

In the general formulae (6A), (7A), (8A) and (9A), the preferred range of $R^1$ to $R^{12}$ is the same as the preferred range of $R^1$ to $R^{12}$ in the general formulae (6), (7), (8) and (9).

In the general formulae (6A), (7A), (8A) and (9A), the preferred range of $L^1$ to $L^8$ is the same as the preferred range of $L^1$ to $L^4$ in the general formulae (6) to (9).

In the general formulae (6A), (7A), (8A) and (9A), the preferred range of a and b is the same as the preferred range of a and b in the general formulae (6) to (9).

In the general formulae (6A), (7A), (8A) and (9A), the preferred range of c and d is the same as the preferred range of c and d in the general formulae (6) to (9)'.

In the general formulae (6A), (7A), (8A) and (9A), the preferred range of e, f, g and h is the same as the preferred range of e, f, g and h in the general formulae (6) to (9).

General Formula (6B)

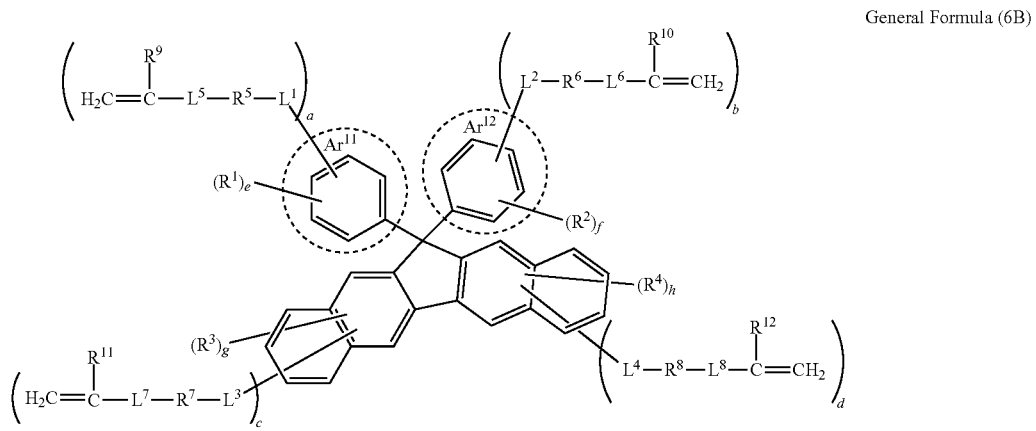

General Formula (7B)

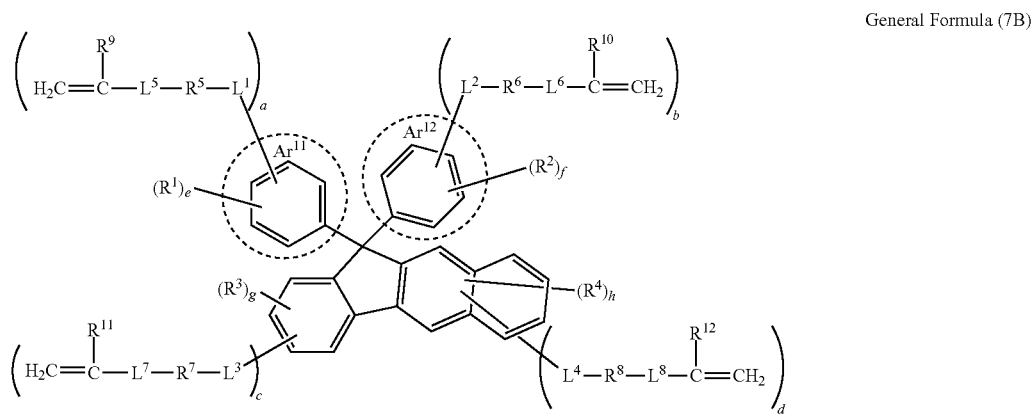

General Formula (8B)

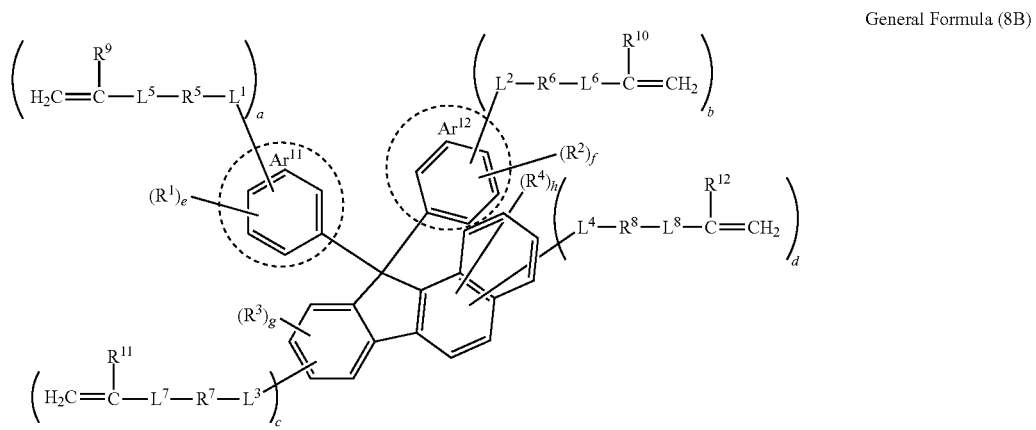

General Formula (9B)

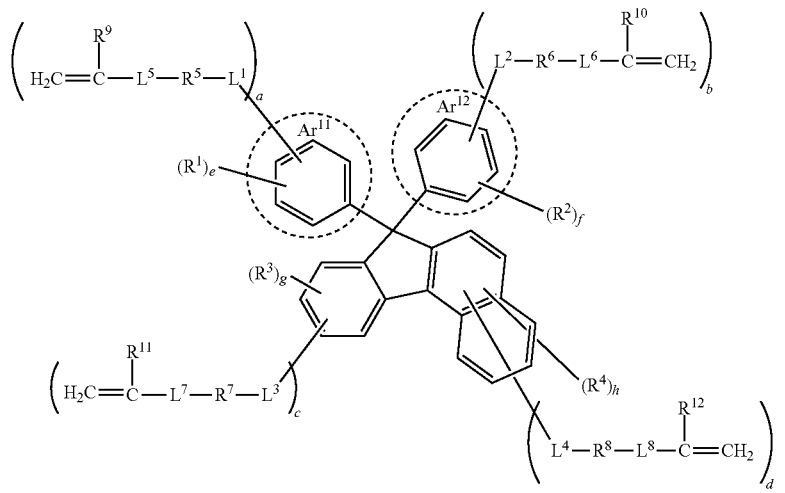

In the general formulae (6B), (7B), (8B) and (9B), $Ar^{11}$ and $Ar^{12}$ each independently represent an aryl or heteroaryl group containing the benzene ring surrounded by the broken line, and at least one of $Ar^{11}$ and $Ar^{12}$ is an aromatic condensed ring group containing the benzene ring surrounded by the broken line as one condensed ring therein. $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen' atom or a methyl group. a and b each independently indicate an integer of from 1 to 5, and c and d each independently indicate an integer of from 0 to 5. $R^1$ to $R^4$ each independently represent a substituent, e, f, g and h each independently indicate an integer of 0 or more. However, in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

In the general formulae (6B), (7B), (8B) and (9B), the preferred range of $R^1$ to $R^{12}$ is the same as the preferred range of $R^1$ to $R^{12}$ in the general formulae (6B), (7B), (8B) and (9B).

In the general formulae (6B), (7B), (8) and (9B), the preferred range of $L^1$ to $L^8$ is the same as the preferred range of $L^1$ to $L^4$ in the general formulae (6) to (9).

In the general formulae (6B), (7B), (8B) and (9B), the preferred range of a and b is the same as the preferred range of a and b in the general formulae (6) to (9).

In the general formulae (6B), (7B), (8B) and (9B), the preferred range of c and d is the same as the preferred range of c and d in the general formulae (6) to (9).

In the general formulae (6B), (7B), (8B) and (9B), the preferred range of e, f, g and h is the same as the preferred range of e, f, g and h in the general formulae (6) to (9).

The condensed ring-containing compound represented by the general formula (6) is preferably represented by the general formula (6A) or (6B), more preferably (6A).

The condensed ring-containing compound represented by the general formula (7) is preferably represented by the general formula (7A) or (7B), more preferably (7B).

The condensed ring-containing compound represented by the general formula (8) is preferably represented by the general formula (8A) or (8B), more preferably (8A).

The condensed ring-containing compound represented by the general formula (9) is preferably represented by the general formula (9A) or (9B), more preferably (9A).

The condensed ring-containing compound represented by the general formulae (6) to (9) is preferably represented by any of the general formulae (6A), (7A), (8A), (9A), (6B), (7B), (8B) and (9B) from the viewpoint of improving lens moldability, more preferably by any of the general formulae (6A), (6B), (7B), (8B) or (9B) from the viewpoint of increasing the refractivity and reducing the Abbe's number, even more preferably by any of (6B), (7B), (8B) or (9B) from the viewpoint of increasing more the refractivity and reducing more the Abbe's number.

The condensed ring-containing compound represented by the general formula (1) is preferably any of the following Xa-4 to Xa-15.

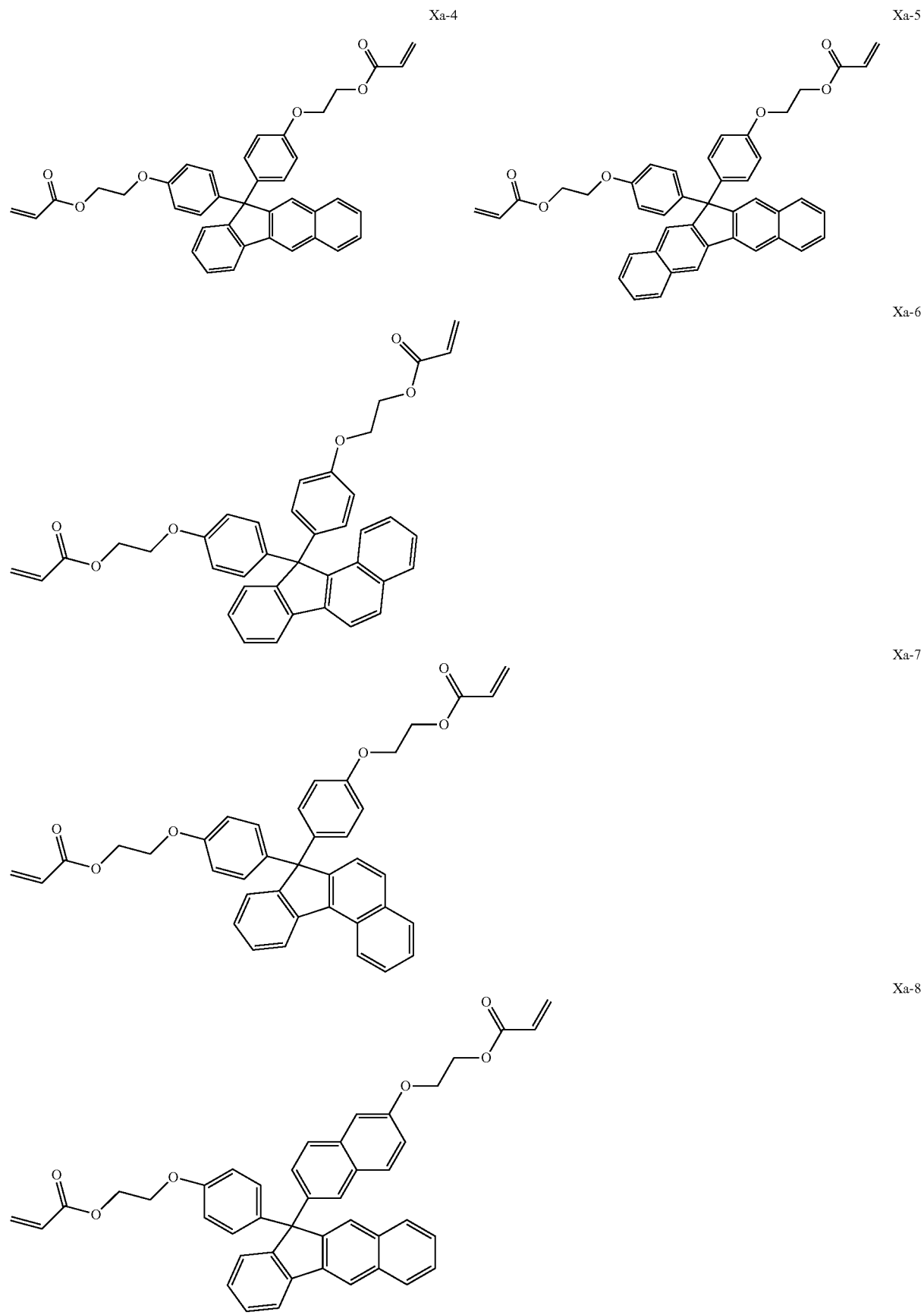

-continued
Xa-9
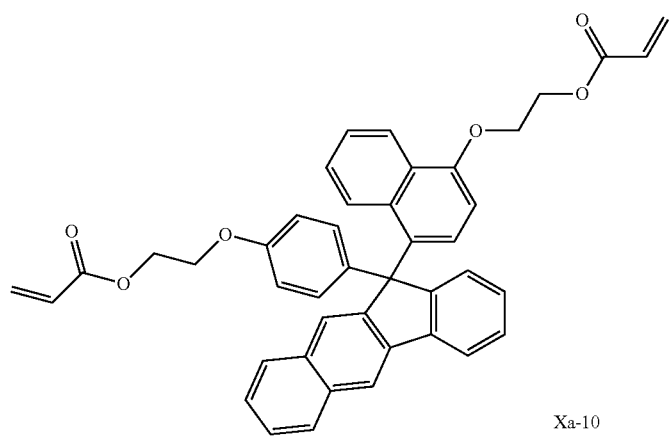
Xa-10
Xa-11
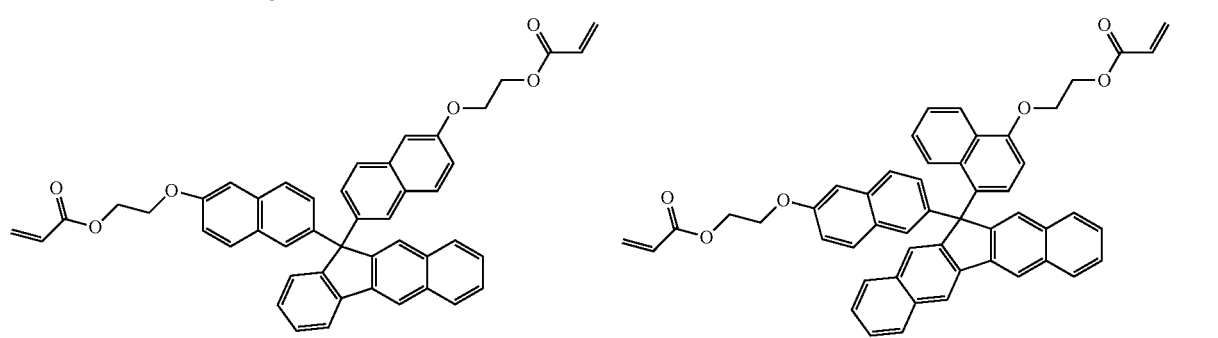
Xa-12
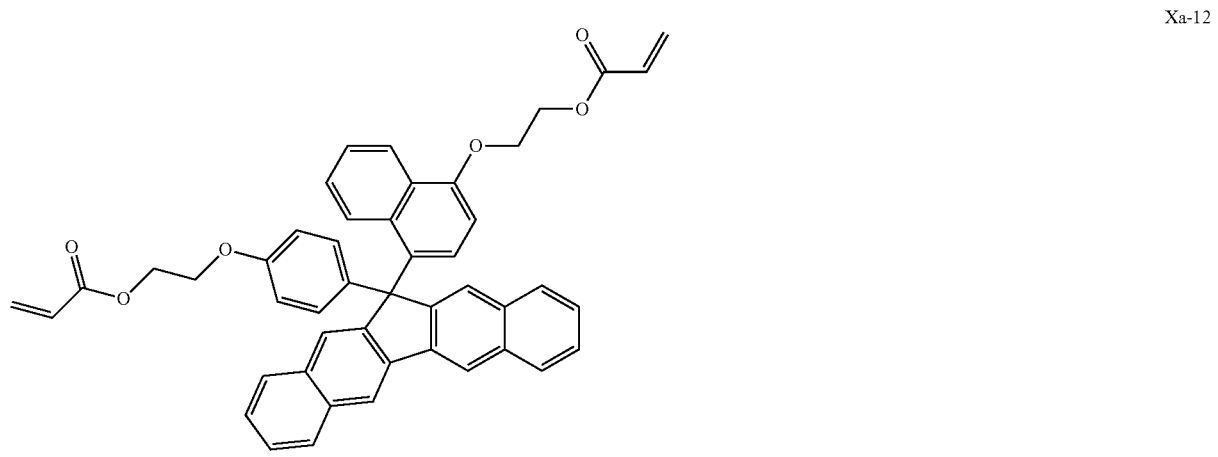
Xa-13
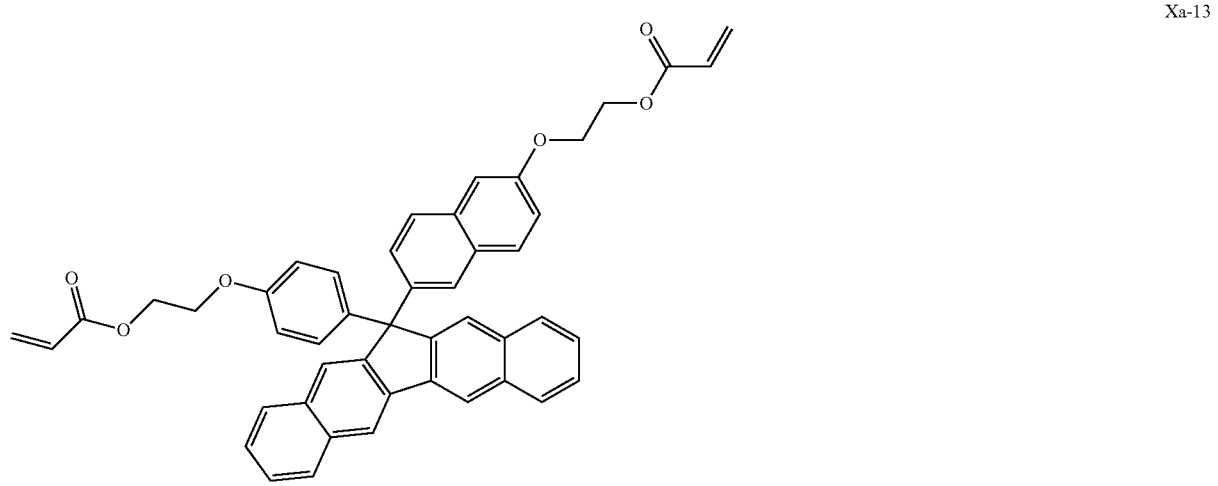

Xa-14
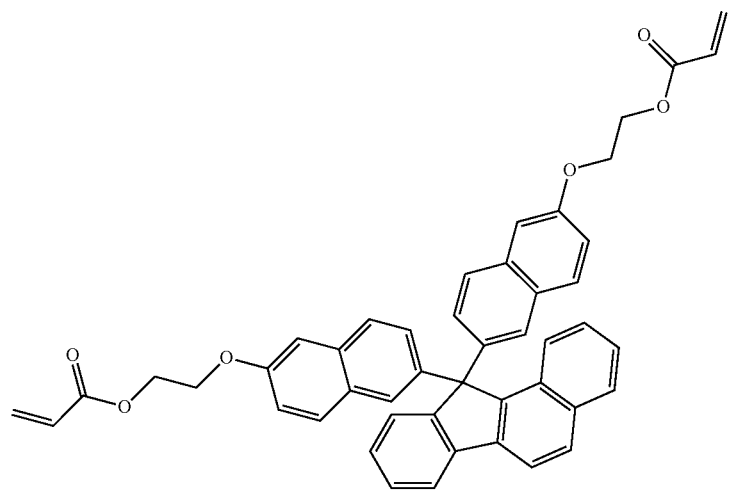
Xa-15
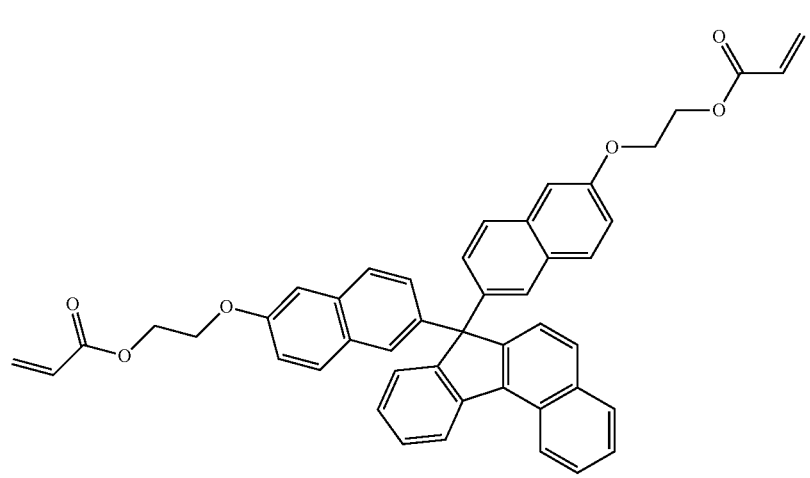
In the following, specific examples of the condensed ring-containing compound represented by the general formula (1), which are preferred for use in the present invention, are listed below. However, the present invention is not limited to the following compounds.
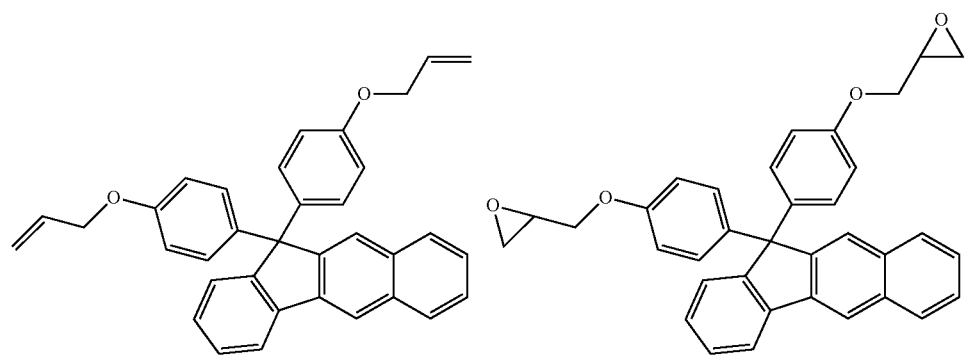

-continued
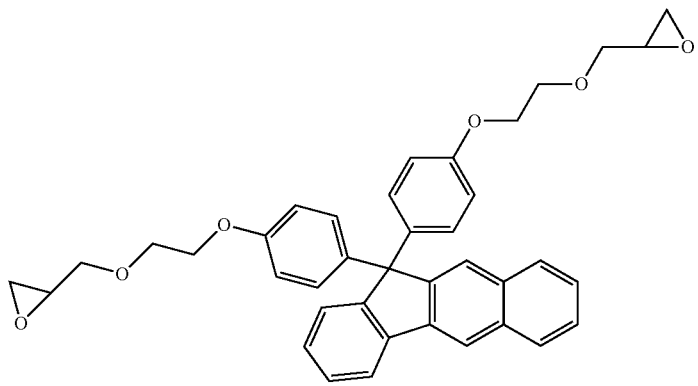
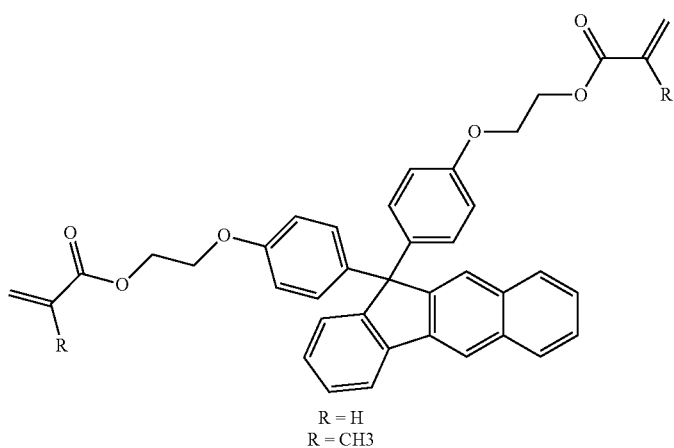
R = H
R = CH3
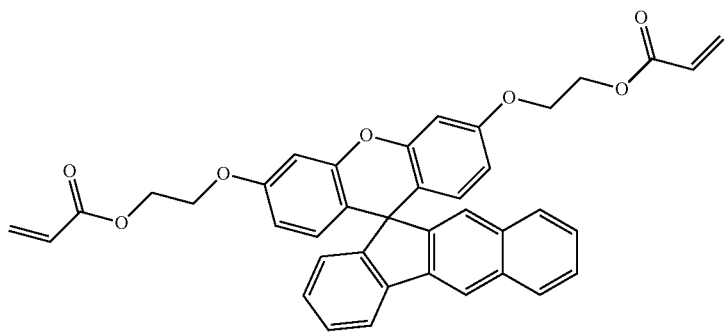
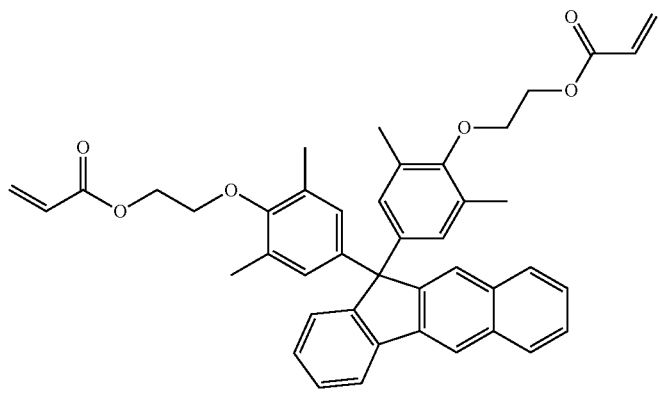

-continued
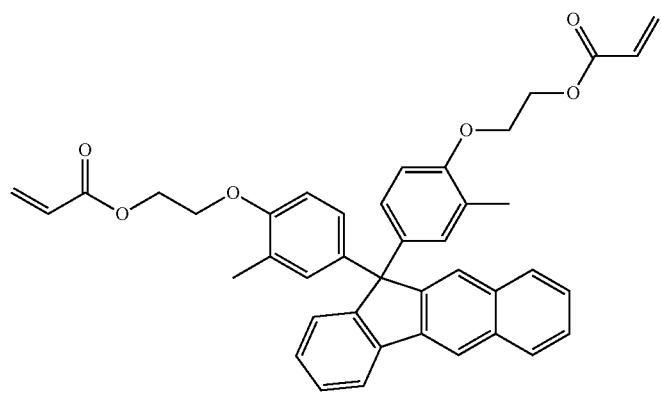
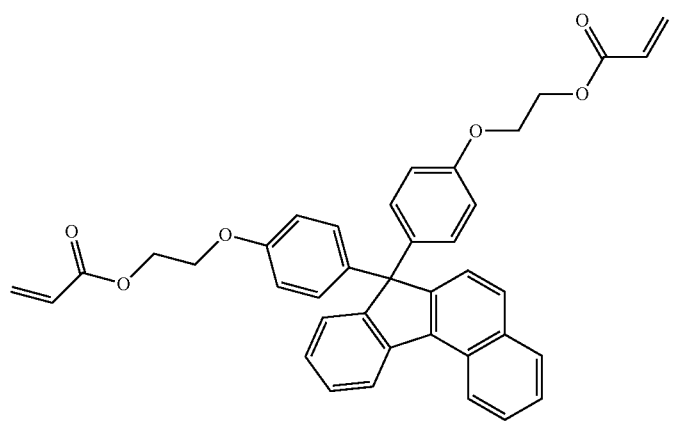
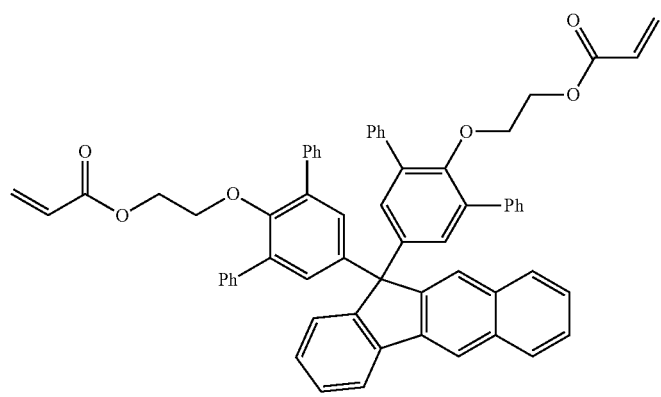
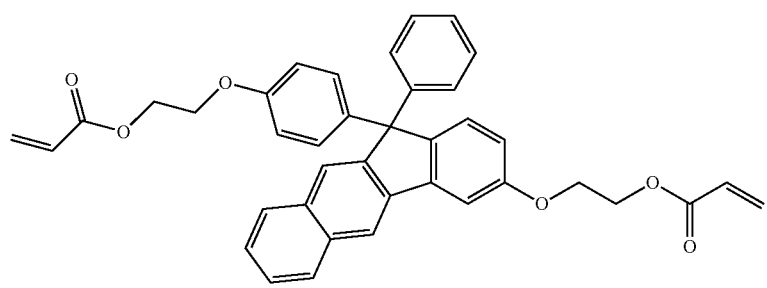

-continued
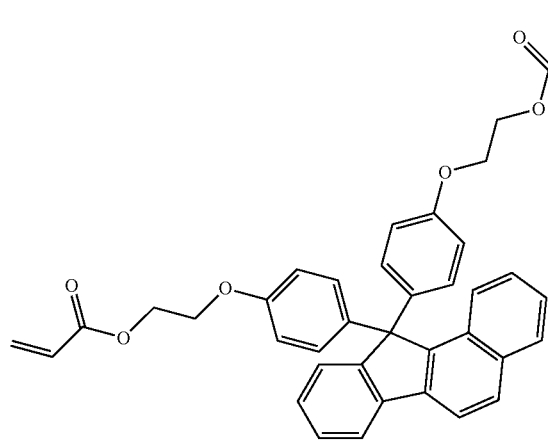
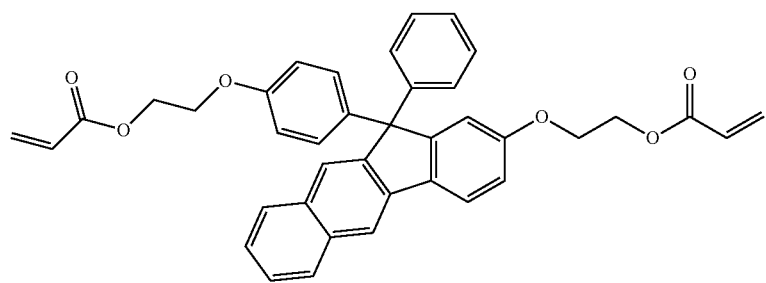
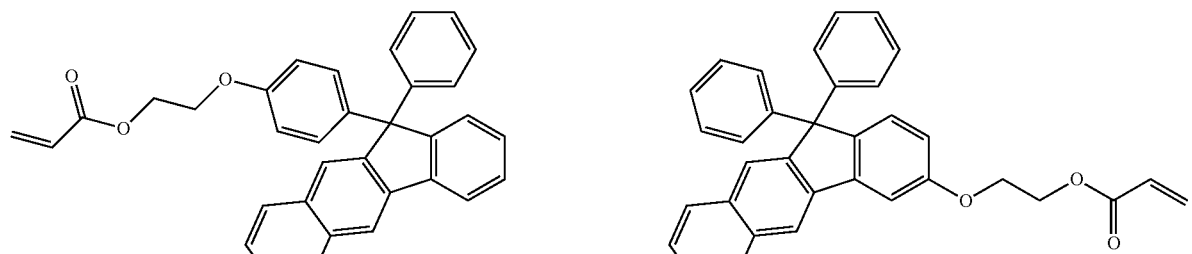
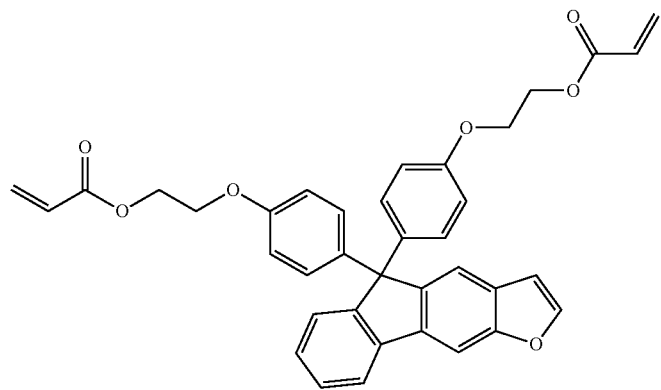

-continued
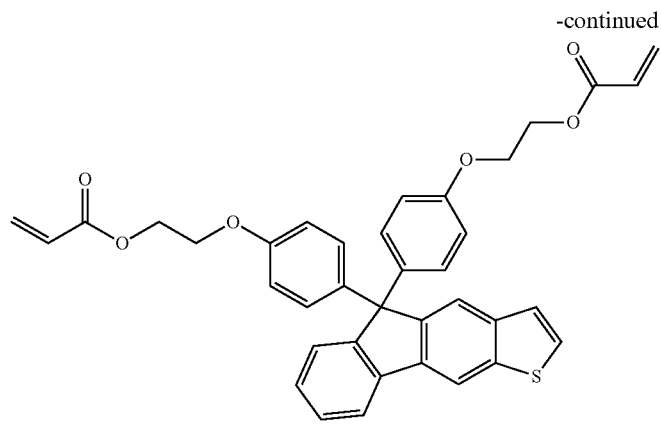
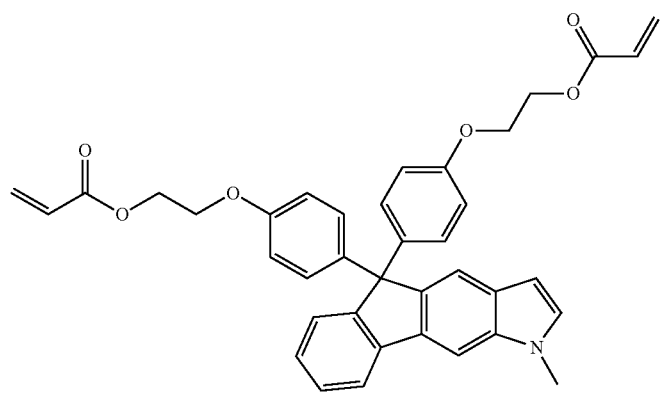
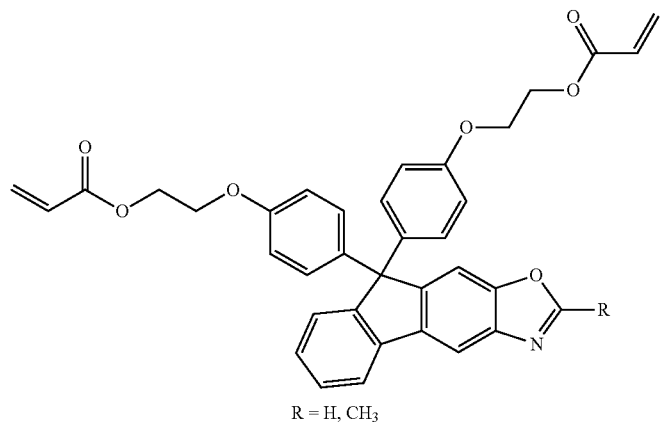
R = H, CH₃
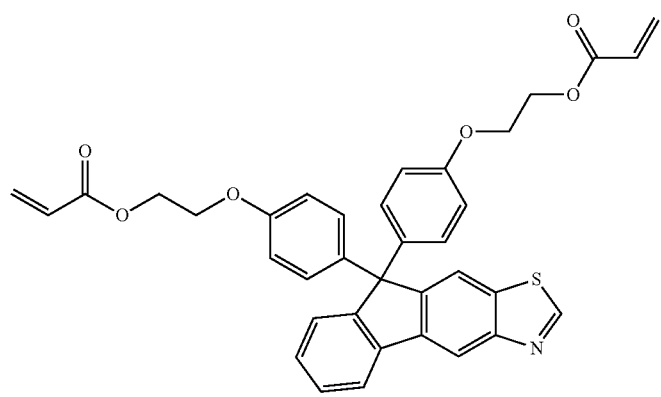

-continued
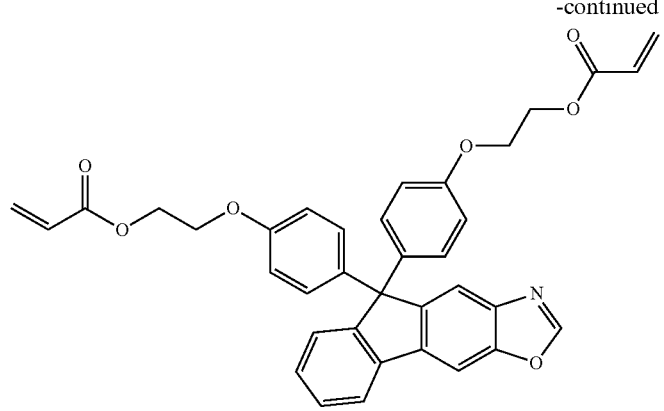
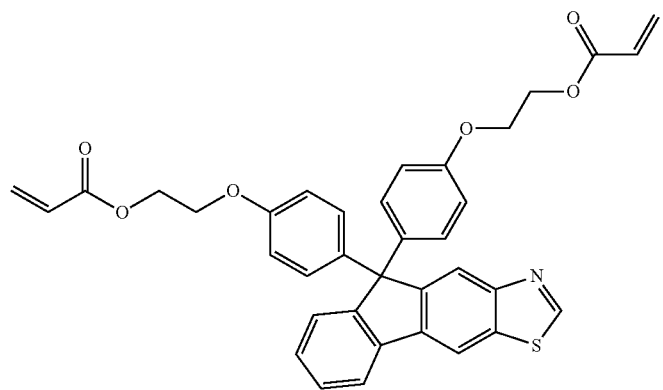
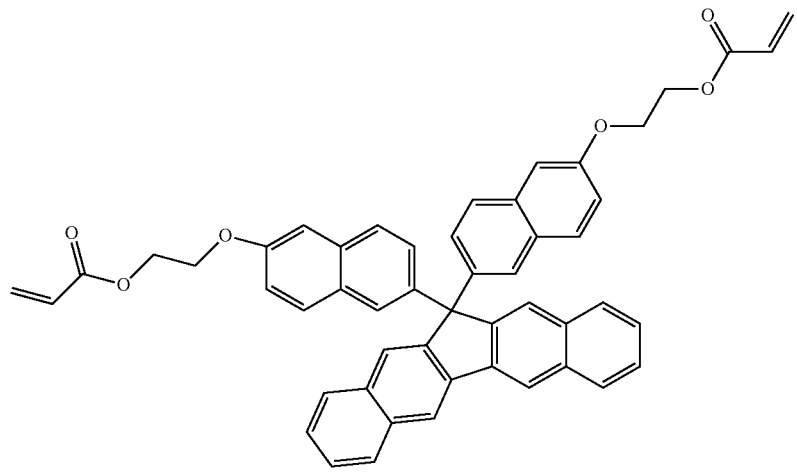
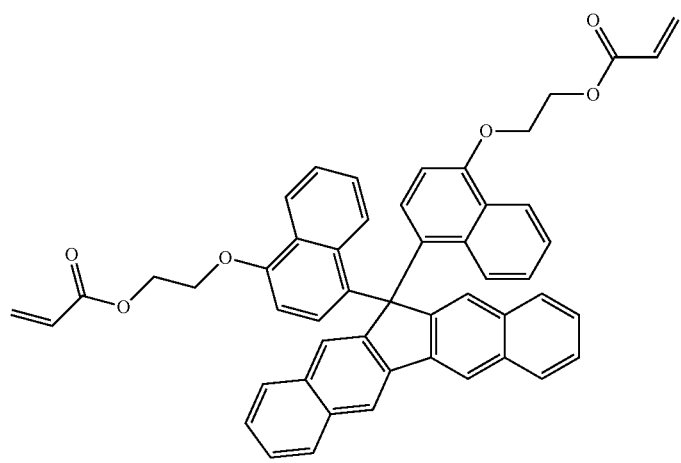

-continued
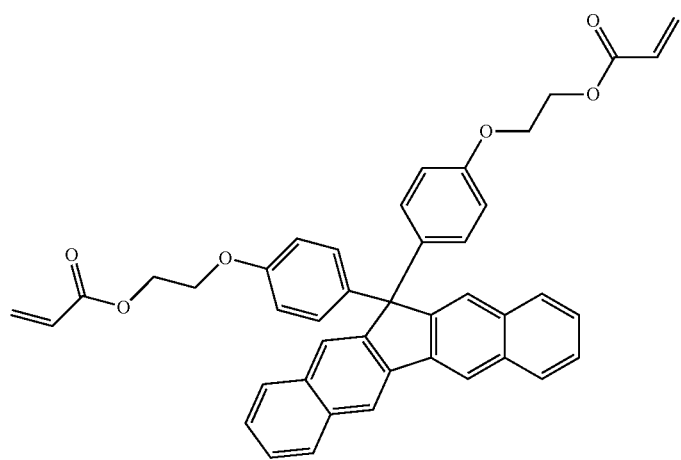
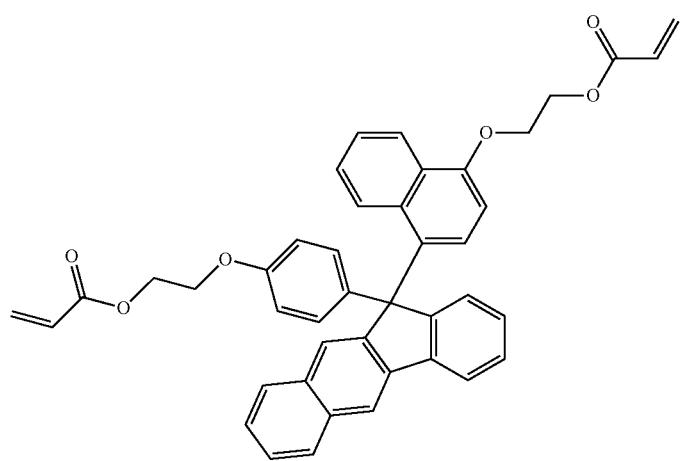
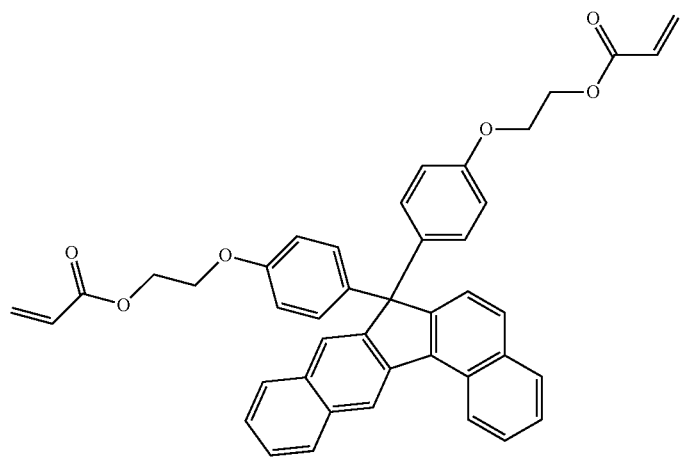

-continued
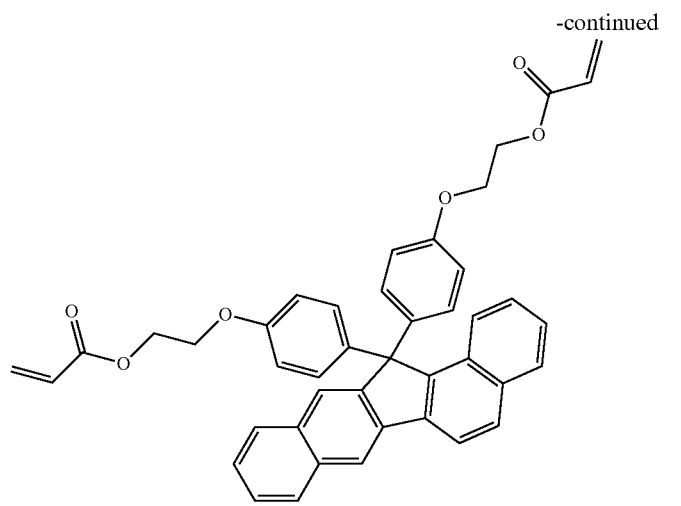
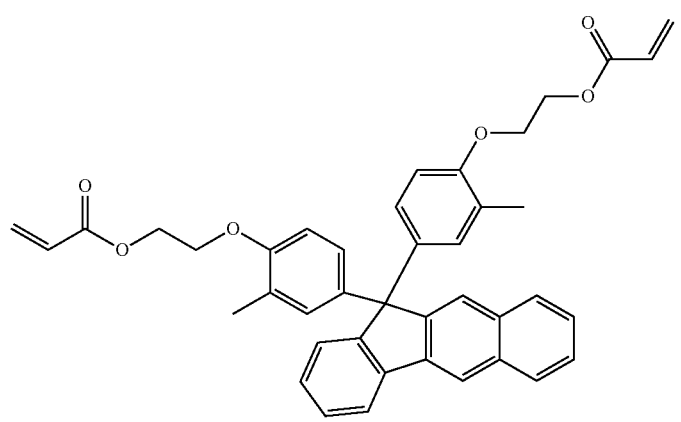
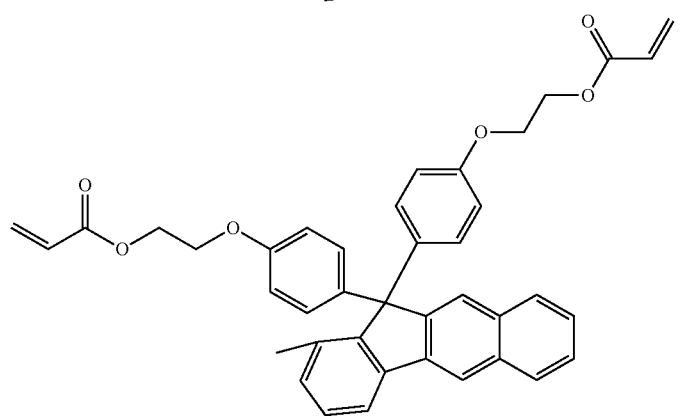
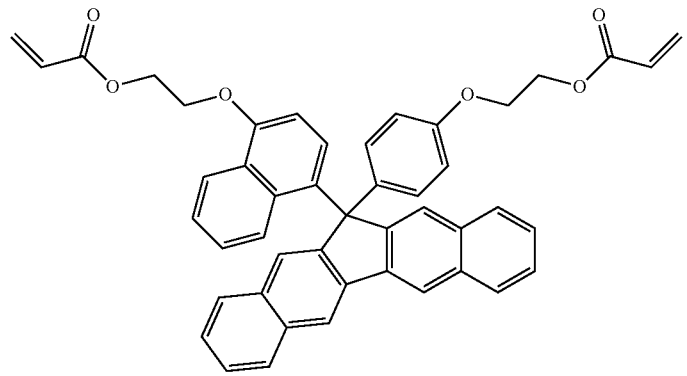

-continued
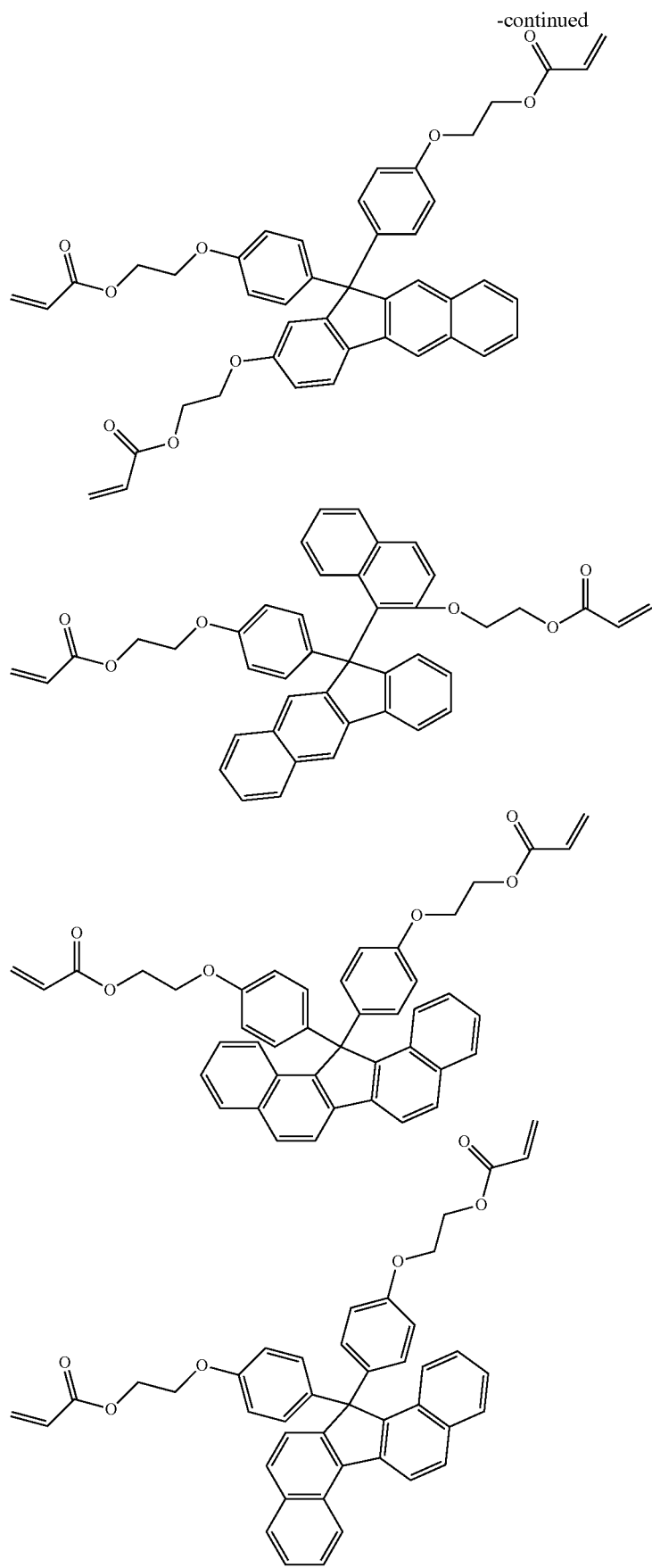

-continued
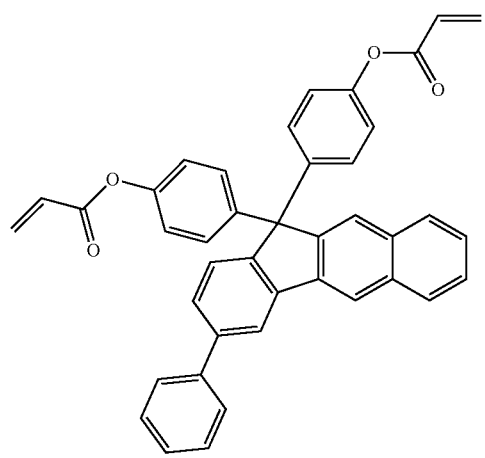
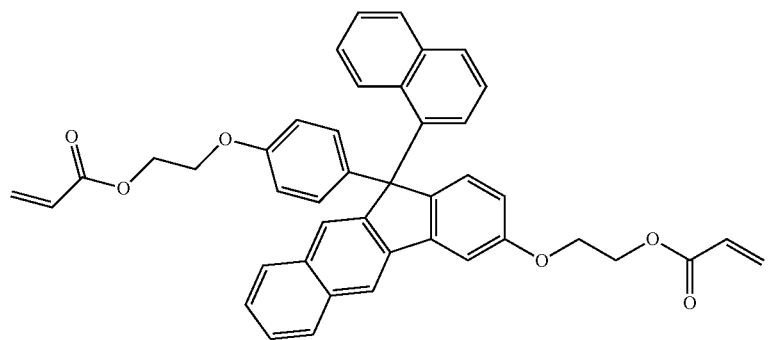
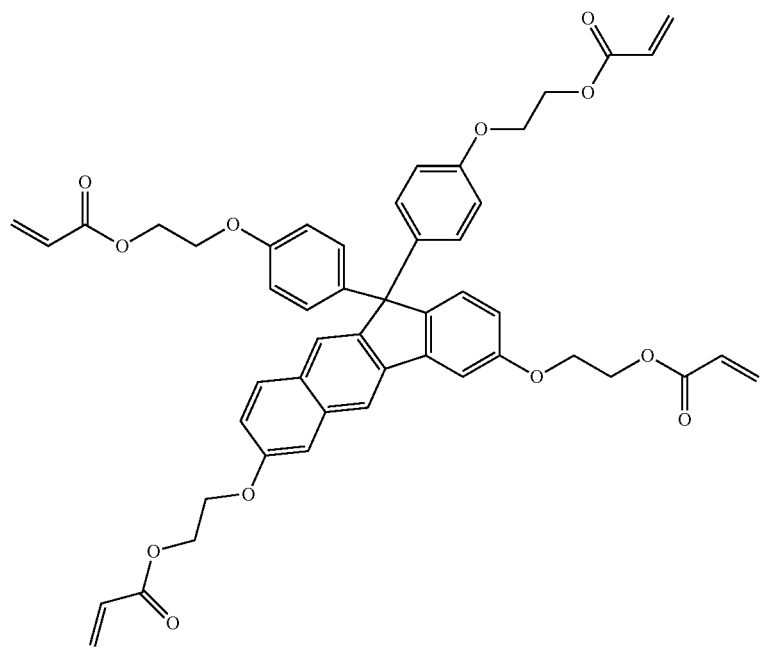

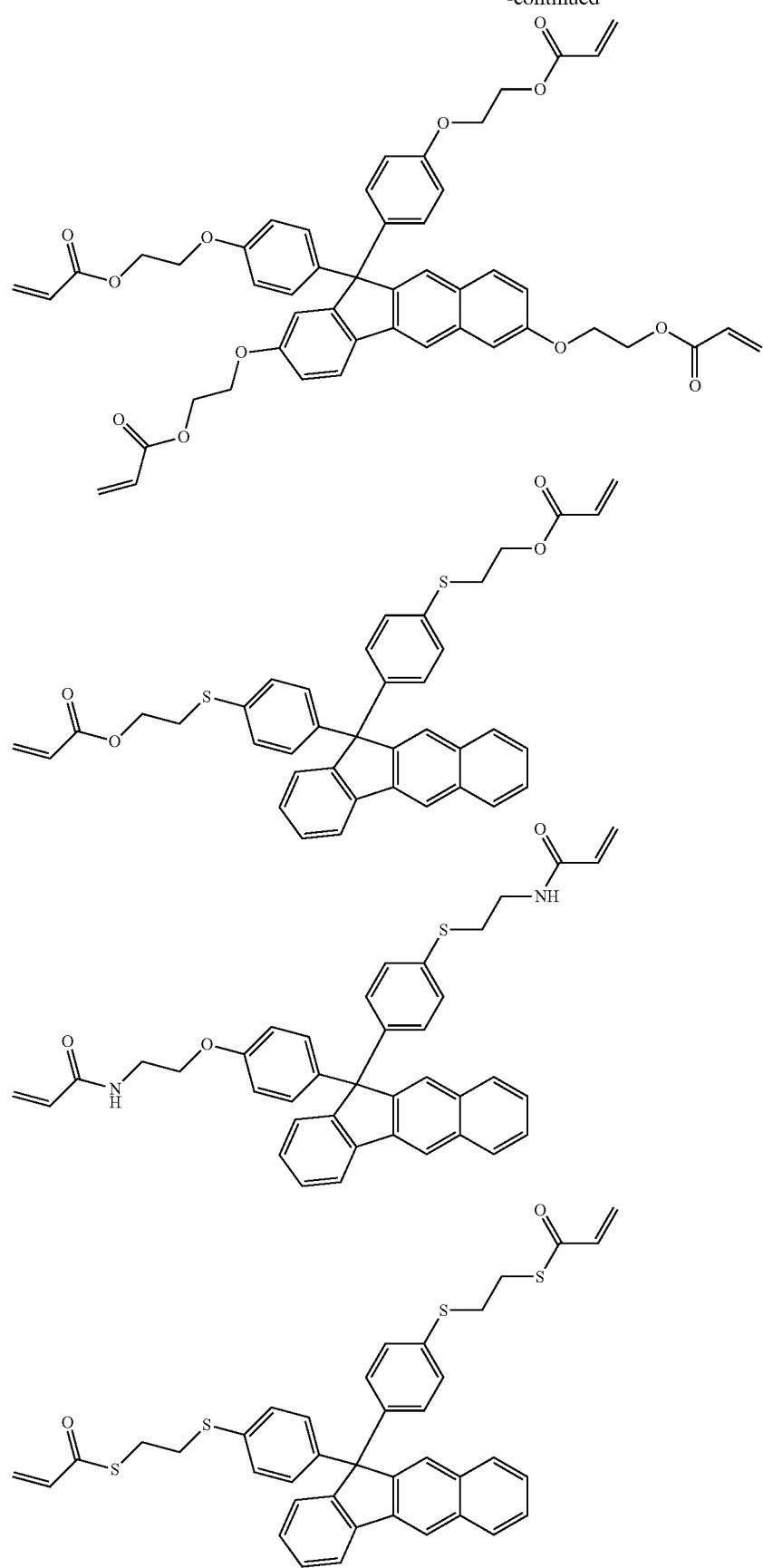

-continued
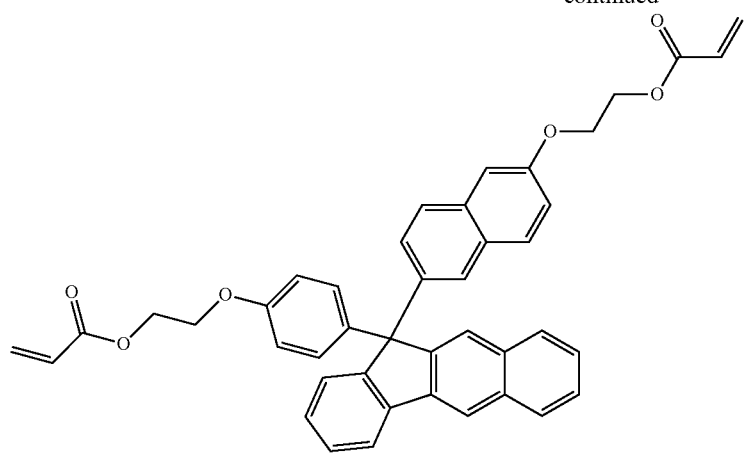
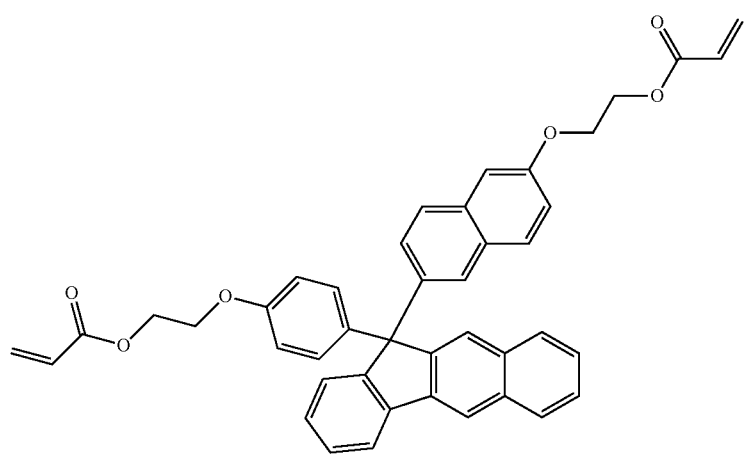
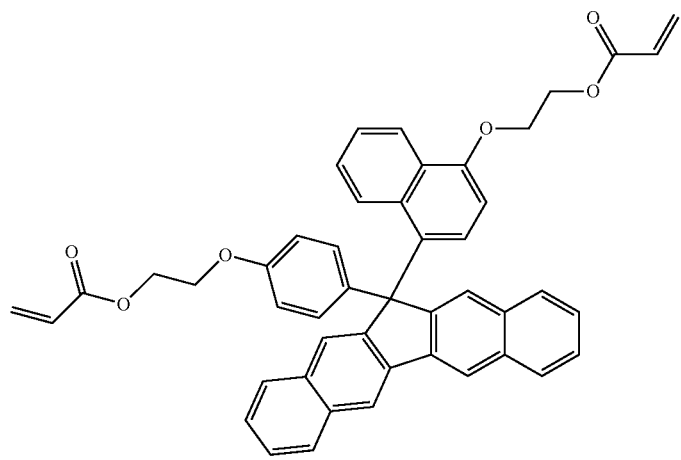

-continued
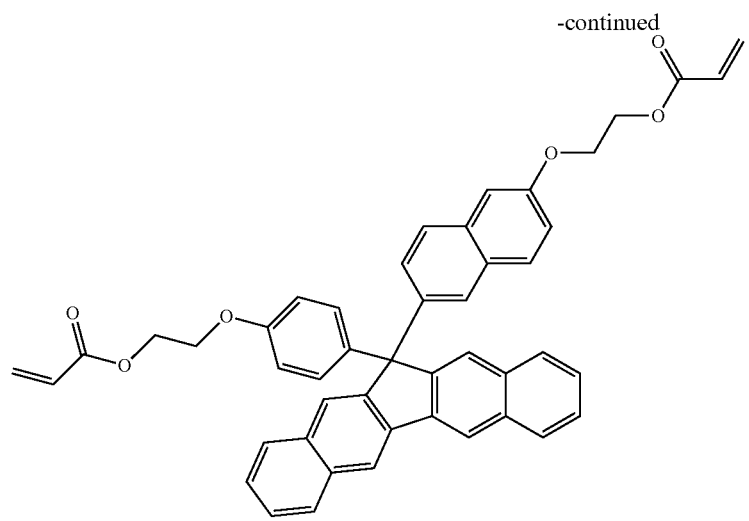
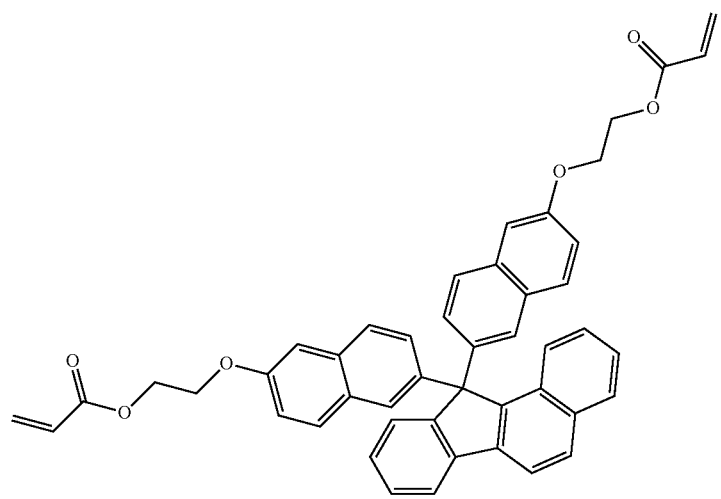
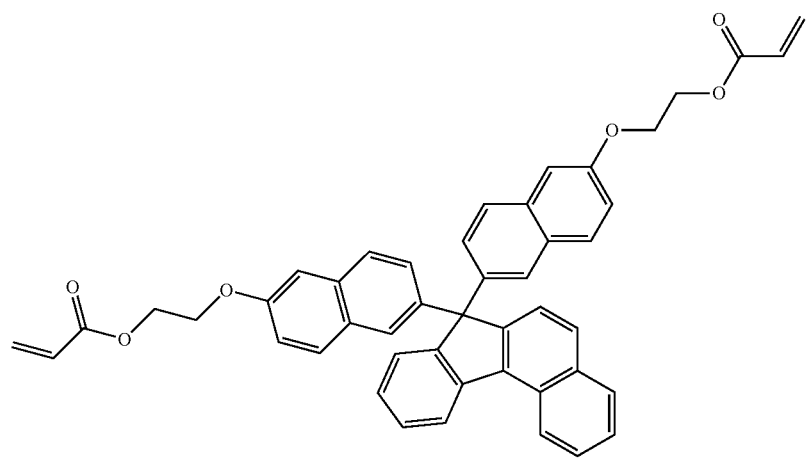

-continued

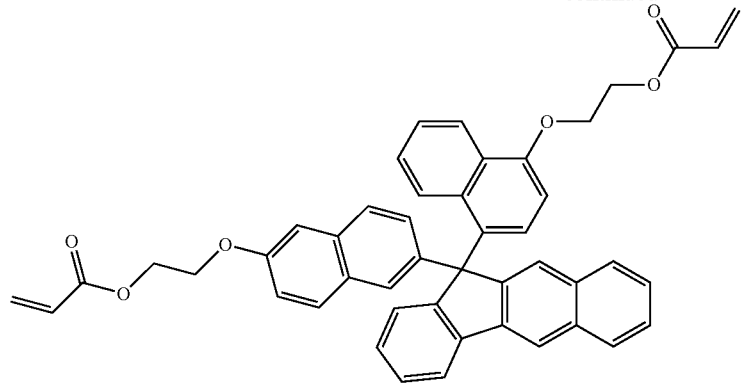

(Molecular Weight)

The molecular weight of the condensed ring-containing compound represented by the general formula (1) preferred for use in the present invention is preferably from 400 to 1000, more preferably from 400 to 700, even more preferably from 500 to 650.

(Method for Obtainment)

The method for obtaining the condensed ring-containing compound represented by the general formula (1) is not specifically defined, and the compound may be commercially available or may be produced through synthesis.

In a case of producing the compound through synthesis, the method for producing the condensed ring-containing compound represented by the general formula (1) is not specifically defined and the compound may be produced in any known method. For example, the compound may be produced according to the method described in JP-A 2011-68624.

Preferably, the curable resin composition contains the condensed ring-containing compound represented by the general formula (1) in an amount of from 40 to 80% by mass relative to the total amount of the curable resin composition, more preferably from 50 to 85% by mass, even more preferably from 60 to 75% by mass.

<Non-Conjugated Vinylidene Group-Containing Compound>

The curable resin composition of the present invention contains a non-conjugated vinylidene group-containing compound represented by the following general formula (2).

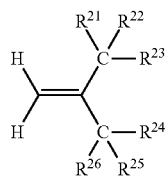

General Formula (2)

In the general formula (2), $R^{21}$ to $R^{26}$ each independently represent a substituent, at least one of $R^{21}$ to $R^{26}$ forms a ring, or at least two bond to each other to form a ring.

However, the non-conjugated vinylidene group-containing compound represented by the general formula (2) does not include a (meth)acrylate monomer.

Using a curable resin composition that contains the non-conjugated vinylidene group-containing compound represented by the general formula (2), the present invention makes it possible to control the viscosity of the semi-cured product after photo- or thermal-polymerization to fall within a specific range and makes it possible to better and increase the heat resistance and the good rate of the cured product to be produced through thermal polymerization of the semi-cured product according to the production method for a cured product of the present invention to be mentioned below.

In the general formula (2), the substituent to be represented by $R^{21}$ to $R^{26}$ is not specifically defined, for which, for example, usable are the following substituents: a hydrogen atom, a halogen atom, a halogenoalkyl group, an alkyl group, an alkenyl group, an acyl group, a hydroxyl group, a hydroxyalkyl group, an aromatic group, a heteroaromatic group, an alicyclic group.

Of those, preferably, $R^{21}$ to $R^{26}$ each are independently a substituent composed of hydrogen, oxygen and carbon atoms alone, more preferably a substituent composed of hydrogen and carbon atoms alone. Concretely, $R^{21}$ to $R^{26}$ each are preferably a hydrogen atom, an alkyl group or an alkenyl group, more preferably a hydrogen atom, an alkyl group having from 1 to 5 carbon atoms, or an alkenyl group having from 2 to 5 carbon atoms.

Regarding the expression of the group (atomic group) in this description, the group with no expression of substitution or unsubstitution is meant to include both an unsubstituted group and a substituted group. For example, "alkyl group" includes not only an alkyl group with no substituent (unsubstituted alkyl group) but also an alkyl group with a substituent (substituted alkyl group).

The ring that any of $R^{21}$ to $R^{26}$ forms may be an aromatic ring or a heteroaromatic ring, and may also be a nonaromatic ring. Above all, the ring to be formed by $R^{21}$ to $R^{26}$ is preferably a nonaromatic ring, more preferably a nonaromatic hydrocarbon ring. The ring to be formed by $R^{21}$ to $R^{26}$ may further have a substituent on the ring, and for example, the substituent is preferably an alkyl group having from 1 to 5 carbon atoms, more preferably a methyl group, an ethyl group, an n-propyl group or an isopropyl group. In case where the ring to be formed by $R^{21}$ to $R^{26}$ has additional substituents on the ring, the substituents may bond to each other to form a condensed ring.

The non-conjugated vinylidene group-containing compound represented by the general formula (2) may have one ring or multiple rings formed by $R^{21}$ to $R^{26}$ therein. In case where the compound has multiple rings formed by $R^{21}$ to $R^{26}$, the rings may be multiple rings independent of each other, or those independent multiple rings may be condensed to form a condensed ring, or in case where one ring has additional substituents, the substituents may bond to each other to form a condensed ring. Above all, the ring to be formed by $R^{21}$ to $R^{26}$ is more preferably a condensed ring formed through condensation of multiple rings; and in case where one ring has additional substituents, more preferably, the substituents bond to each other to form a condensed ring. In this description, an embodiment where two rings form spiro-condensation like the specific compounds mentioned below is also within the scope of the concept of the condensed ring here.

Of the carbon atom to which $R^{21}$ and $R^{22}$ bond and the carbon atom to which $R^{25}$ and $R^{26}$ bond, one carbon atom is preferably an asymmetric carbon atom.

Preferably, the non-conjugated vinylidene group-containing compound represented by the general formula (2) contains a condensed ring formed through condensation of from 2 to 5 rings, more preferably a condensed ring formed through condensation of 2 or 3 rings.

Preferably, the number of the ring-constituting atoms of the condensed ring is from 3 to 10, more preferably from 3 to 9, even more preferably from 4 to 9.

Of $R^{21}$ to $R^{26}$, (A) at least one forms a ring, or (B) at least two bond to each other to form a ring. Of $R^{21}$ to $R^{26}$ in the non-conjugated vinylidene group-containing compound, preferred is the case (B) where at least two bond to each other to form a ring. More preferred embodiments of the non-conjugated vinylidene group-containing compound are described below, as divided in those two cases of (A) and (B).

First described is the case (A) where at least one of $R^{21}$ to $R^{26}$ forms a ring.

In the case (A), preferably, any two of $R^{21}$ to $R^{23}$ in those $R^{21}$ to $R^{26}$ bond to each other to form a ring, or any two of $R^{24}$ to $R^{26}$ bond to each other to form a ring. In this case, more preferably, any either alone of any two of $R^{21}$ to $R^{23}$ or any two of $R^{24}$ to $R^{26}$ bond to each other to form a ring, and in the case, more preferably, the others not bonding to each other and therefore not forming a ring of any two of $R^{21}$ to $R^{23}$ or any two of $R^{24}$ to $R^{26}$ bond are all hydrogen atoms (for example, in the case where any two of $R^{21}$ to $R^{23}$ bond to each other to form a ring, preferably, $R^{24}$ to $R^{26}$ are all hydrogen atoms).

Next, the case (B) where at least two of $R^{21}$ to $R^{26}$ bond to each other to form a ring is described.

In the case (B), preferably, the non-conjugated vinylidene group-containing compound is represented by the following general formula (2').

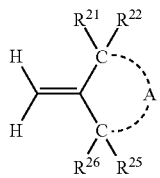

General Formula (2')

In the general formula (2'), $R^{21}$, $R^{22}$, $R^{25}$ and $R^{26}$ each independently represent a substituent, A represents an atomic group necessary for forming a cyclic structure.

In the general formula (2'), the preferred range of the substituent represented by $R^{21}$, $R^{25}$ and $R^{26}$ is the same as that by $R^{21}$ to $R^{26}$ mentioned above. $R^{21}$, $R^{22}$, $R^{25}$ and $R^{26}$ may bond to each other to form a ring, and the ring may additionally have a substituent.

Preferably, of the pair of $R^{21}$ and $R^{22}$ or the pair of $R^{25}$ and $R^{26}$, at least one of the two substituent in any one pair alone is a hydrogen atom, and more preferably, both the two substituents in any one pair alone are hydrogen atoms.

Also preferably, $R^{21}$ and $R^{22}$ are each independently a hydrogen atom or a hydrocarbon group having from 1 to 5 carbon atoms, and the hydrocarbon group having from 1 to 5 carbon atoms does not form a ring. Of $R^{21}$ and $R^{22}$, preferably, one alone is a hydrogen atom or a hydrocarbon group having from 1 to 5 carbon atoms, and the hydrocarbon group having from 1 to 5 carbon atoms does not form a ring.

In the general formula (2'), A represents an atomic group necessary for forming a cyclic structure, and the cyclic structure is not specifically defined and may be any known cyclic structure. The cyclic structure includes, for example, an alicyclic ring (nonaromatic hydrocarbon ring), an aromatic ring, a hetero ring, a lactone ring containing —CO—, etc.

Of those, preferably, A is an atomic group necessary for forming an alicyclic ring having from 4 to 10 carbon atoms including the carbon atoms bonding to A in the general formula (2') and the carbon atom constituting the non-conjugated vinylidene group, and more preferably, A is an atomic group necessary for forming an alicyclic ring having from 5 to 9 carbon atoms including the carbon atoms bonding to A in the general formula (2') and the carbon atom constituting the non-conjugated vinylidene group. The alicyclic ring may have an additional substituent, and the preferred embodiments of the substituent are the same as those of the substituent that the ring to be formed by $R^{21}$, $R^{22}$, $R^{25}$ and $R^{26}$ may have. A may be an unsaturated alicyclic ring or a saturated alicyclic ring, but preferably, the non-conjugated vinylidene group-containing compound represented by the general formula (2') has at least one unsaturated bond as a whole. A may form a condensed ring along with the substituent represented by $R^{21}$, $R^{22}$, $R^{25}$ and $R^{26}$.

In the general formula (2') in the present invention, preferably, $R^{21}$, $R^{22}$, $R^{25}$ and $R^{26}$ each independently represent a substituent composed of hydrogen atoms and carbon atoms alone, and especially preferably, A represents an alicyclic (nonaromatic hydrocarbon) structure.

In the present invention, preferably, the non-conjugated vinylidene group-containing compound represented by the general formula (2) has any other alkenyl group in addition to the vinylidene group (non-conjugated vinylidene group). The position of the other vinylidene group than the non-conjugated vinylidene group in the non-conjugated vinylidene group-containing compound represented by the general formula (2) is not specifically defined. Preferably, however, the non-conjugated vinylidene group-containing compound represented by the general formula (2) has the other vinylidene group than the non-conjugated vinylidene group on the ring formed by $R^{21}$, $R^{22}$, $R^{25}$ and $R^{26}$. Specifically, the ring formed by $R^{21}$, $R^{22}$, $R^{25}$ and $R^{26}$ preferably includes at least one unsaturated hydrocarbon ring, and more preferably the ring includes at least one unsaturated hydrocarbon ring that has only one double bond.

Specific examples of the non-conjugated vinylidene group-containing compound represented by the general formula (2) and preferably used in the invention are shown below, to which, however, the invention is not limited.

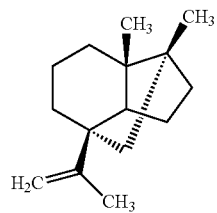

(B-1)

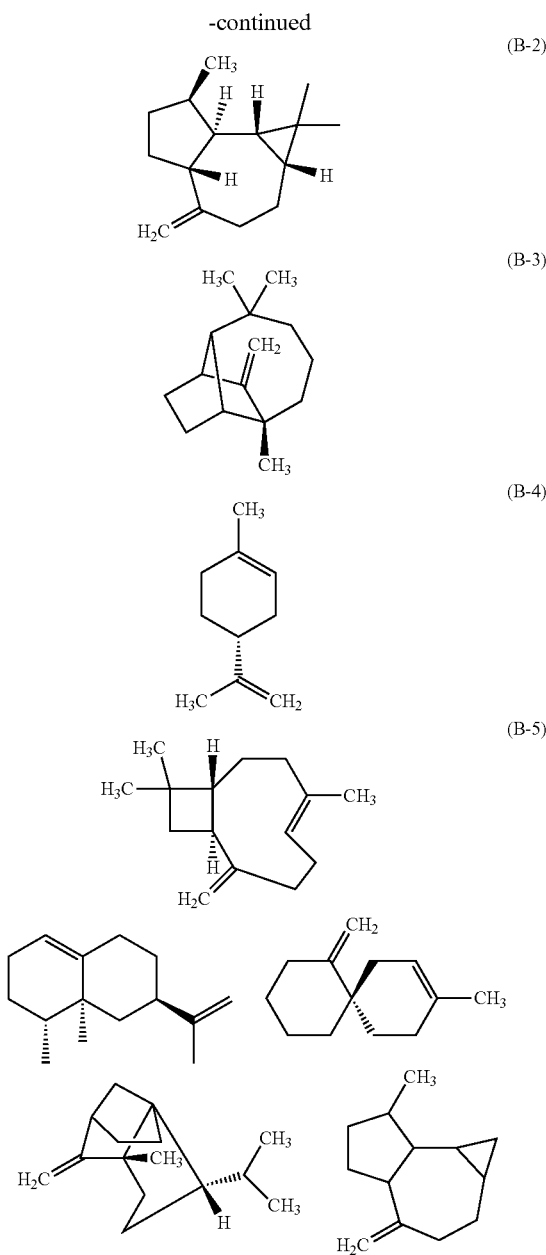

(Molecular Weight)

The molecular weight of the non-conjugated vinylidene group-containing compound represented by the general formula (2) is preferably from 100 to 400, more preferably from 120 to 350, even more preferably from 130 to 300.

(Method for Obtainment)

The method for obtaining the non-conjugated vinylidene group-containing compound represented by the general formula (2) is not specifically defined, and the compound may be commercially available or may be produced through synthesis.

In a case of commercially obtaining the compound, for example, β-caryophyllene of the compound (B-5) (by Tokyo Chemical Industry) is preferably used.

In a case of producing the compound through synthesis, the method for producing the non-conjugated vinylidene group-containing compound represented by the general formula (2) is not specifically defined and the compound may be produced in any known method. For example, of the non-conjugated vinylidene group-containing compound represented by the general formula (2), β-caryophyllene preferred for use in the invention may be produced according to the method described in J. Am. Chem. Soc. 85, 362 (1964), Tetrahedron Lette., 24, 1885 (1983), etc.

Preferably, the curable resin composition contains the non-conjugated vinylidene group-containing compound represented by the general formula (2) in an amount of from 0.5 to 30% by mass relative to the total amount of the curable resin composition, more preferably from 1 to 25% by mass, even more preferably from 2 to 20% by mass.

Preferably, the curable resin composition of the present invention contains the non-conjugated vinylidene group-containing compound represented by the general formula (2) in an amount of from 2 to 50% by mass relative to the condensed ring-containing compound represented by the general formula (1) therein, more preferably from 2 to 35% by mass, even more preferably from 2 to 20% by mass.

<Photoradical Polymerization Initiator>

Preferably, the curable resin composition of the present invention contains a photoradical polymerization initiator. Not specifically defined, the photoradical polymerization initiator may be any known photoradical polymerization initiator.

As the photoradical polymerization initiator, herein usable are the following compounds: Bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one. 1-hydroxycyclohexyl phenyl ketone, 1-(4-isopropylphenyl)-2-hydroxy-2-methylpropan-1-one, 1,2-diphenylethane-dione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-mehtylpropionyl)benzyl]phenyl}-2-methylpropan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenylphosphine oxide, bis(2,4,6-trimethylbenzoyl)phenylphosphine oxide.

Of the above, in the present invention, BASF's Irgacure 184 (1-hydroxycyclohexyl phenyl ketone), 1-[4-(2-hydroxyethoxy)-phenyl]-2-hydroxy-2-methyl-1-propan-1-one, 2-methyl-1-(4-methylthiophenyl)-2-morpholinopropan-1-one, and 2,2-dimethoxy-1,2-diphenylethan-1-one are preferred for the photoradical polymerization initiator.

Not specifically defined, the amount of the photoradical polymerization initiator in the curable resin composition is preferably from 0.01 to 5% by mass relative to the total amount of the curable resin composition, more preferably from 0.05 to 1.0% by mass, even more preferably from 0.05 to 0.5% by mass.

<Thermal Radical Polymerization Initiator>

The curable resin composition of the present invention preferably contains a thermal radical polymerization initiator. Since such a thermal radical polymerization initiator is previously added to the curable resin composition, the semi-cured product of the invention efficiently gives a cured product having high heat resistance of the invention through the subsequent thermal polymerization, or that is, the semi-cured product gives the cured product with good moldability, with ease and with high productivity.

The thermal radical polymerization initiator concretely includes the following compounds: 1,1-di(t-hexylpentyloxy)cyclohexane, 1,1-di(t-butylperoxy)cyclohexane, 2,2-di(4,4- di-(t-butylperoxy)cyclohexyl)propane, t-hexylperoxy-isopropyl monocarbonate, t-butylperoxy 3,5,5-trimethylhexanoate, t-butylperoxy laurate, dicumyl peroxide, di-t-butyl peroxide, t-butylperoxy 2-ethylhexanoate, t-hexylperoxy-2-ethylhexanoate, cumene hydroperoxide, t-butyl hydroperoxide, 2,3-dimethyl-2,3-diphenylbutane.

Above all, in the invention, preferred is use of a hydroperoxide-type thermal radical polymerization initiator having a hydroperoxide group in the molecule, as the thermal radical polymerization initiator, and more preferred is use of at least one hydroperoxide-type thermal radical polymerization initiator having a hydroperoxide group in the molecule and at least one of a non-hydroperoxide-type thermal radical polymerization initiator not having a hydroperoxide group in the molecule.

Especially for use in the invention, NOF's Perbutyl O (t-butylperoxy 2-ethylhexanoate) is preferred as the non-hydroperoxide-type thermal radical polymerization initiator, and NOF's Percumyl H (cumene hydroperoxide) is preferred as the hydroperoxide-type thermal radical polymerization initiator.

The reason why use of the hydroperoxide-type thermal radical polymerization initiator having a hydroperoxide group in the molecule is preferred is because the hydroperoxide-type thermal radical polymerization initiator has an effect of promoting chain transfer during polymerization of non-conjugated vinylidene group-containing compound monomer by which the three-dimensional structure of the resulting polymer can be more favorably controlled and the semi-cured product can be given good formability. In case where such a hydroperoxide-type thermal radical polymerization initiator is used, the temperature at which thermal radical polymerization is initiated is generally high, and therefore in such a case, it is more desirable that a non-hydroperoxide-type thermal radical polymerization initiator having a low thermal polymerization initiation temperature is low is used along with the hydroperoxide-type thermal radical polymerization initiator.

Not specifically defined, the amount of the thermal radical polymerization initiator to be in the curable resin composition is preferably from 0.01 to 5.0% by mass relative to the total of the condensed ring-containing compound represented by the general formula (1), the non-conjugated vinylidene group-containing compound represented by the general formula (2) and the polymer having a polymerizable group in the side chain thereof to be mentioned below, more preferably from 0.1 to 4.0% by mass, even more preferably from 0.3 to 3.0% by mass.

(Monofunctional (Meth)Acrylate Monomer)

Not contradictory to the intent and the spirit of the present invention, the curable resin composition of the present invention may contain any other monomer than the condensed ring-containing compound represented by the general formula (1), and preferably contains a monofunctional (meth)acrylate monomer.

The monofunctional (meth)acrylate monomer Usable in the present invention include, for example, the following: Adamantyl (meth)acrylates such as 1-adamantyl (meth)acrylate, etc.; norbornyl (meth)acrylates such as isobornyl (meth)acrylate, etc.; tricyclodecane (meth)acrylates such as tricyclo [5,2,1,0$^{2,6}$]dec-8-yl acrylate, etc.; 2-ethyl-2-butylpropanediol (meth)acrylate, 2-ethylhexyl (meth)acrylate, 2-ethylhexylcarbitol (meth)acrylate, 2-hydroxybutyl (meth)acrylate, 2-hydroxyethyl (meth)acrylate, 2-hydroxypropyl (meth)acrylate, 2-methoxyethyl (meth)acrylate, 3-methoxybutyl (meth)acrylate, 4-hydroxybutyl (meth)acrylate, benzyl (meth)acrylate, 1- or 2-naphthyl (meth)acrylate, butanediol mono(meth)acrylate, butoxyethyl (meth)acrylate, butyl (meth)acrylate, cetyl (meth)acrylate, EO-modified cresol (meth)acrylate, dipropylene glycol (meth)acrylate, ethoxylated phenyl (meth)acrylate, ethyl (meth)acrylate, isoamyl (meth)acrylate, isobutyl (meth)acrylate, isooctyl (meth)acrylate, cyclohexyl (meth)acrylate, dicyclopentanyl (meth)acrylate, dicyclopentanyloxyethyl (meth)acrylate, isomyristyl (meth)acrylate, lauryl (meth)acrylate, methoxydipropylene glycol (meth)acrylate, methoxytripropylene glycol (meth)acrylate, methoxypolyethylene glycol (meth)acrylate, methoxytriethylene glycol (meth)acrylate, methyl (meth)acrylate, neopentyl glycol benzoate (meth)acrylate, nonylphenoxypolyethylene glycol (meth)acrylate, nonylphenoxypolypropylene glycol (meth)acrylate, octyl (meth)acrylate, paracumylphenoxyethylene glycol (meth)acrylate, ECH-modified phenoxy (meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, stearyl (meth)acrylate, EO-modified succinic acid (meth)acrylate, tert-butyl (meth)acrylate, tribromophenyl (meth)acrylate, EO-modified tribromophenyl (meth)acrylate, tridodecyl (meth)acrylate.

Preferably, the curable resin composition of the present invention contains a monofunctional (meth)acrylate monomer having an aromatic ring among those monofunctional (meth)acrylate monomers.

As the monofunctional (meth)acrylate monomer having an aromatic ring for use in the present invention, for example, preferred are the following: Benzyl (meth)acrylate, 1- or 2-naphthyl (meth)acrylate, EO-modified cresol (meth)acrylate, ethoxylated phenyl (meth)acrylate, nonylphenoxypolyethylene glycol (meth)acrylate, nonylphenoxypolypropylene glycol (meth)acrylate, paracumylphenoxyethylene glycol (meth)acrylate, ECH-modified phenoxy (meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, tribromophenyl (meth)acrylate, EO-modified tribromophenyl (meth)acrylate, O-phenylphenol (meth)acrylate, O-phenylphenol EO-modified (meth)acrylate.

Of those, more preferred are benzyl (meth)acrylate, phenoxyethyl (meth)acrylate, O-phenylphenol (meth)acrylate, O-phenylphenol EO-modified (meth)acrylate; even more preferred are benzyl (meth)acrylate and phenoxyethyl (meth)acrylate; and more especially preferred are benzyl acrylate and phenoxyethyl acrylate.

(Compositional Ratio)

Preferably, the curable resin composition of the present invention contains a monofunctional (meth)acrylate monomer, in which the content of the monofunctional (meth)acrylate monomer is preferably from 10 to 80% by mass relative to the condensed ring-containing compound represented by the general formula (1), more preferably from 10 to 70% by mass, even more preferably from 15 to 65% by mass.

<Other Additives>

Not contradictory to the intent and the spirit of the present invention, the curable resin composition of the present invention may contain additives such as polymer, any other monomer, dispersant, plasticizer, thermal stabilizer, lubricant and others.

For example, the composition may contain a non(meth)acrylic monomer as the other monomer component.

Preferably, the amount of the non(meth)acrylic monomer to be in the composition is from 0 to 20% by mass in all the monomers therein, more preferably from 0 to 15% by mass.

Not specifically defined, the non(meth)acrylic monomer includes, for example, the following compounds.

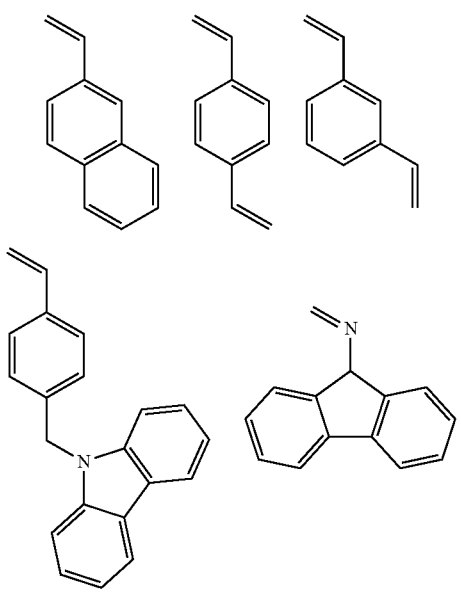

In addition, as a resin not satisfying the requirements for the present invention, the composition may further contain a polymer having a polymerizable group in the side chain thereof.

The polymer having a polymerizable group in the side chain thereof may be a homopolymer or a copolymer, and the copolymer may be one in which at least one copolymer component contains a polymerizable group in the side chain thereof.

Specific examples of the polymer having a polymerizable group in the side chain thereof are listed below.

Ra and Rb each independently represent a hydrogen atom or an alkyl group.

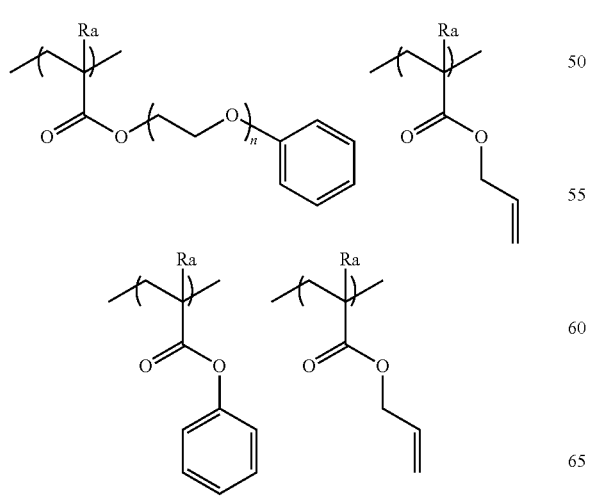

-continued

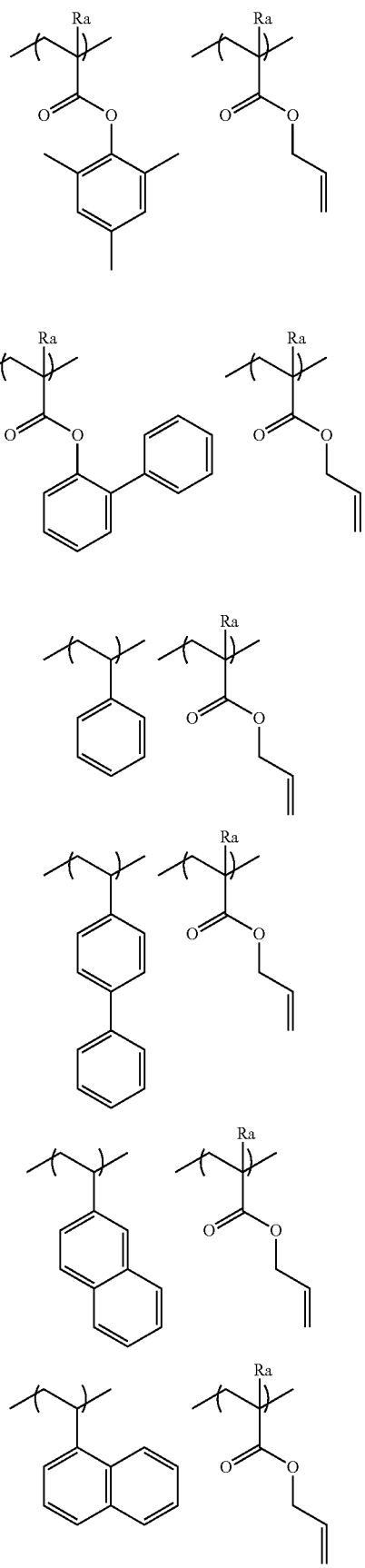

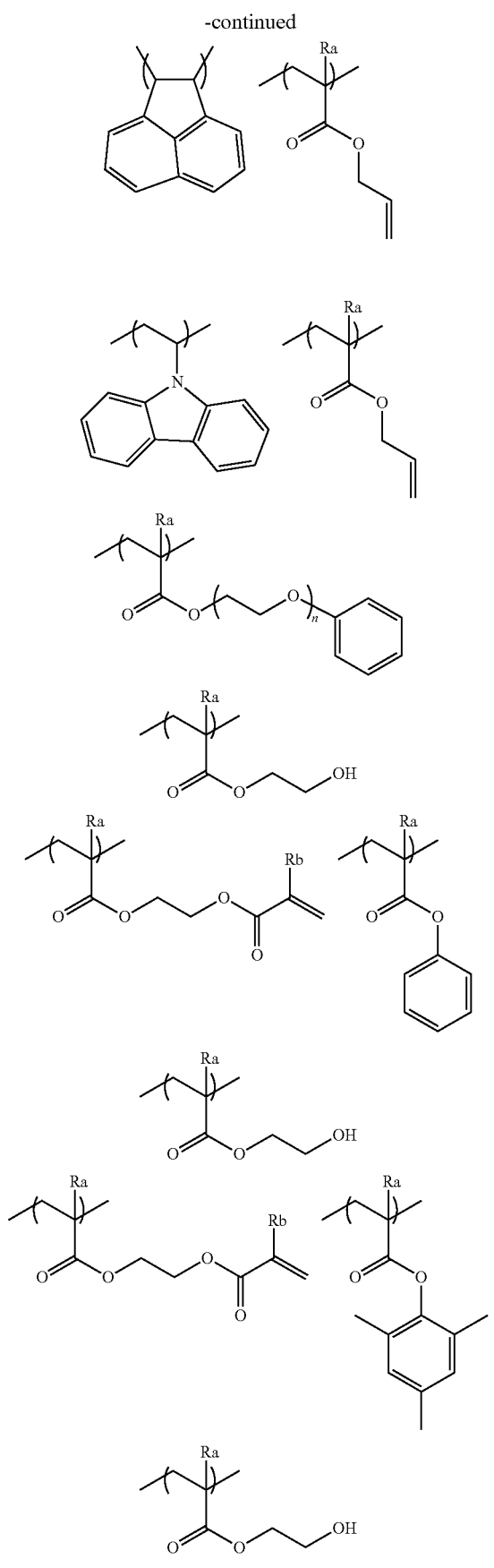
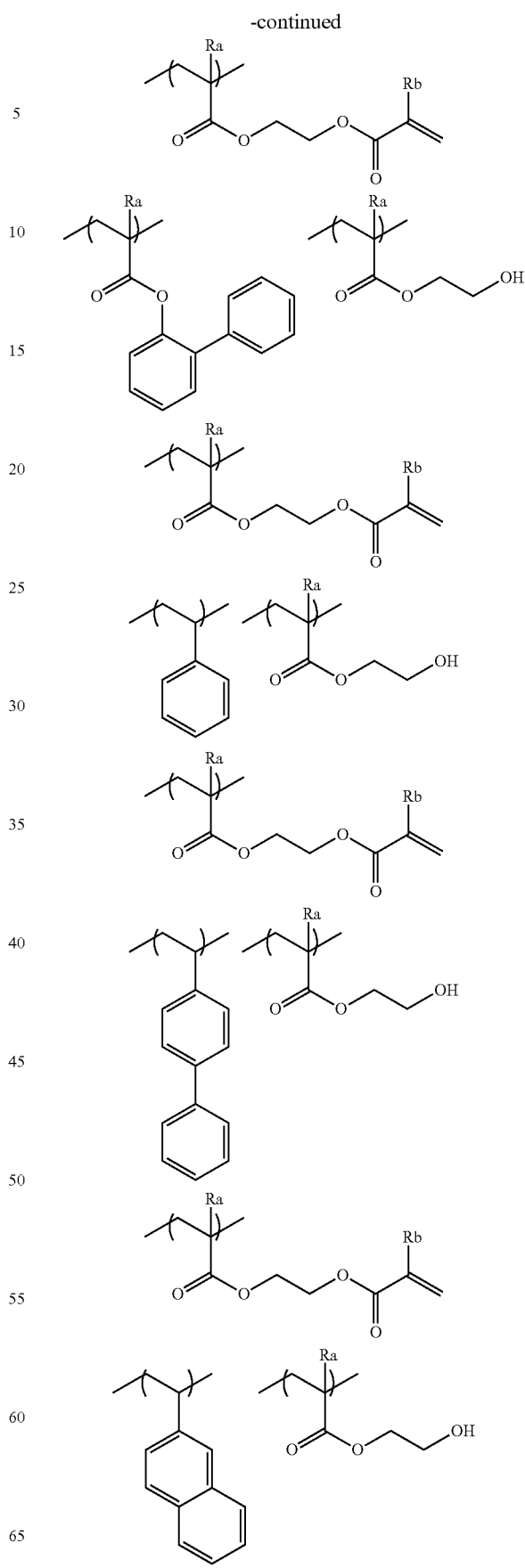

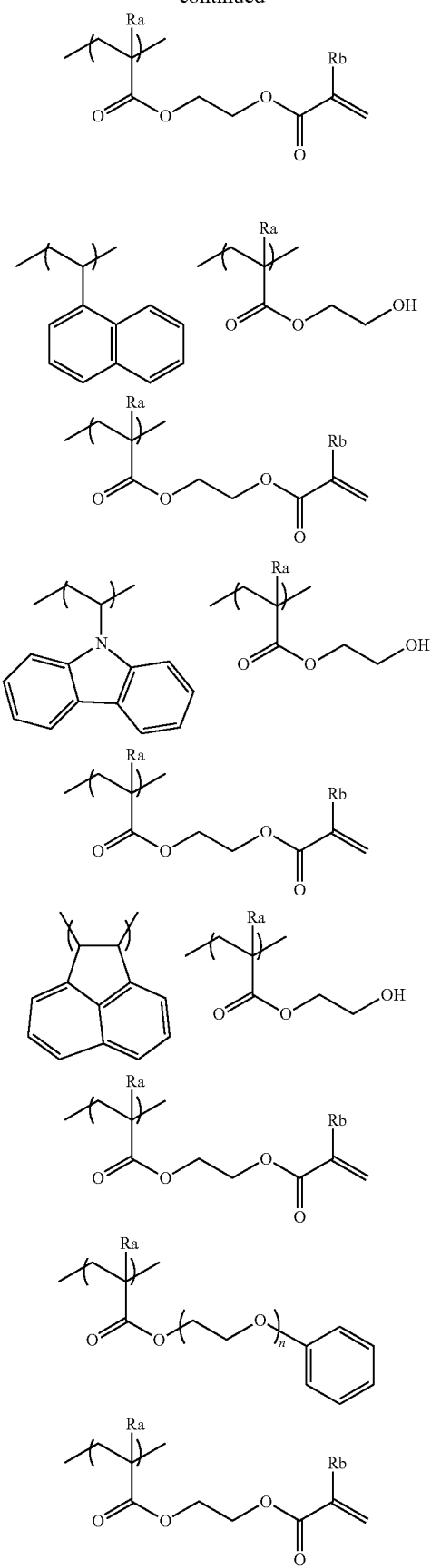
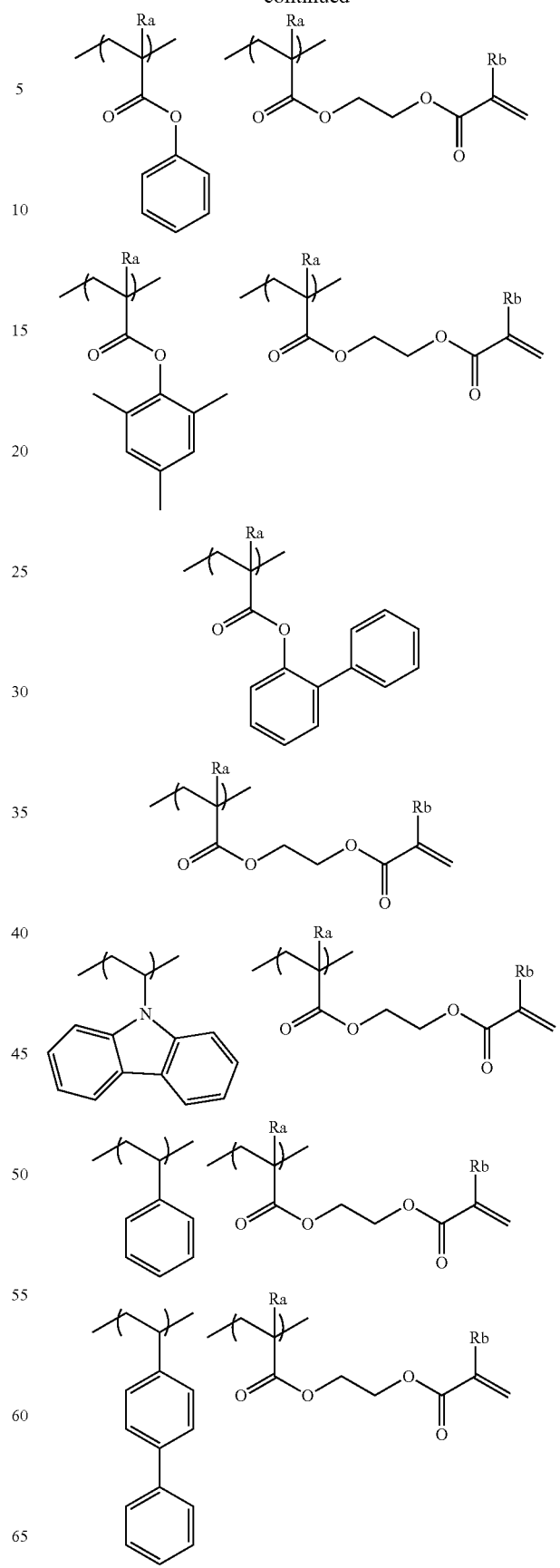

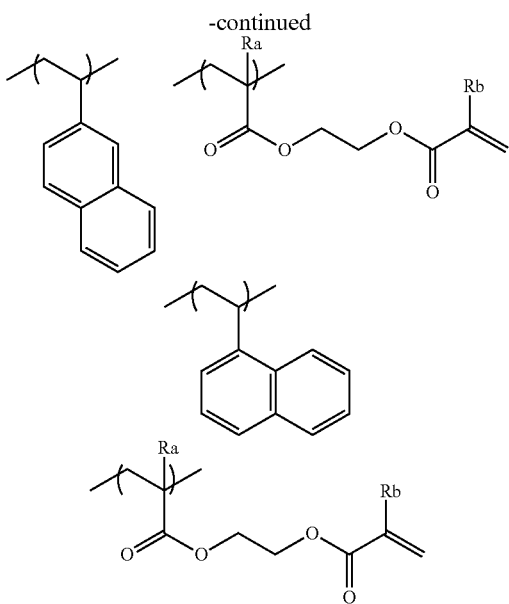

The molecular weight of the polymer having a polymerizable group in the side chain thereof is preferably from 1000 to 10000000, more preferably from 5000 to 300000, even more preferably from 10000 to 200000.

The glass transition temperature (hereinafter this may be referred to also as Tg) of the polymer having a polymerizable group in the side chain thereof is preferably from 50 to 400° C., more preferably from 70 to 350° C., even more preferably from 100 to 300° C.

[Production Method for Semi-Cured Product]

The production method for a semi-cured product of the invention includes a step of curing the curable resin composition of the present invention. The step of curing the curable resin composition of the present invention includes photoirradiation and heating.

Preferably, the production method for a semi-cured product of the present invention includes a step of photoirradiating the curable resin composition of the present invention.

Preferably in the production method for a semi-cured product of the present invention, the curable resin composition of the present invention is processed through at least any one of photoirradiation and heating to give a semi-cured product having a complex viscosity of from $10^5$ to $10^8$ mPa·s at 25° C. and at a frequency of 10 Hz, and more preferably, the curable resin composition of the present invention is photoirradiated to give a semi-cured product having a complex viscosity of from $10^5$ to $10^8$ mPa·s at 25° C. and at a frequency of 10 Hz.

Also preferably, in the step of photoirradiating the curable resin composition, the radical polymerization initiator further contains a photoradical polymerization initiator.

Here in this description, "semi-cured product" is one produced by polymerizing a curable resin composition, which, however, is not completely solid but has some flowability. For example, a photo and/or thermal polymer of a curable resin composition in such a state that its complex viscosity is from $10^5$ to $10^8$ mPa·s at 25° C. and at a frequency of 10 Hz is a semi-cured product. Not specifically defining the invention, those of which the upper limit of the complex viscosity at 25° C. and at a frequency of 10 Hz is up to $1.0 \times 10^9$ mPa·s are considered to fall within a range of semi-cured products. On the other hand, "cured product" is one produced by polymerizing a curable resin composition and is completely solid.

Regarding the production method for a semi-cured product of the present invention and the production method for a cured product of the present invention, the present invention is described concretely with reference to preferred embodiments thereof. The method for producing a cured product of the present invention includes the production method for a semi-cured product of the present invention, and therefore preferred embodiments of the production method common to both the two are described in the section of the description of the production method for a semi-cured product of the present invention.

<Semi-Curing Step>

The production method for a semi-cured product of the present invention preferably includes a step of photoirradiating and/or heating the curable resin composition to give a semi-cured product having a complex viscosity of from $10^5$ to $10^8$ mPa·s at 25° C. and at a frequency of 10 Hz.

In the production method for a semi-cured product of the invention, the curable resin composition may be directly set in the forming die to be used in thermal polymerization in the production method for a cured product of the invention to be mentioned below, before photoirradiation and/or heating of the composition, or alternatively, the curable resin composition may be set in a die different from the forming die and processed therein by photoirradiation and/or heating to give a semi-cured product, and thereafter the thus-photoirradiated, semi-cured product obtained in the production method for a cured product of the invention to be mentioned below, may be moved into the forming die.

Here, the forming die is generally composed of two die parts and is so designed that the content therein could be heated under pressure by the combination of the two die parts. When a low-viscosity composition is injected onto the forming die of the type, then the composition may leak out through the die clearance. The curable resin composition to be used in the production method for a semi-cured product of the invention generally has a low viscosity and therefore it would be difficult to directly inject the composition into a forming die. Consequently, in one preferred embodiment of the production method for a semi-cured product of the invention, a polymer having a polymerizable group in the side chain thereof is further added to the curable resin composition to control the Viscosity of the composition, as described above, and the composition is injected into a forming die in which it is semi-cured through photoirradiation and/or heating therein and is additionally processed for thermal polymerization therein to give a cured product in one and the same mold. This embodiment is preferred here from the viewpoint of the productivity of the product.

On the other hand, according to another preferred embodiment of the production method for a semi-cured product of the invention, the curable resin composition is put into a die different from the forming die, and is photoirradiated and/or heated therein to give a semi-cured product, and thereafter the semi-cured product is transferred into the forming die for polymerization therein to give a cured product, and this embodiment is preferred from the viewpoint of reducing the material cost.

In case where a die different from a forming die is used, preferred is use of a die for preform. The die for preform may be formed of metal, or may be formed of glass or resin. In consideration of using the die repeatedly in a mass-production line, the die for preform is preferably formed of metal or glass. In case where the semi-cured product of the invention is used for lenses, it is desirable that at least one side of the die for preform has a shape that is the same as and/or similar to the shape of the forming die, and more preferably, both sides of the die have a shape that is the same as and/or similar to the shape of the forming die.
(Condition of Photoirradiation)

Preferred conditions of photoirradiation in the production method for a semi-cured product of the invention are described below.

Preferably, the photoirradiation is carried out so that the semi-cured product after photoirradiation could have a complex viscosity of from $10^5$ to $10^8$ mPa·s at 25° C. and at a frequency of 10 Hz, more preferably from $10^5$, to $10^{7.5}$ mPa·s, even more preferably from $10^{5.5}$ to $10^{7.5}$ mPa·s.

Preferably, the light for photoirradiation is UV ray or visible ray, more preferably UV ray. For example, favorably used are metal halide lamp, low-pressure mercury lamp, high-pressure mercury lamp, ultra-high-pressure mercury lamp, bactericidal lamp, xenon lamp, LED lamp, etc.

The atmosphere in photoirradiation is preferably in air or after purging with an inert gas; and more preferred is an atmosphere purged with nitrogen to have an oxygen concentration of at most 1%.
(Condition for Semi-Curing by Heating)

Preferred conditions for thermal semi-curing in the production method for a semi-cured product of the invention are described below.

Preferably, the thermal semi-curing is attained so that the semi-cured product after heating could have a complex viscosity of from $10^5$ to $10^8$ mPa·s at 25° C. and at a frequency of 10 Hz, more preferably from $10^5$ to $10^{7.5}$ mPa·s, even more preferably from $10^{5.5}$ to $10^{7.5}$ mPa·s.
[Semi-Cured Product]

The semi-cured product of the invention is one produced according to the semi-cured product production method of the invention. The semi-cured product is favorably used in the production method for a cured product of the invention to be mentioned below.

Here, the preferred range of the complex viscosity of the semi-cured product of the present invention is the same as the preferred range of the complex viscosity of the semi-cured product in the above-mentioned production method for a semi-cured product of the present invention.

The semi-cured product of the invention may not contain the photoradical polymerization initiator at all after the photoirradiation step, since the initiator is completely consumed in the step, or the photoradical polymerization initiator may remain in the semi-cured product.
(Tg)

Preferably, the glass transition temperature (hereinafter this may be referred to as Tg) of the semi-cured product of the invention is preferably from −150 to 0° C., more preferably from −50 to 0° C., even more preferably from −20 to 0° C.
[Production Method for Cured Product]

The production method for a cured product of the present invention includes a thermal polymerization step of putting the semi-cured product of the present invention in a forming die for pressure formation therein, and heating it therein for thermal polymerization to give a cured product.

Preferably, the production method for a cured product of the present invention contains a step of processing the curable resin composition containing a condensed ring-containing compound represented by the general formula (1), a non-conjugated vinylidene group-containing compound represented by the general formula (2), and at least one of a thermal or optical radical polymerization initiator, for at least one of photoirradiation and heating to give a semi-cured product having a complex viscosity of from $10^5$ to $10^8$ mPa·s at 25° C. and at a frequency of 10 Hz, and a thermal polymerization step of putting the semi-cured product in a forming die for pressure formation therein, and heating it therein for thermal polymerization to give a cured product. (However, when the method includes the step of photoirradiating the curable resin composition, then it is more desirable that the radical polymerization initiator further contains a photoradical polymerization initiator.)

Even when the step of producing the semi-cured product does not includes a step of photoirradiating the curable resin composition, the radical polymerization initiator may further contain a photoradical polymerization initiator.

Preferably, the production method for a cured product of the present invention includes a step of photoirradiating the curable resin composition, and the radical polymerization initiator is preferably a photoradical polymerization initiator.
<Thermal Polymerization Step>

The forming die to be used in the production method for a cured product of the invention may be referred to also as a thermoforming die. In general, the thermoforming die is composed of two die parts and is preferably so designed that a content can be heated under pressure in the combination of the two die parts. In the production method for producing a cured product of the invention, preferably, a mold is used as the forming die in the thermal polymerization step to obtain a cured product. The thermoforming die of the type for use herein is described, for example, in JP-A 2009-126011.
(Introduction into Forming Die)

In the production method for a cured product of the invention, first, the semi-cured product produced according to the semi-cured product production method of the invention mentioned above, into a forming die. First described is the step of putting the semi-cured product into the forming die.

The semi-cured product after photoirradiation and/or heating is directly set in a thermoforming die and is photoirradiated and/or heated therein, or is set in a die different from a thermoforming die and is photoirradiated and/or heated therein, as described in the section of the semi-cured product production method of the invention. In the case where the semi-cured product after photoirradiation is directly set in a thermoforming die and is photoirradiated and/or heated therein, the operation of putting the semi-cured product into a thermoforming die is unnecessary, and the semi-cured product is written to be put in a forming die merely for explanation.

On the other hand, in the case where the semi-cured product after photoirradiation and/or heating is set in a die different from a thermoforming die and is photoirradiated and/or heated therein, the operation means the step of transferring the semi-cured product into a thermoforming die. For the method of transferring the semi-cured product after photoirradiation and/or heating into a thermoforming die, for example, usable is a vacuum tweezer system equipped with a syringe, a vacuum pad and a vacuum generator. The semi-cured product of the invention has a complex viscosity falling within a specific range, and therefore can be readily transferred into a thermoforming die by the use of such a vacuum tweezer system.
(Pressure Forming/Heating)

According to the production method for a cured product of the invention, the semi-cured product put in a forming die is formed under pressure and heated for polymerization to give a cured product.

Here, pressure forming and heating may be carried out simultaneously, or heating may be carried out after pressure forming, or pressure forming may be carried out after heating. Above all, preferably, pressure forming and heating are carried out simultaneously. Also preferably, after simultaneous pressure forming and heating, the product may be further heated at a higher temperature after the pressure given thereto has become stable.

The pressure for the pressure forming is preferably from 1 kg/cm² to 100 kg/cm², more preferably from 3 kg/cm² to 50 kg/cm², even more preferably from 3 kg/cm² to 30 kg/cm².

The heating temperature is preferably from 80 to 300° C. when the heating is, carried out simultaneously with pressure forming, and is more preferably from 120 to 300° C., even more preferably from 150 to 280° C.

On the other hand, in the case where the product is further heated at a higher temperature after the pressure given thereto has become stable, the heating temperature is preferably from 80 to 300° C., more preferably from 120 to 300° C., even more preferably from 150 to 280° C.

The time of thermal polymerization is preferably from 30 to 1000 seconds, more preferably from 30 to 500 seconds, even more preferably from 60 to 300 seconds.

The atmosphere in thermal polymerization is preferably in air or after purging with an inert gas; and more preferred is an atmosphere purged with nitrogen to have an oxygen concentration of at most 1%.

[Cured Product]

The cured product of the invention is one produced according to the cured product production method of the invention. Preferred characteristics of the cured product of the invention are described below.

(Refractive Index)

Preferably, the cured product of the invention has a high refractive index from the viewpoint of using it for optical components, especially for lenses. Preferably, the refractive index nD at a wavelength of 589 nm of the cured product of the invention is at least 1.45, more preferably at least 1.61, even more preferably at least 1.62, still more preferably at least 1.63, most preferably at least 1.65.

(Abbe's Number)

Preferably, the cured product of the invention has a low Abbe's number from the viewpoint of reducing the chromatic aberration in using it for optical components, especially for lenses. Preferably, the Abbe's number at a wavelength of 589 nm of the cured product of the invention is at most 25, more preferably at most 24, even more preferably at most 23.5, still more preferably at most 23, furthermore preferably at most 22.5, and most preferably at most 22.

In this description, the Abbe's number vD is computed according to the following equation (A), in which nD, nF and nC each are a refractive index at a wavelength of 589 nm, 486 nm and 656 nm, respectively.

$$vD = \frac{nD - 1}{nF - nC} \qquad \text{Equation (A)}$$

(Size)

Preferably, the maximum thickness of the cured product of the invention is from 0.1 to 10 mm. The maximum thickness is more preferably from 0.1 to 5 mm, even more preferably from 0.15 to 3 mm. Also preferably, the maximum diameter of the cured product of the invention is from 1 to 1000 mm. The maximum diameter is more preferably from 2 to 50 mm, even more preferably from 2.5 to 10 mm. The cured product having the size as above is especially useful for optical components having a high refractive index. In general, it is not easy to produce such a thick molded article according to a solution casting method since the solvent is difficult to remove, or that is, forming the article is not easy. However, according to the semi-cured product production method and the cured product production method of the invention, it is easy to form such a thick molded article while preventing the generation of burrs, and therefore the good rate of the products is high. The invention therefore realizes cured products having complicated shapes such as non-spherical shapes, etc. To that effect, according to the invention, it is easy to produce cured products having high heat resistance.

[Optical Components]

Preferably, the cured product of the invention is a molded article having a high refractive index and a high light transmittance and lightweight and excellent in optical characteristics, and the optical component of the invention uses the cured product of the invention. The type of the optical component is not specifically defined. In particular, the cured product of the invention is favorably used for optical components that utilize the excellent optical characteristics of curable resin compositions, especially for light-transmissive optical components (so-called passive optical components). Optically-functional devices equipped with such optical components include, for example, various types of display devices (liquid-crystal displays, plasma displays, etc.), various types of projector devices (OHP, liquid-crystal projectors, etc.), optical fiber communication systems (light waveguides, light amplifiers, etc.), image-taking devices such as cameras, videos, etc.

The passive optical components for use in optically-functional devices include, for example, lenses, prisms, prism sheets, panels (tabular molded articles), films, optical waveguides (filmy, fiber-like, etc.), optical discs, LED sealants, etc. If desired, the passive optical components may have a multilayer structure, for example, by providing thereon a coating layer, such as a protective layer for preventing mechanical damage of the coating surface by friction or abrasion, a light-absorbing layer for absorbing the light having an undesirable wavelength to cause degradation of inorganic particles, substrates and others, a blocking layer for retarding or preventing permeation of reactive small molecules such as moisture, oxygen gas, etc., an antiglare layer, an antireflection layer, a low-refractivity layer, etc., as well as any other additional functional layer added thereto. Specific examples of the optional coating layers include a transparent conductive film and a gas-barrier layer formed of an inorganic oxide coating layer, a gas-barrier layer and a hard coat layer formed of an organic coating layer, etc. The coating method for these layers may be any known coating method such as a vacuum evaporation method, a CVD method, a sputtering method, a dip coating method, a spin coating method, etc.

APPLICATION EXAMPLES

The optical component using the cured product of the invention is especially favorable for lens substrates. The lens substrate produced using the curable resin composition of the present invention has a low Abbe's number and favorably additionally has the advantages of high refractivity light transmittance and lightweightness and is excellent in optical characteristics. By suitably selecting the type of the monomer to constitute the curable resin composition, it is possible to control in any desired manner the refractive index of the lens substrate.

In this description, "lens substrate" means a single component capable of exhibiting a lens function. On and around the surface of the lens substrate, any film and component may be provided in accordance with the service environment and the use of lenses. For example, on the surface of the lens substrate, there may be formed a protective film, an antireflection film, a hard coat film, etc. It is also possible to make the lens substrate intruded and fixed in a substrate holding frame.

However, those films and frame are additional components to the lens substrate and therefore differ from the lens substrate itself referred to in the invention.

In using the lens substrate for lenses, the lens substrate itself may be used as a lens by itself, or additional films or frame may be added thereto for use as a lens, as mentioned above. The type and the shape of the lens using the lens substrate are not specifically defined.

The lens substrate has a low Abbe's number and is favorably used as an achromatic lens, and the achromatic lens is used, for example, for lenses for image-taking devices such as portable or digital cameras, etc.; lenses for movie devices such as TV or video cameras, etc.; and also lenses for in-vehicle devices, endoscope lenses, etc.

EXAMPLES

The characteristics of the invention are described more concretely with reference to the following Examples.

In the following Examples, the material used, its amount and ratio, the details of the treatment and the treatment process may be suitably modified or changed not overstepping the spirit and the scope of the invention. Accordingly, the invention should not be limitatively interpreted by the Examples mentioned below.

Example 1

Synthesis of Condensed Ring-Containing Compound

Synthesis of Condensed Ring-Containing Compound Xa-4

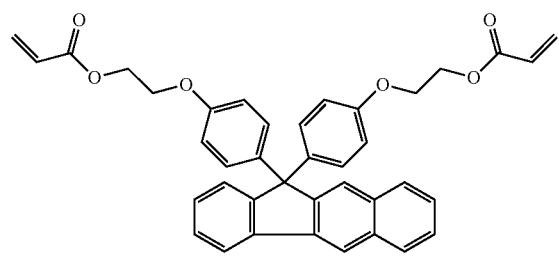

Xa-4

The above Xa-4 was synthesized according to the following method.

The following reaction was performed in a nitrogen stream atmosphere. 20.2 g of 1-indanone and 19.4 g of o-phthalaldehyde were dissolved in 80.0 g of methanol. The reaction solution was heated and, while kept at 60° C., 25.8 g of potassium hydroxide dissolved in 96.0 g of methanol was dropwise added thereto. After stirred for 3 hours, the reaction solution was restored to room temperature, and the precipitated crystal was collected through filtration to give 20.3 g of 2,3-benzofluorenone.

9.0 g of 2,3-benzofluorenone and 8.6 g of phenoxyethanol were suspended in 2.0 g of toluene, and 0.07 g of 3-mercaptopropionic acid was added thereto. 3.6 g of sulfuric acid was dropwise added to this, then stirred at 65° C. for 16 hours, and 0.64 g of methanol was added thereto. After stirred for 1 hour, 12.0 g of water was added thereto, restored to room temperature, then the supernatant was removed, and the residue was purified through column chromatography to give 5.0 g of 9,9-bis[4-(2-hydroxyethoxyl)phenyl]-2,3-benzofluorene.

9.0 g of 9,9-bis[4-(2-hydroxyethoxyl)phenyl]-2,3-benzofluorene and 8.5 g of diisopropylamine were dissolved in 16.0 g of tetrahydrofuran. The reaction solution was cooled with ice, and while kept at 10° C. or lower, 6.0 g of acrylic acid chloride was dropwise added thereto. After restored to room temperature, this was stirred for 1 hour. An aqueous sodium hydrogencarbonate solution was added to the reaction solution, and then extracted with ethyl acetate. The organic layer was collected, Na$_2$SO$_4$ was added thereto, filtered, concentrated, and the concentrated matter was purified through column chromatography to give 7.7 g of Xa-4.

$^1$H-NMR data of the compound are shown in FIG. 1.

Example 2

Synthesis of Condensed Ring-Containing Compound Xa-5

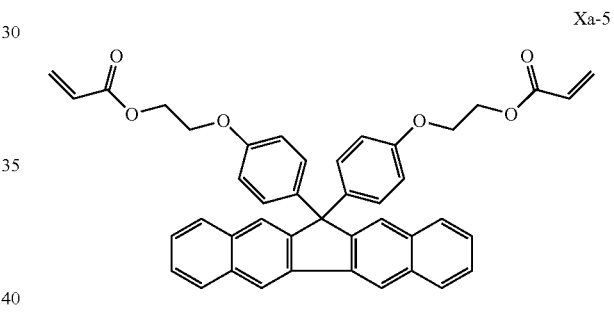

Xa-5

The above Xa-5 was synthesized according to the following method.

The following reaction was performed in a nitrogen stream atmosphere. 10.0 g of dibenzo[β,η]fluoren-12-one and 19.7 g of phenoxyethanol were suspended in 60 g of toluene, and 0.23 g of 3-mercaptopropionic acid was added thereto. 7.7 g of sulfuric acid was dropwise added thereto, stirred at 120° C. for 27 hours, then 20 g of methanol was added, stirred for 1 hours, 30 g of water was added and restored to room temperature, the supernatant was removed, and the residue was purified through column chromatography to give 2.6 g of 9,9-bis [4-(2-hydroxyethoxyl)phenyl]-dibenzo[β,η]fluorene. 2.6 g of 9,9-bis[4-(2-hydroxyethoxyl)phenyl]-dibenzo[β,η]fluorene and 3.3 g of diisopropylamine were dissolved in 10 g of dichloromethane. The reaction solution was cooled with ice, and while kept at 10° C. or lower, 2.6 g of acrylic acid chloride was dropwise added thereto. After restored to room temperature, this was stirred for 1 hour. An aqueous sodium hydrogencarbonate solution was added to the reaction solution, and then extracted with ethyl acetate. The organic layer was collected, Na$_2$SO$_4$ was added thereto, filtered, concentrated, and the concentrated matter was purified through column chromatography to give 0.7 g of Xa-5.

Figure 2:
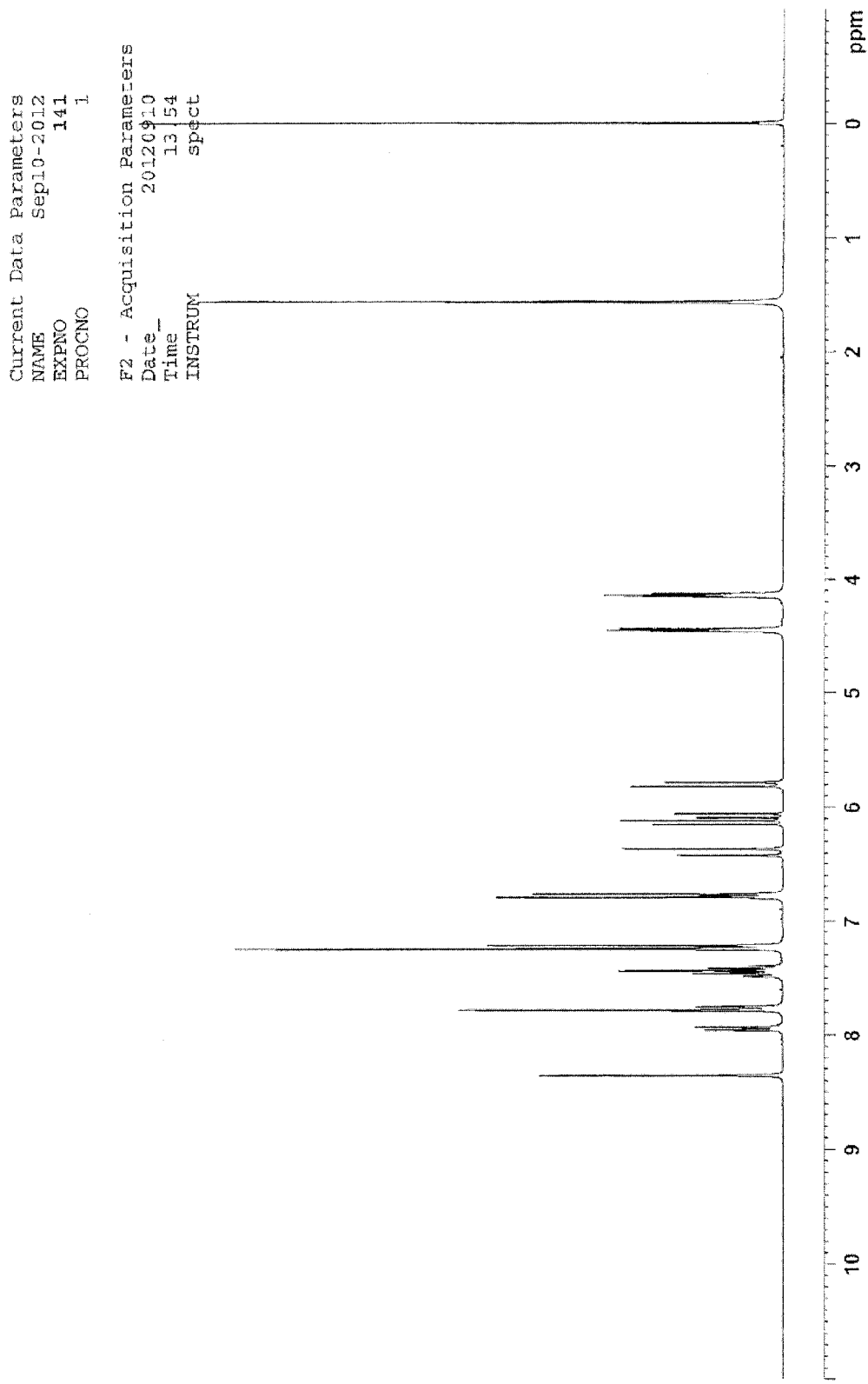
FIG. 2 is a $^1$H-NMR chart of the condensed ring-containing compound Xa-5.

$^1$H-NMR data of the compound are shown in FIG. 2.

Example 3
Synthesis of Condensed Ring-Containing Compounds Xa-6 to 15
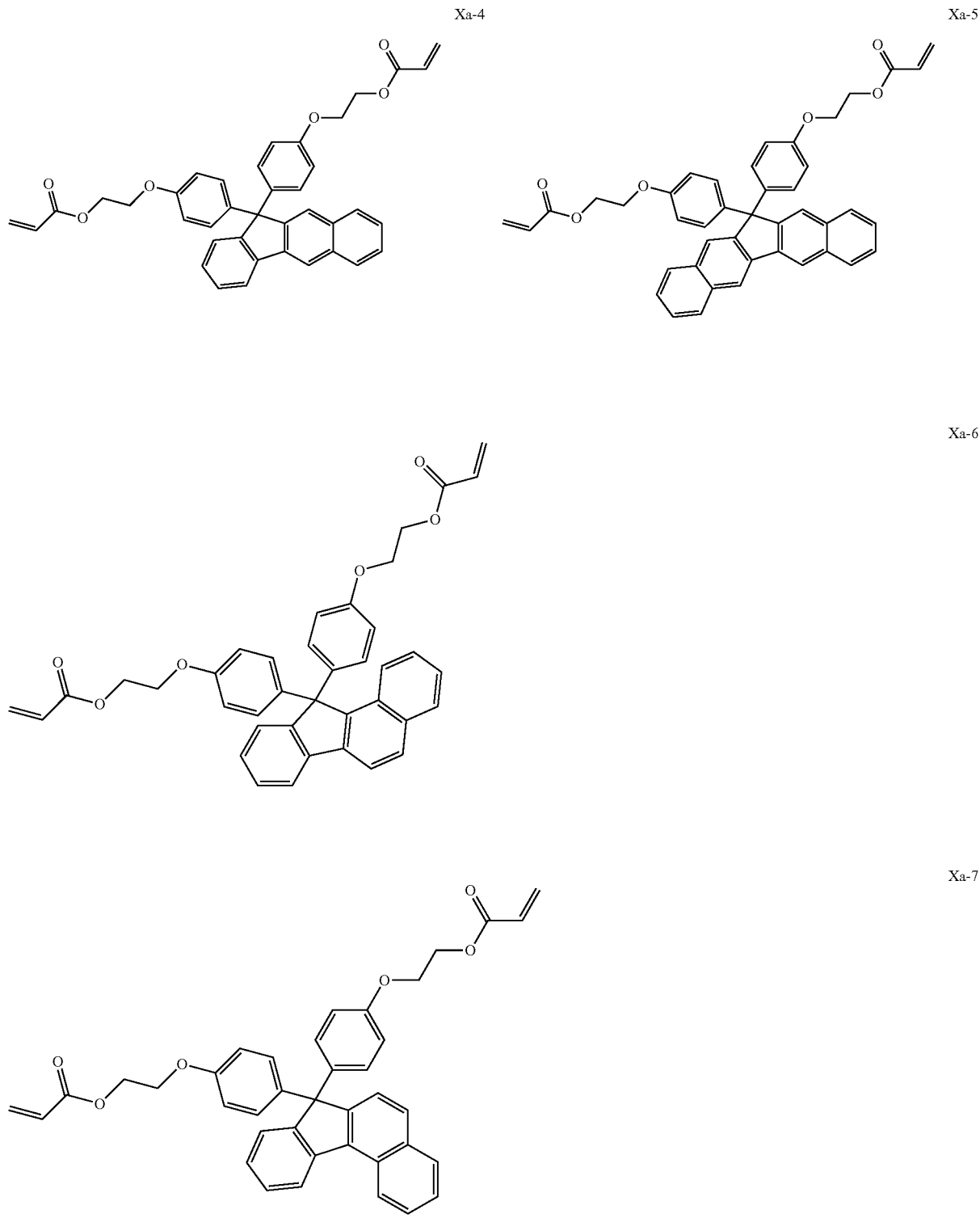

-continued
Xa-8
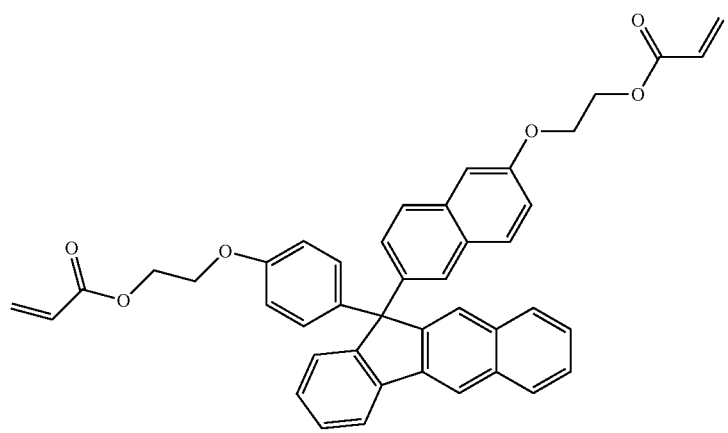
Xa-9
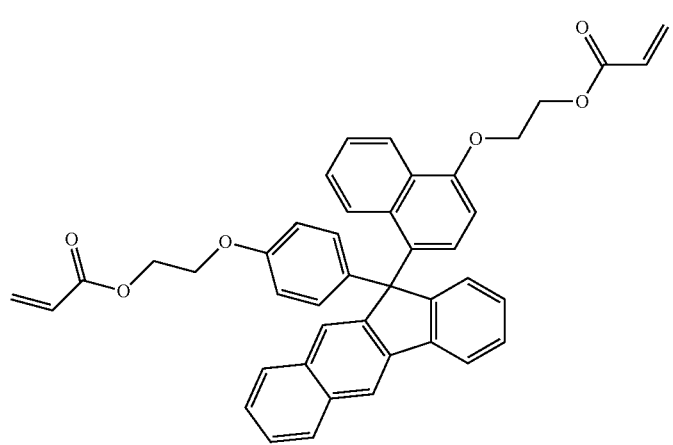
Xa-10 Xa-11
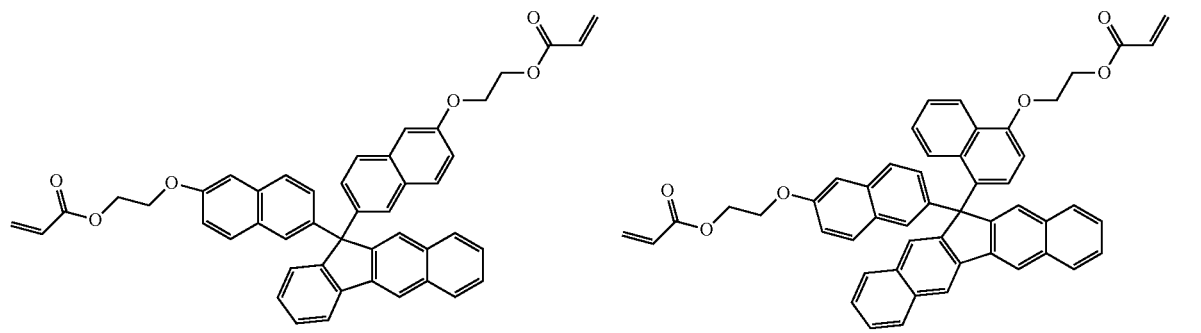
Xa-12
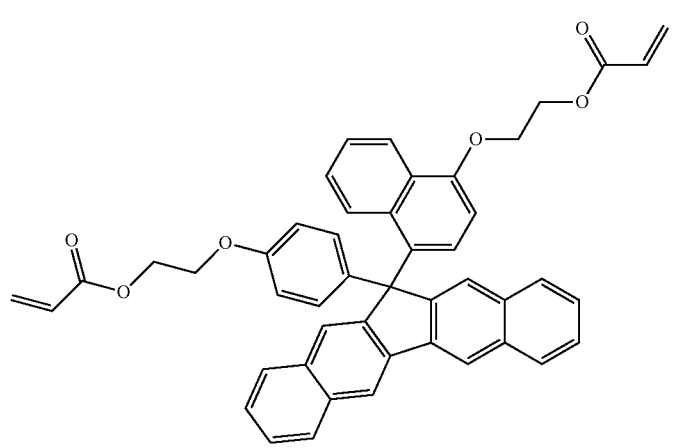

Xa-13
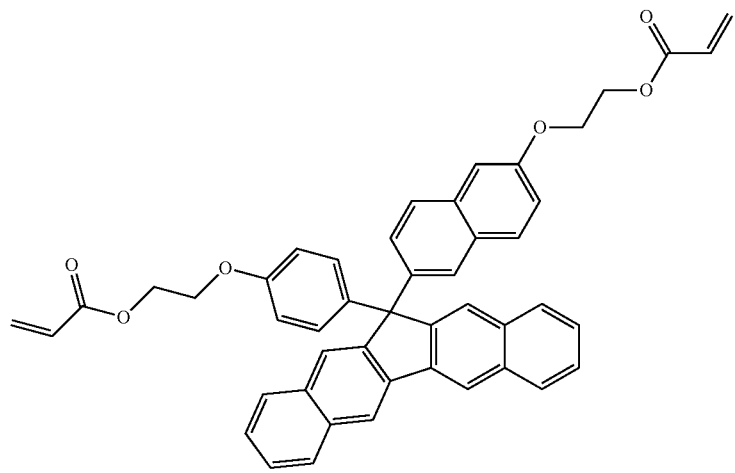
Xa-14
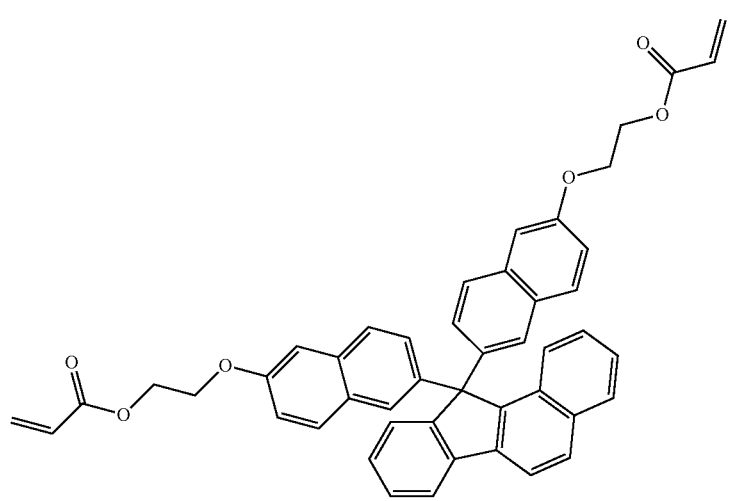
Xa-15
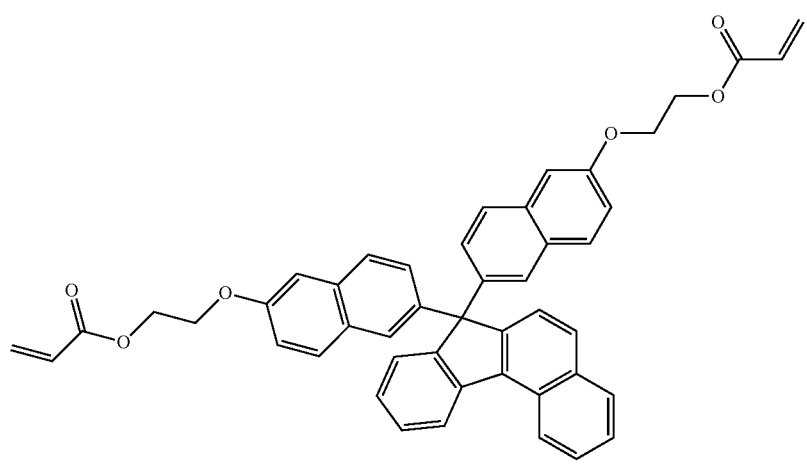

The above Xa-6 to 15 were synthesized in the same manner as that for the above Xa-4.

Figure 3:
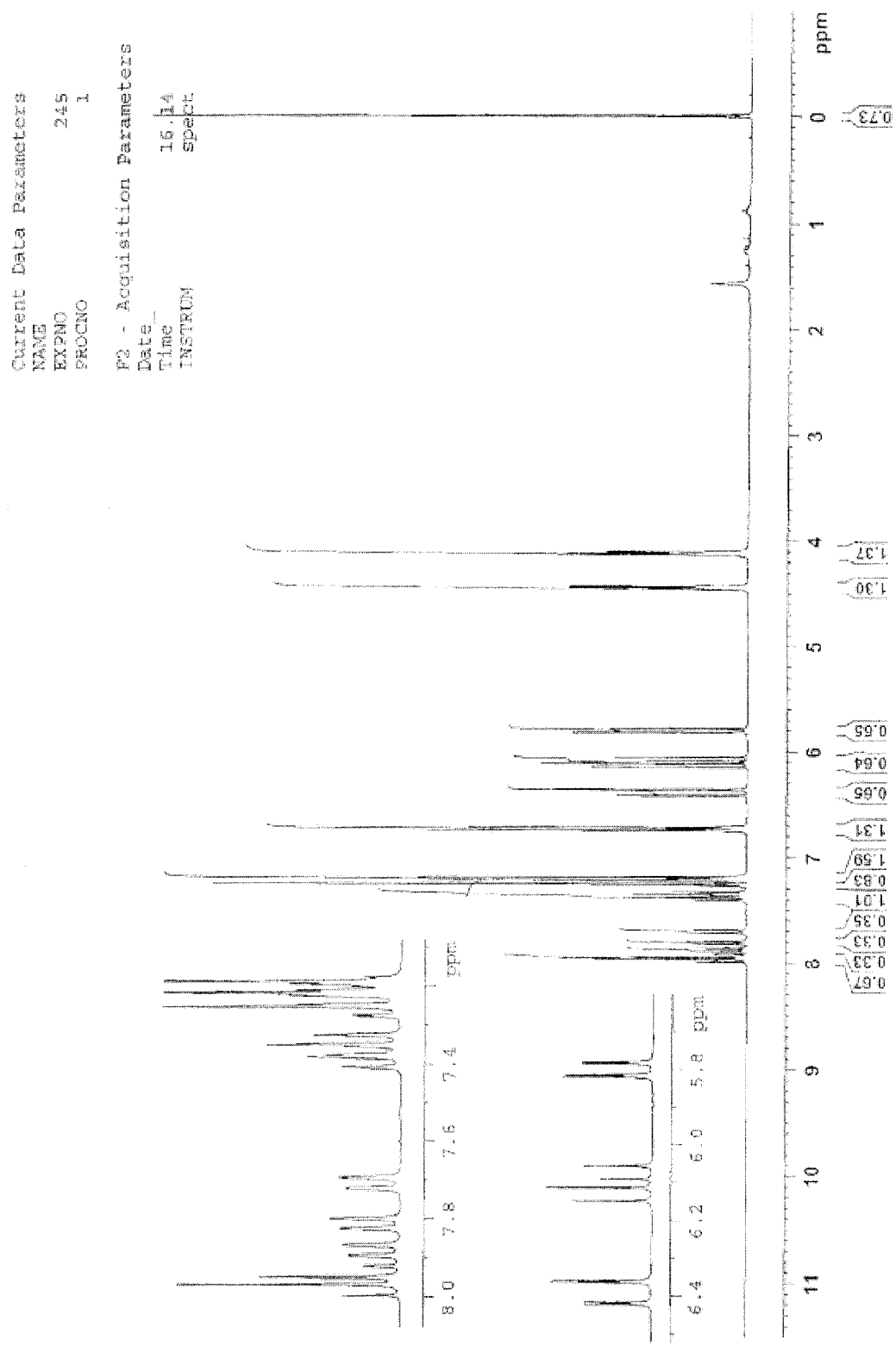
FIG. 3 is a $^1$H-NMR chart of the condensed ring-containing compound Xa-6.
Figure 4:
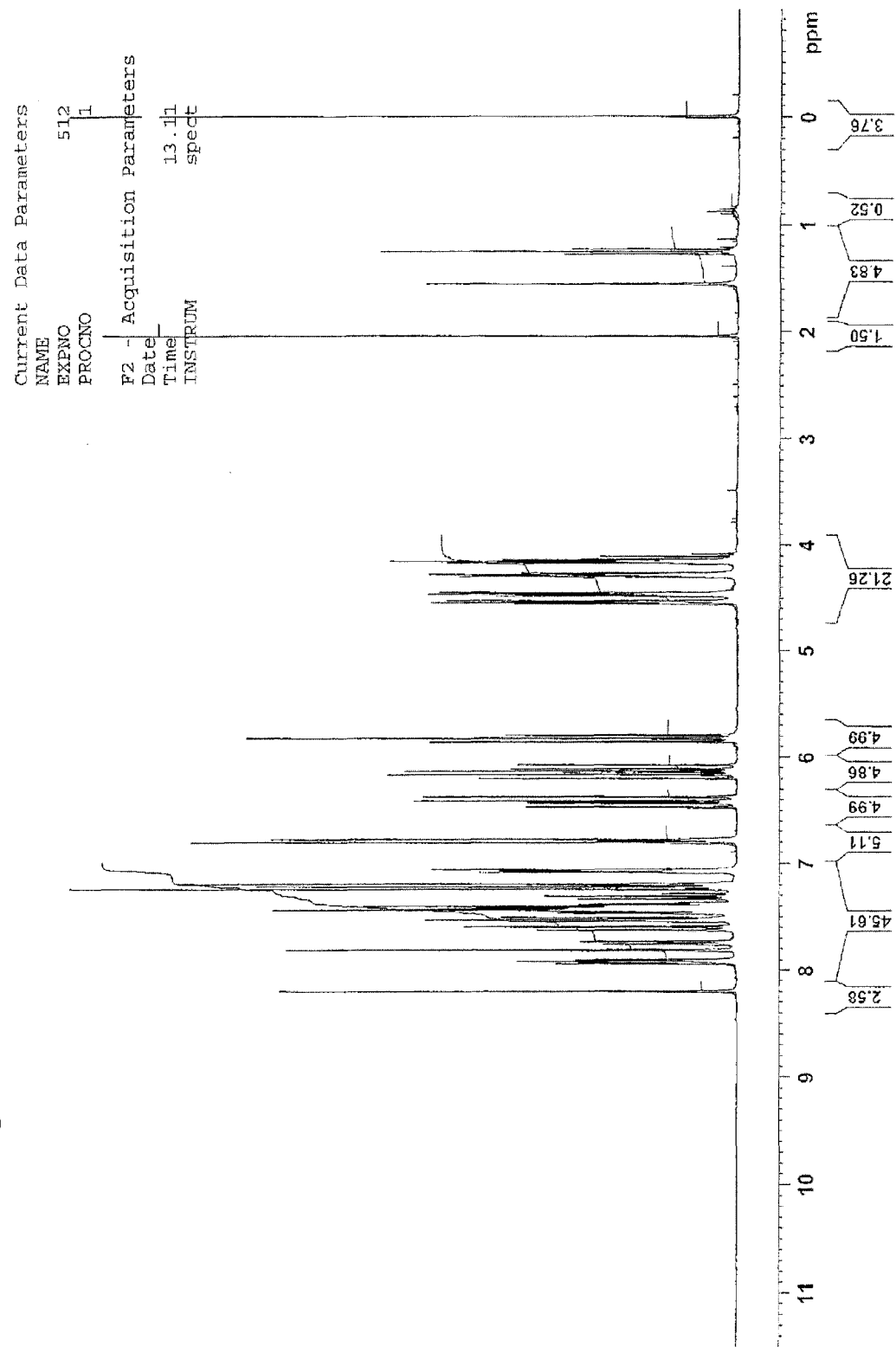
FIG. 4 is a $^1$H-NMR chart of the condensed ring-containing compound Xa-8.
Figure 5:
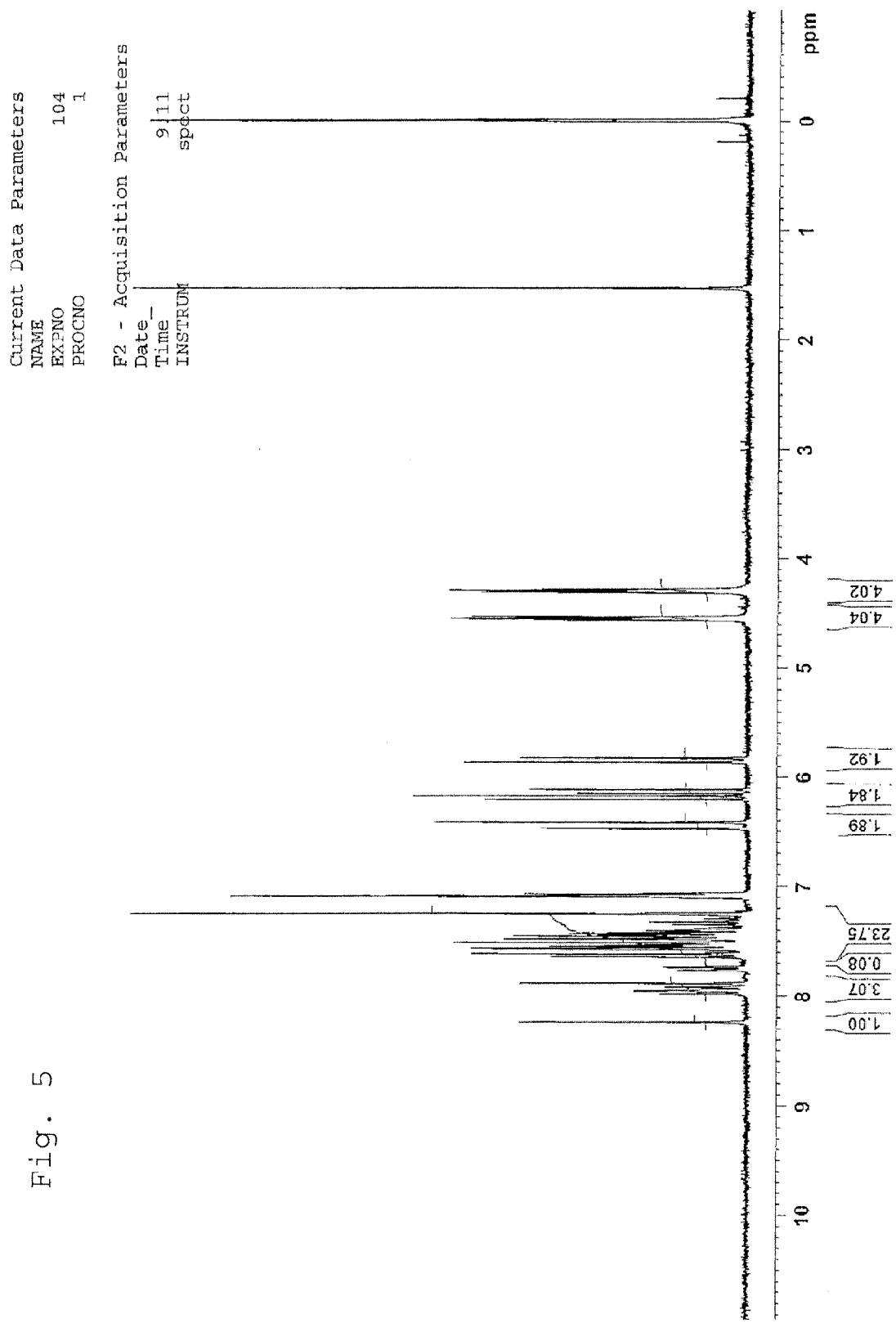
FIG. 5 is a $^1$H-NMR chart of the condensed ring-containing compound Xa-10.

¹H-NMR data of Xa-6, Xa-8 and Xa-10 are shown in FIG. 3 to FIG. 5, respectively.

Examples 8 to 10

Synthesis of Condensed Ring-Containing Compounds A to C>

Condensed-Ring Containing Compound A:

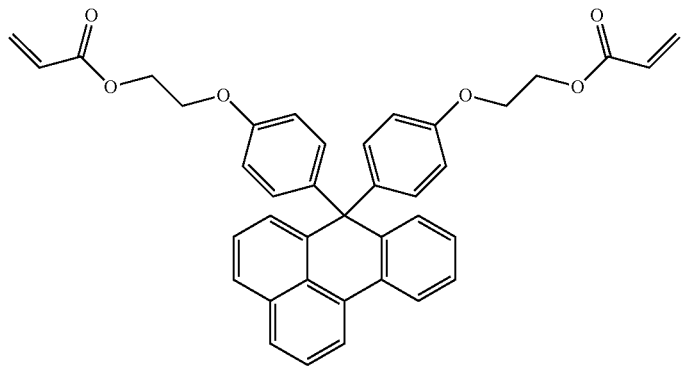

Condensed-Ring Containing Compound B:

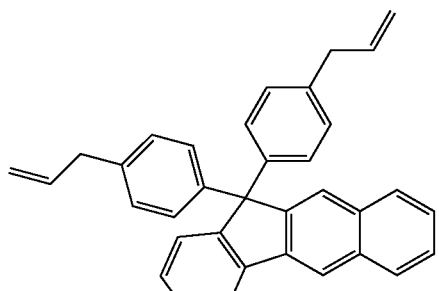

Condensed-Ring Containing Compound C:

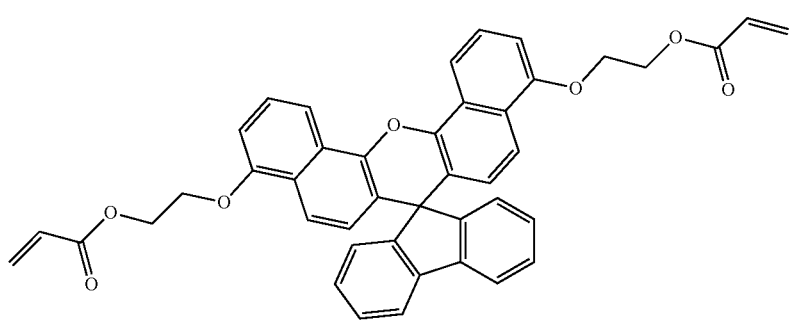

The above condensed ring-containing compounds A to C were synthesized in the same manner as that for the above Xa-4.

Examples 11 to 37, Comparative Examples 1 to 3

(1) Materials for Use in Curable Resin Composition

<Condensed Ring-Containing Compound>

The condensed ring-containing compounds A to C, and Xa-4 to Xa-15 synthesized in the above Examples 1 to 3 were used.

In addition, the following compounds 1 to 3 were prepared according to the method described in the following publications, respectively.

Compound 1: The following compound described in Example 28 in JP-A 2011-068624

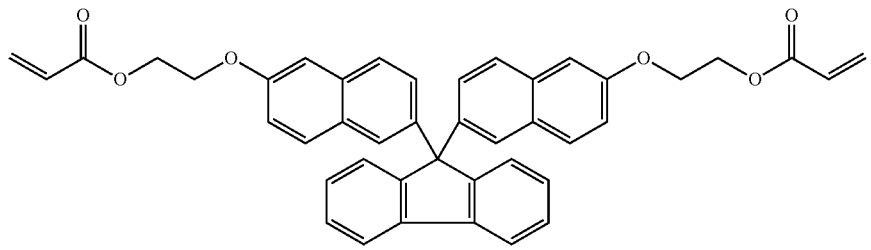

Compound 2: Aa-1 (the following compound) described in Example 1 in JP-A 2012-107191

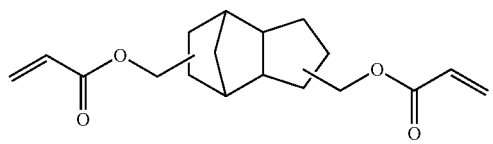

Compound 3: (19) (the following compound) in Example 1 in JP-A 2012-082386

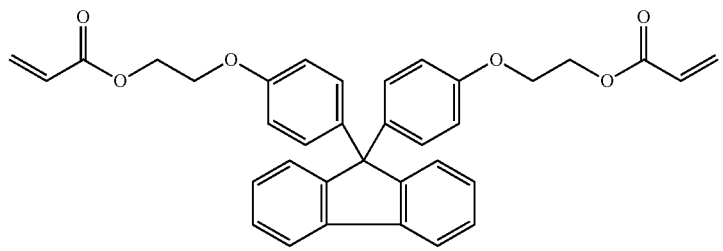

<Monofunctional (Meth)Acryl Monomer>
The following PhOEA: Tokyo Chemical Industry's trade name, 2-phenoxyethyl acrylate
The following BnA: Aldrich's trade name, benzyl acrylate

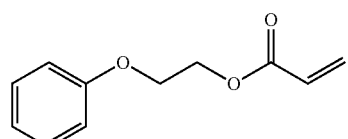

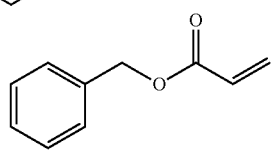

<Non-Conjugated Vinylidene Group-Containing Compound>

Non-conjugated vinylidene group-containing compounds usable in Examples are shown below. Optical isomers can be used with no specific limitation.
The following B-2: Aldrich's trade name, (+)-Aromadendrene
The following B-3: Aldrich's trade name, (+)-Longifolene
The following B-5: Tokyo Chemical Industry's trade name, β-Caryophyllene

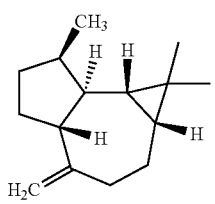
(B-2)

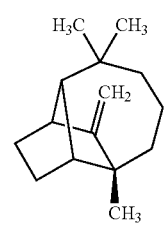
(B-3)

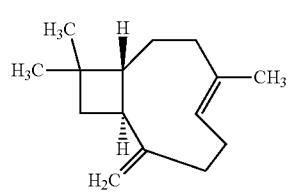
(B-5)

<Photoradical Initiator>
The following F-1: BASF's trade name, Irgacure 184

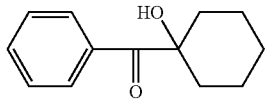
(F-1)

<Thermal Radical Polymerization Initiator>
The following F-2: NOF's trade name, Perbutyl O
The following F-3: NOF's trade name, Percumyl H

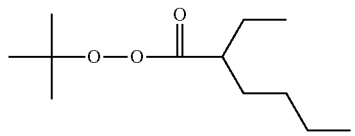
(F-2)

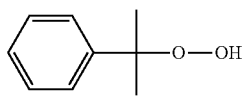
(F-3)

(2) Preparation of Curable Resin Composition

The above components were mixed in the compositional ratio shown in Table 1 below, stirred and homogenized to prepare a curable resin composition.

(3) Evaluation

Evaluation of Mold Clearance Leakage of Resin 10 mg of the curable resin composition cast into a columnar transparent preform die having a diameter of 4 mm and a height of 1.5 mm was irradiated with UV rays at 15 mW/cm$^2$ for the period of time shown in the following Table, using Execure 3000 (by HOYA), thereby forming a semi-cured product. From a thermoforming mold for 4.0-mm lenses, containing an upper die part (top die part), a body die part and a lower die part (bottom die part), the top die part was removed, and the semi-cured product having the shape of the preform was transferred from the preforming mold to the thermoforming mold, using a vacuum tweezer system. After heated at 80° C., this was further heated up to 200° C. while a pressure of 30 kgf/cm$^2$ was kept given to the semi-cured product, and then cooled to room temperature.

In the process from transferring the semi-cured product to the thermoforming mold to cooling it to room temperature, the length of the burrs formed by leakage of the resin through the thermoforming mold clearance was measured, and based on the thus-measured length, the resin composition was evaluated according to the following criteria.
A: The resin leakage was less than 0.2 mg.
B: The resin leakage was from 0.2 mg to less than 0.3 mg.
C: The resin leakage was 0.3 mg or more, and the level is problematic in practical use.

The obtained results are shown in the following Table 1. The evaluation of mold clearance leakage of resin employed here includes the additional step of transferring the semi-cured product from the preforming mold to the thermoforming mold, and is, different from conventional evaluation for resin leakage, under severer conditions than in ordinary leakage evaluation.
(Evaluation of Lens Moldability)

The same process as that for the evaluation of mold clearance leakage of resin was repeated 10 times, and the appearance of each lens thus produced was checked with Keyence's Digital Microscope (trade name: VHX-1000).

Those with fine wrinkles on the surface of the flange part each lens, and those' with cracks were considered as not good; and those with neither wrinkles not cracks were considered as good. Ten lenses were evaluated, and of those, the rate of good ones was referred to as a good rate. The resin composition was evaluated according to the following criteria.
A: The good rate was 85% or more.
B: The good rate was 70% or more.
C: The good rate was 30% or more.
D: The good rate was less than 30%.

The obtained results are shown in the following Table 1.
(Refractive Index, Abbe's Number)

The curable resin composition was cast into a transparent glass die having a diameter of 10 mm and a thickness of 1 mm, and irradiated with UV rays at 15 mW/cm$^2$ for the period of time shown in the following Table, using Execure 3000 (by HOYA), thereby giving a semi-cured product.

Next, the resulting semi-cured product was heated at 200° C. for 5 minutes, using a hot plate, thereby giving a thermally-cured product. The refractive index at 589 nm and the Abbe's number of the thus-obtained thermally-cured product were measured, using Abbe Meter (by Atago).

The obtained results are shown in the following Table 1.
<Mold Releasability>

The curable resin composition having a diameter of 10 mm and a thickness of 1 mm, as sandwiched between transparent glass and a metal plate plated in the same manner as that for a mold, was irradiated with UV rays at 15 mW/cm$^2$ for the period of time shown in the following Table, using Execure 3000 (by HOYA), thereby giving a semi-cured product.

Next, the semi-cured product was heated at 200° C. for 5 minutes, using a hot plate, thereby giving a thermally-cured product. The resultant thermally-cured product was heated in an oven at 150° C. for 2 hours, and the proportion of the cured product having remained on the glass when the glass and the metal plate were separated was determined. The composition was evaluated according to the following criteria.
A: The proportion of the cured product having remained on the glass was 10% or less.
B: The proportion of the cured product having remained on the glass was 20% or less.

C: The proportion of the cured product having remained on the glass was 30% or less.
D: The proportion of the cured product having remained on the glass was 50% or more.

The obtained results are shown in the following Table 1.

On the other hand, the cured product produced using the curable resin composition of Comparative Example 1, which does not contain a non-conjugated vinylidene group-containing compound represented by the general formula (2), generates burrs during molding.

TABLE 1-1

| | | | Example 11 | Example 12 | Example 13 | Example 14 | Example 15 | Example 16 | Example. 17 | Example 18 | Example 19 | Example 20 |
|---|---|---|---|---|---|---|---|---|---|---|---|---|
| Compound | Condensed Ring-Containing Compound | compound added amount | A 70.9 | B 70.9 | C 70.9 | Xa-4 70.9 | Xa-5 68.7 | Xa-6 70.9 | Xa-7 70.9 | Xa-8 70.9 | Xa-9 70.9 | Xa-10 70.9 |
| | Other Polyfunctional (Meth)acrylic Monomer | compound added amount | none | none | none | none | none | none | none | none | none | none |
| | Non-conjugated Vinylidene Group-Containing Compound | compound added amount | B-5 4.5 | B-5 4.5 | B-5 4.5 | B-5 4.5 | B-5 4.5 | B-5 4.5 | B-5 4.5 | B-5 4.5 | B-5 4.5 | B-5 4.5 |
| | Monofunctional (Meth)acrylic Monomer | compound added | BnA 22.8 | BnA 22.8 | PhOEA 22.8 | PhOEA 22.8 | PhOEA 25 | PhOEA 22.8 | PhOEA 22.8 | PhOEA 22.8 | PhOEA 22.8 | PhOEA 22.8 |
| | Photoradical Polymerization Initiator (F-1) | added amount | 0.1 | 0.1 | 0.1 | 0.1 | 0.1 | 0.1 | 0.1 | 0.1 | 0.1 | 0.1 |
| | Thermal Radical Polymerization Initiator (F-2, F-3) | added amount | 1.7 | 1.7 | 1.7 | 1.7 | 1.7 | 1.7 | 1.7 | 1.7 | 1.7 | 1.7 |
| Evaluation | Evaluation of Mold Clearance Leakage of Resin | | A | A | A | A | A | A | A | A | A | A |
| | Evaluation of Lens Moldability | | B | B | B | A | A | A | A | A | A | A |
| | Evaluation of Mold Releasability | | A | A | A | A | A | A | A | A | A | A |
| | Refractive Index | | 1.62 | 1.61 | 1.62 | 1.63 | 1.65 | 1.64 | 1.64 | 1.66 | 1.66 | 1.67 |
| | Abbe's Number | | 25.0 | 24.0 | 23.4 | 22.9 | 22.3 | 22.7 | 22.8 | 21.8 | 21.6 | 21.3 |

| | | | Example 21 | Example 22 | Example 23 | Example 24 | Example 25 | Example 26 | Example 27 | Example 28 | Example 29 |
|---|---|---|---|---|---|---|---|---|---|---|---|
| Compound | Condensed Ring-Containing Compound | compound added amount | Xa-11 70.9 | Xa-12 70.9 | Xa-13 70.9 | Xa-14 70.9 | Xa-15 70.9 | Compound 1 58.7 | Xa-4 70.9 | Xa-4 70.9 | Xa-4 43.7 |
| | Other Polyfunctional (Meth)acrylic Monomer | compound added amount | none | none | none | none | none | none | none | none | none |
| | Non-conjugated Vinylidene Group-Containing Compound | compound added amount | B-5 4.5 | B-5 4.5 | B-2 4.5 | B-3 4.5 | B-5 4.5 | B-5 4.5 | B-2 4.5 | B-3 4.5 | B-5 40 |
| | Monofunctional (Meth)acrylic Monomer | compound added | PhOEA 22.8 | PhOEA 22.8 | PhOEA 22.8 | PhOEA 22.8 | PhOEA 22.8 | PhOEA 35 | PhOEA 22.8 | PhOEA 22.8 | BnA 14.5 |
| | Photoradical Polymerization Initiator (F-1) | added amount | 0.1 | 0.1 | 0.1 | 0.1 | 0.1 | 0.1 | 0.1 | 0.1 | 0.1 |
| | Thermal Radical Polymerization Initiator (F-2, F-3) | added amount | 1.7 | 1.7 | 1.7 | 1.7 | 1.7 | 1.7 | 1.7 | 1.7 | 1.7 |
| Evaluation | Evaluation of Mold Clearance Leakage of Resin | | A | A | A | A | A | A | A | A | B |
| | Evaluation of Lens Moldability | | A | A | A | A | A | B | B | B | B |
| | Evaluation of Mold Releasability | | A | A | A | A | A | A | A | A | B |
| | Refractive Index | | 1.67 | 1.68 | 1.68 | 1.67 | 1.67 | 1.61 | 1.63 | 1.63 | 1.60 |
| | Abbe's Number | | 21.4 | 20.8 | 20.9 | 21.0 | 21.2 | 24.2 | 23.2 | 23.3 | 27.9 |

From the above Table 1, it is known that the cured product produced using the curable resin composition of the present invention is prevented from generating burrs during molding thereof and has a low Abbe's number.

The cured product produced using the curable resin composition of Comparative Example 2, which uses a condensed ring-containing compound falling outside the scope of the general formula (1) in the present invention, has a high Abbe's number.

Similarly, the cured product produced using the curable resin composition of Comparative Example 3, which uses a condensed ring-containing compound falling outside the scope of the general formula (1) in the present invention, has a high Abbe's number.

The semi-cured products produced during the course of evaluation of the curable resin composition of the present invention all had a complex viscosity falling within a range of from $10^5$ to $10^8$ mPa·s at 25° C. and at a frequency of 10 Hz.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/075283, filed on Sep. 19, 2013; Japanese Patent Application No. 2012-211856 filed on Sep. 26, 2012; and Japanese Patent Application No. 2013-138415 filed on Jul. 1, 2013, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. A curable resin composition containing a condensed ring-containing compound represented by the following general formula (5), a non-conjugated vinylidene group-containing compound represented by the following general formula (2), and at least one of a thermal- or photo-radical polymerization initiator:

General Formula (5)

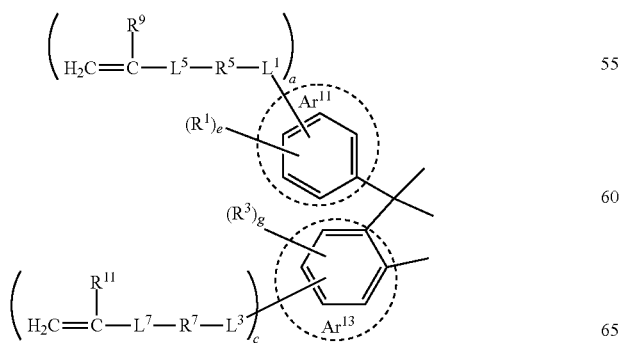
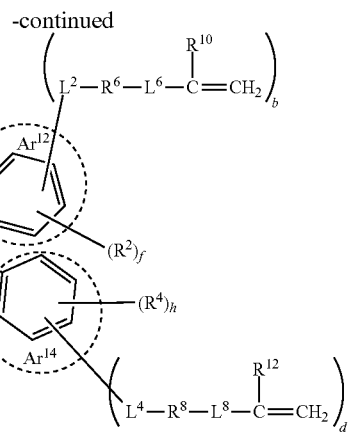

wherein in the general formula (5), $Ar^{11}$ and $Ar^{12}$ each independently represent an aryl or heteroaryl group containing the benzene ring surrounded by the broken line, $Ar^{13}$ and $Ar^{14}$ each independently represent an aryl or heteroaryl group containing the benzene ring surrounded by the broken line, and at least one of $Ar^{13}$ and $Ar^{14}$ is an aromatic condensed ring group containing the benzene ring surrounded by the broken line as one condensed ring therein, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, e, f, g and h each independently indicate an integer of 0 or more, the upper limit of e and f each is 5-a and 5-b, respectively, the upper limit of g and h each is a value calculated by subtracting c or d from the possible maximum number of the substituents that $Ar^{13}$ and $Ar^{14}$ each may have, provided that in a case where $Ar^{13}$ and $Ar^{14}$ each are an aromatic condensed ring group containing the benzene ring surrounded by the broken line as one condensed ring therein, the structures surrounded by c's or d's parentheses as well as $R^3$ and $R^4$ each may independently substitute on the benzene ring surrounded by the broken line or on any other ring than the benzene ring surrounded by the broken line;

General Formula (2)

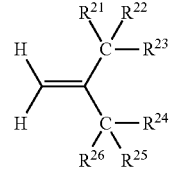

wherein $R^{21}$ to $R^{26}$ each independently represent a substituent, at least one of $R^{21}$ to $R^{26}$ forms a ring, or at least two bond to each other to form a ring.

2. The curable resin composition according to claim 1, wherein the condensed ring-containing compound represented by the general formula (5) is represented by any of the following general formulae (6) to (9):

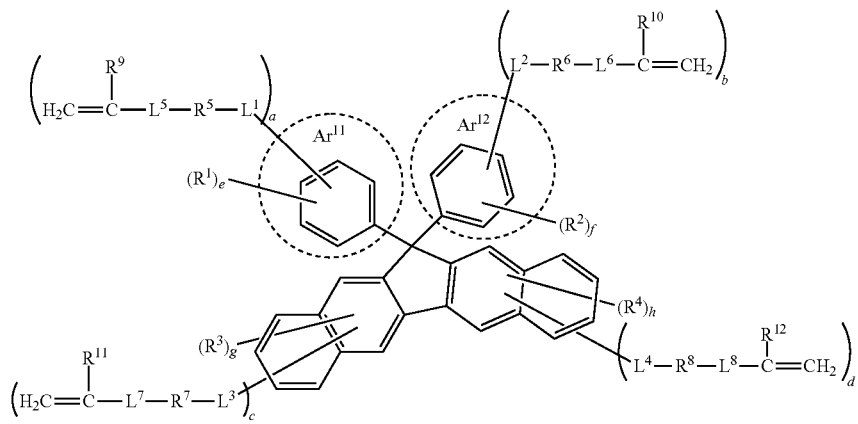

General Formula (6)

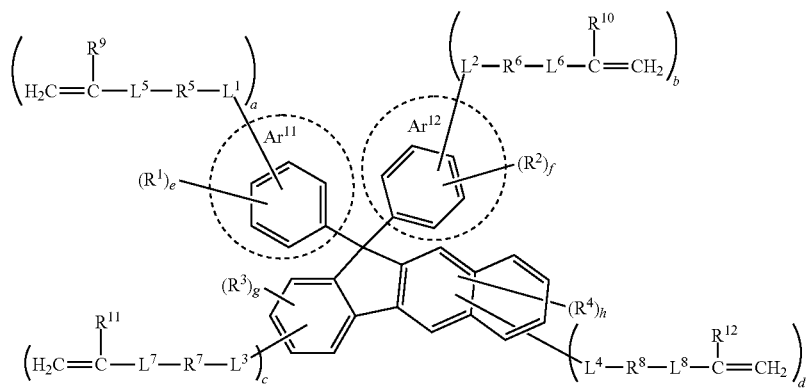

General formula (7)

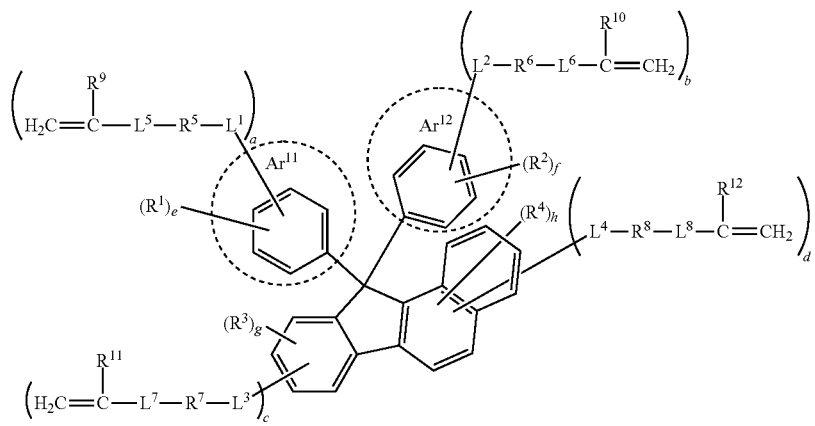

General formula (8)

General Formula (9)

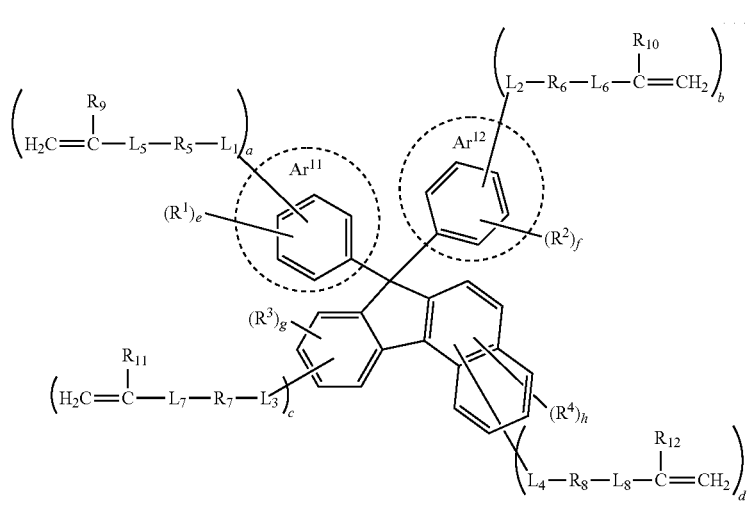

wherein in the general formulae (6) to (9), $Ar^{11}$ and $Ar^{12}$ each independently represent an aryl or heteroaryl group containing the benzene ring surrounded by the broken line, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, e, f, g and h each independently indicate an integer of 0 or more, provided that in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

3. The curable resin composition according to claim 2, wherein the condensed ring-containing compound represented by the general formulae (6) to (9) is represented by any of the following formulae (6A), (7A), (8A), (9A), (6B), (7B), (8B) and (9B):

General Formula (6A)

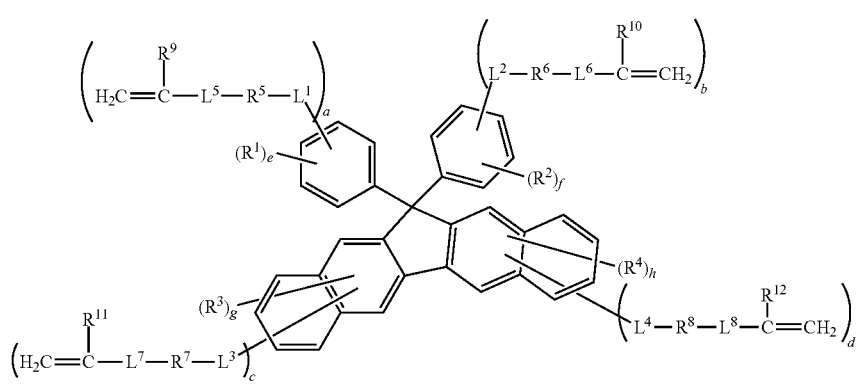

General Formula (7A)

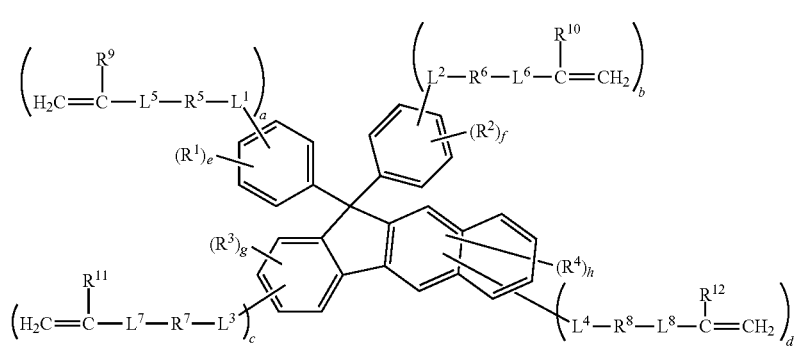

General Formula (8A)

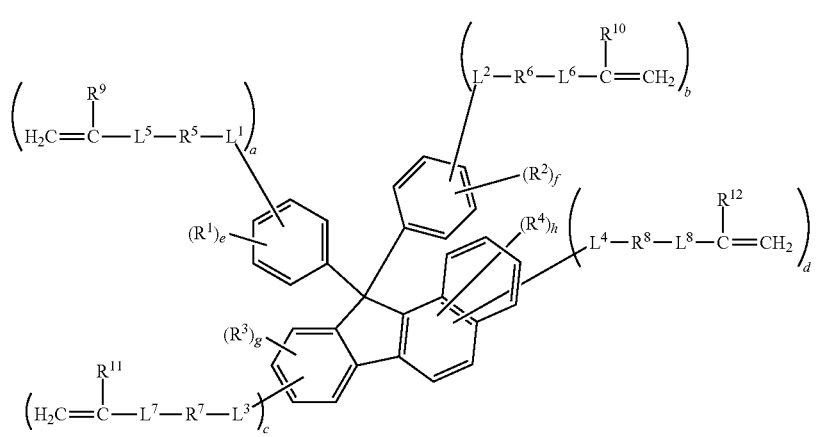

General Formula (9A)

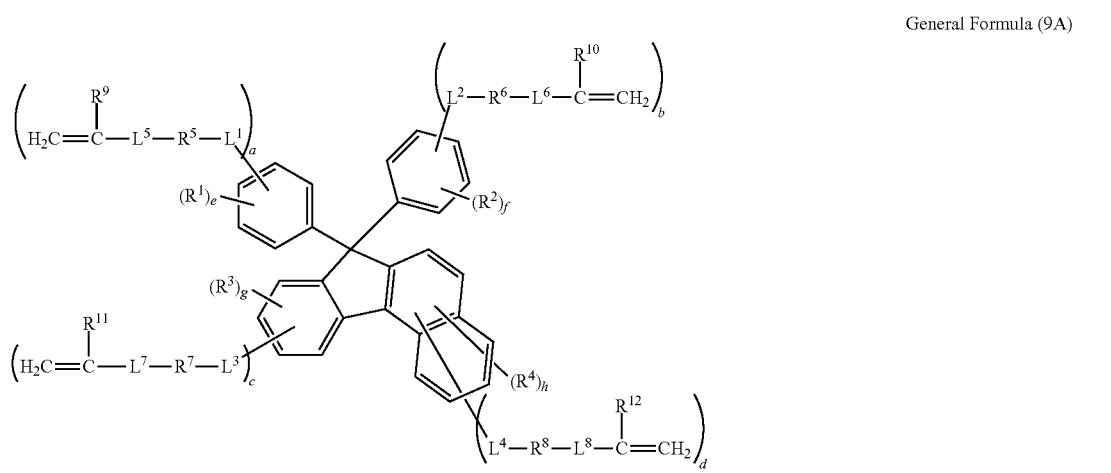

wherein in the general formulae (6A), (7A), (8A) and (9A), $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, and e, f, g and h each independently indicate an integer of 0 or more;

General Formula (6B)

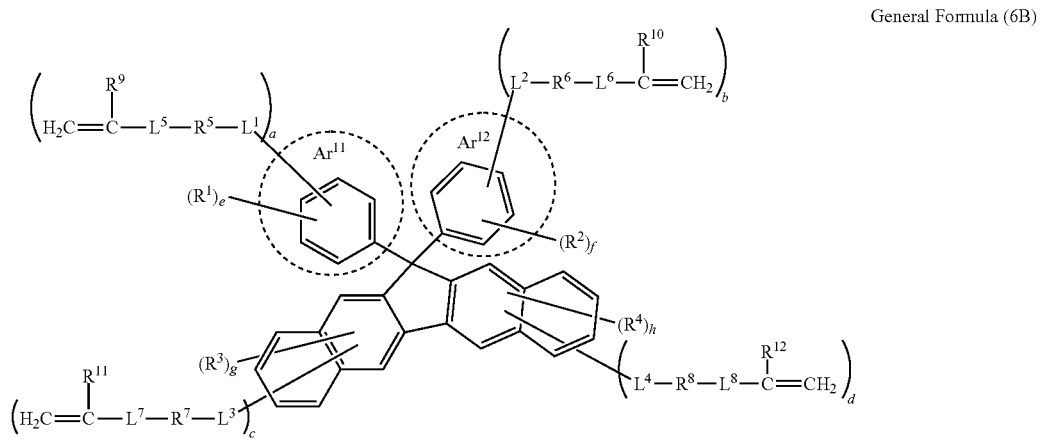

-continued

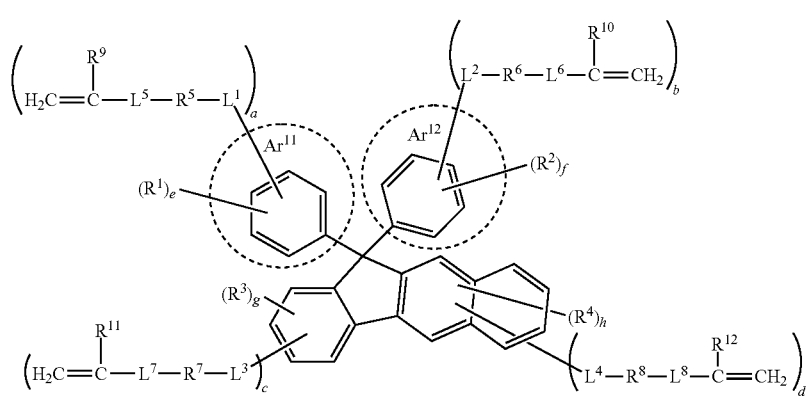

General Formula (7B)

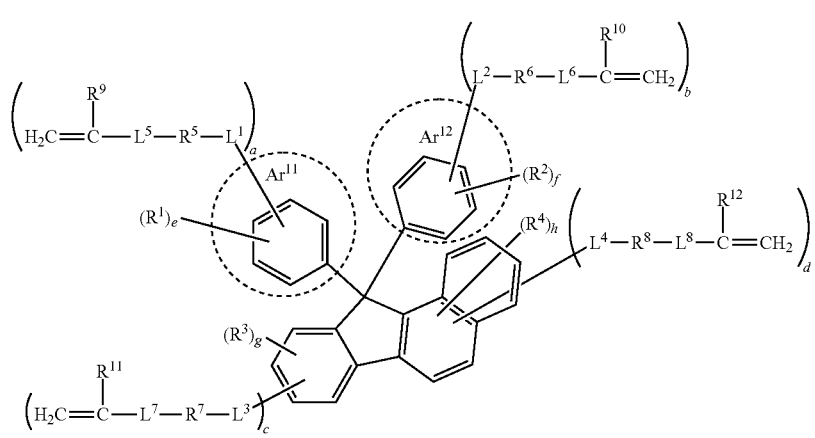

General Formula (8B)

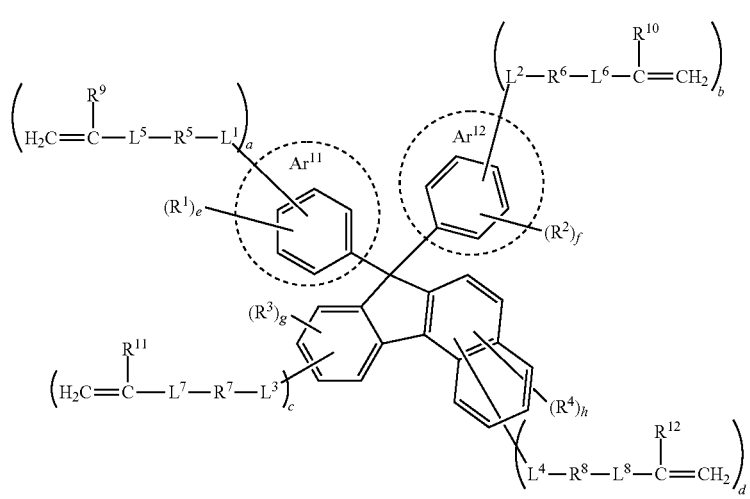

General Formula (9B)

wherein in the general formulae (6B), (7B), (8B) and (9B), $Ar^{11}$ and $Ar^{12}$ each independently represent an aryl or heteroaryl group containing the benzene ring surrounded by the broken line, and at least one of $Ar^{11}$ and $Ar^{12}$ is an aromatic condensed ring group containing the benzene ring surrounded by the broken line as one condensed ring therein, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, e, f, g and h each independently indicate an integer of 0 or more, provided that in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

4. The curable resin composition according to claim 1, wherein the condensed ring-containing compound represented by the general formula (5) is any of the following Xa-4 to Xa-15:
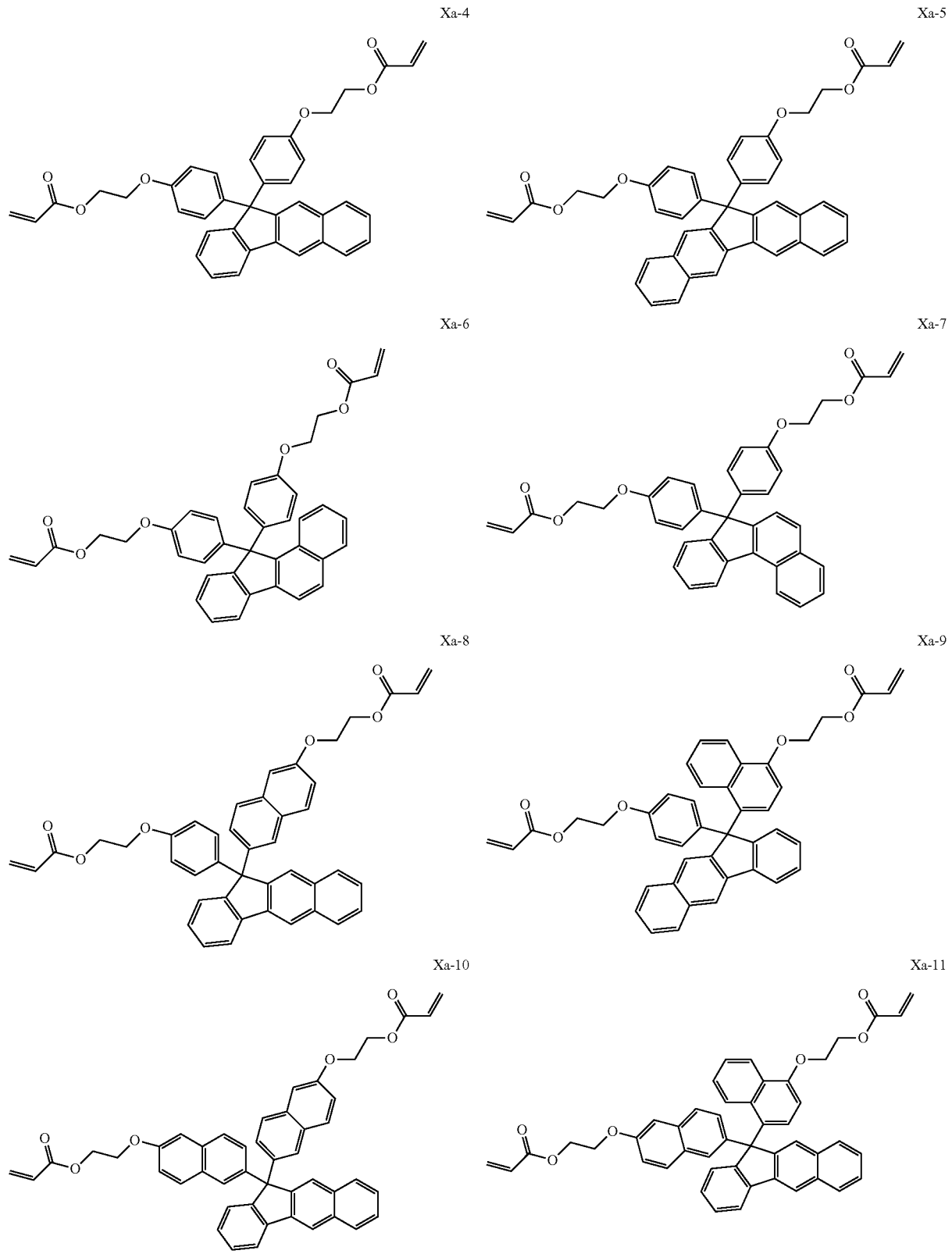

-continued

Xa-12
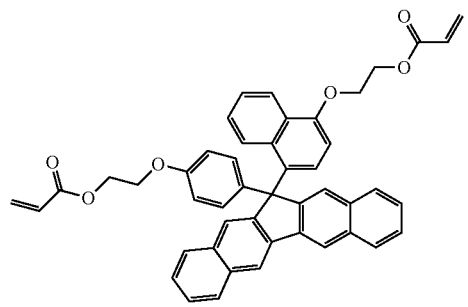

Xa-13
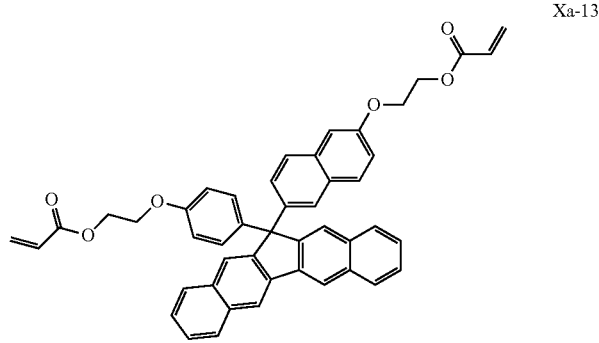

Xa-14
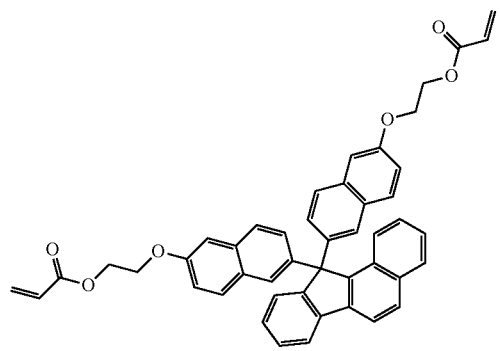

Xa-15
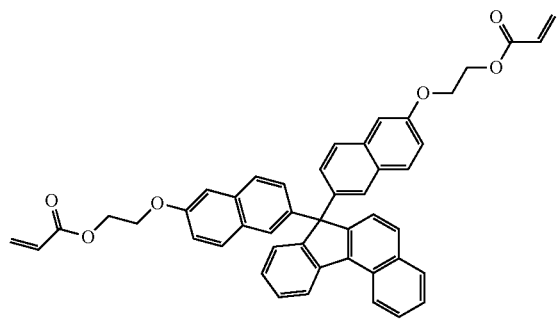

5. The curable resin composition according to claim 1, containing the non-conjugated vinylidene group-containing compound represented by the general formula (2) in an amount of from 2 to 50% by mass relative to the condensed ring-containing compound represented by the general formula (5).

6. The curable resin composition according to claim 1, containing a thermal-radical polymerization initiator and a photoradical polymerization initiator.

7. The curable resin composition according to claim 1, further containing a monofunctional (meth)acrylate monomer, in which the content of the monofunctional (meth)acrylate monomer is from 10 to 80% by mass relative to the condensed ring-containing compound represented by the general formula (5).

8. A compound represented by the following general formula (5):

General Formula (5)

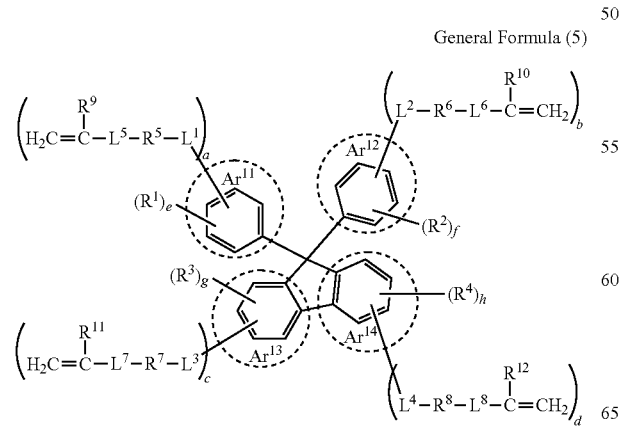

wherein in the general formula (5), $Ar^{11}$ and $Ar^{12}$ each independently represent an aryl or heteroaryl group containing the benzene ring surrounded by the broken line, $Ar^{13}$ and $Ar^{14}$ each independently represent an aryl or heteroaryl group containing the benzene ring surrounded by the broken line, and at least one of $Ar^{13}$ and $Ar^{14}$ is an aromatic condensed ring group containing the benzene ring surrounded by the broken line as one condensed ring therein, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, e, f, g and h each independently indicate an integer of 0 or more, the upper limit of e and f each is 5-a and 5-b, respectively, the upper limit of g and h each is a value calculated by subtracting c or d from the possible maximum number of the substituents that $Ar^{13}$ and $Ar^{14}$ each may have, provided that in a case where $Ar^{13}$ and $Ar^{14}$ each are an aromatic condensed ring group containing the benzene ring surrounded by the broken line as one condensed ring therein, the structures surrounded by c's or d's parentheses as well as $R^3$ and $R^4$ each may independently substitute on the benzene ring surrounded by the broken line or on any other ring than the benzene ring surrounded by the broken line.

9. The compound according to claim 8, wherein in the general formula (5), $Ar^{13}$ and $Ar^{14}$ each are independently an aromatic hydrocarbon group having from 6 to 10 carbon atoms and containing the benzene ring surrounded by the broken line.

10. The compound according to claim 8, wherein the compound represented by the general formula (5) is represented by any of the following general formulae (6) to (9):

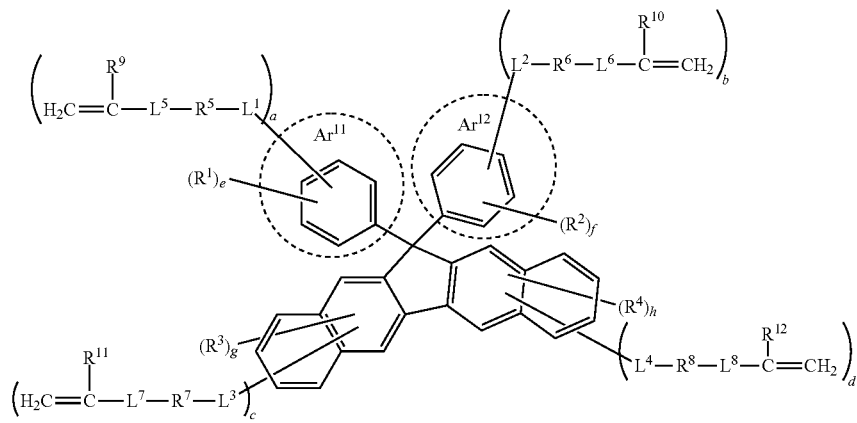

General Formula (6)

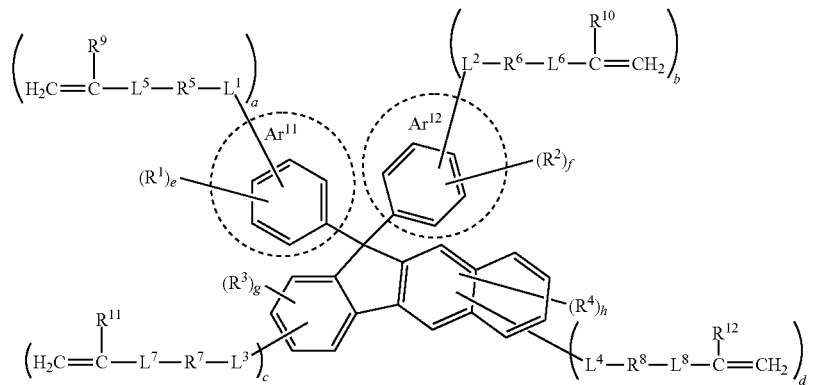

General Formula (7)

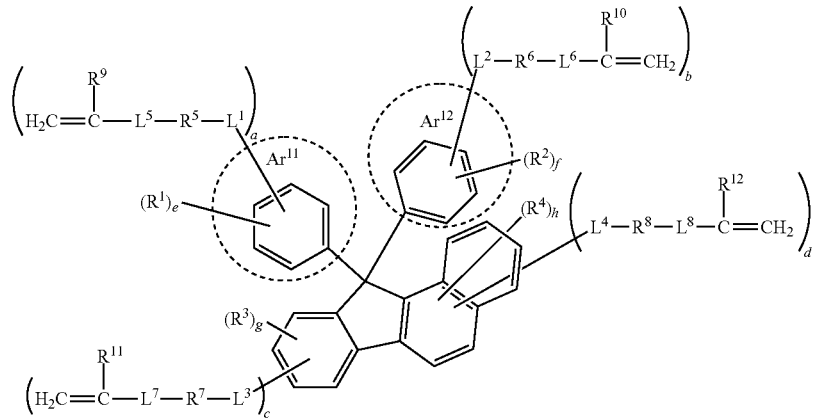

General Formula (8)

-continued

General Formula (9)

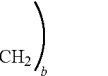
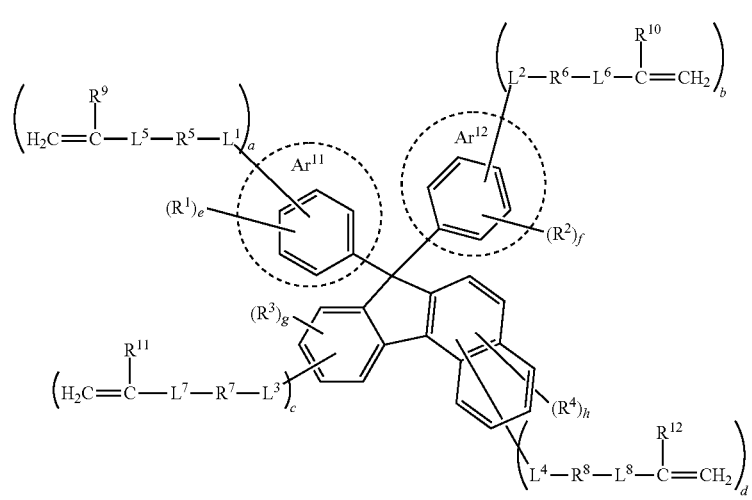

wherein in the general formulae (6) to (9), $Ar^{11}$ and $Ar^{12}$ each independently represent an aryl or heteroaryl group containing the benzene ring surrounded by the broken line, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, e, f, g and h each independently indicate an integer of 0 or more, provided that in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

11. The compound according to claim 10, wherein the compound represented by the general formulae (6) to (9) is represented by any of the following formulae (6A), (7A), (8A), (9A), (6B), (7B), (8B) and (9B):

General Formula (6A)

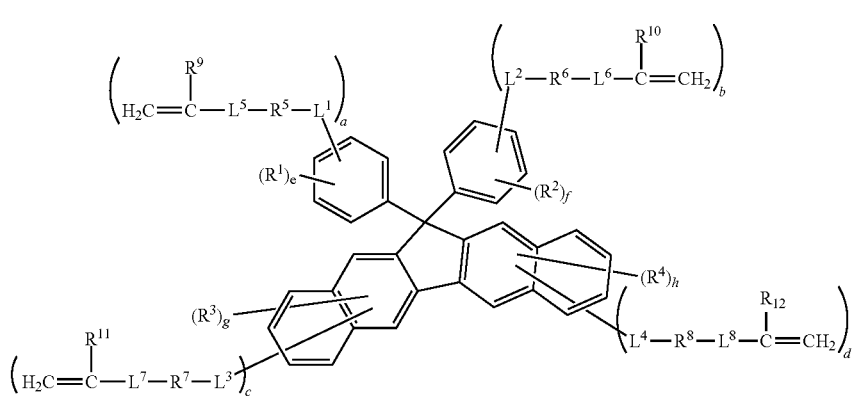

General Formula (7A)

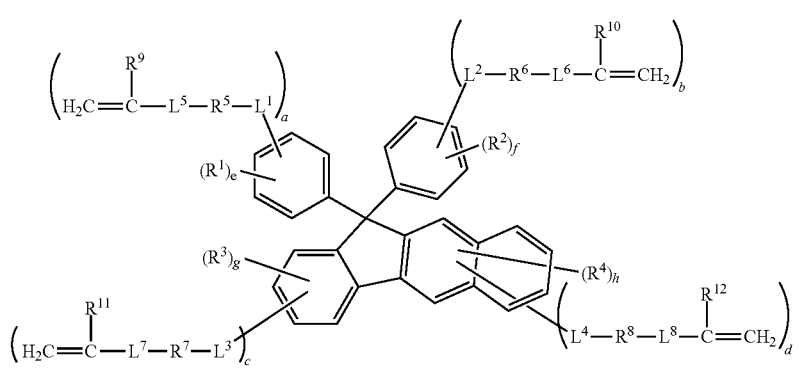

General Formula (8A)

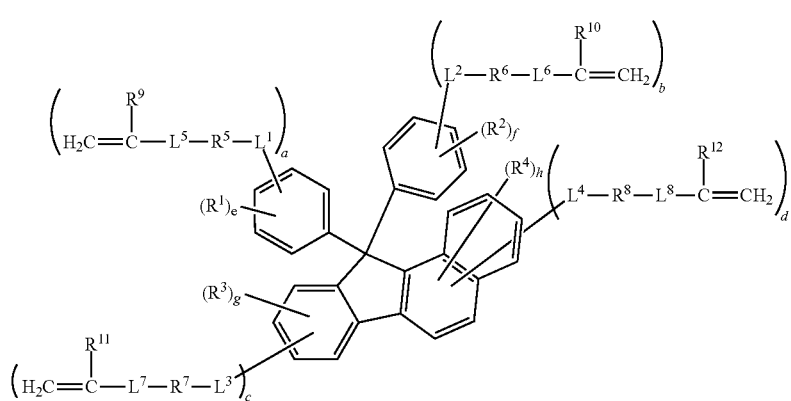

General Formula (9A)

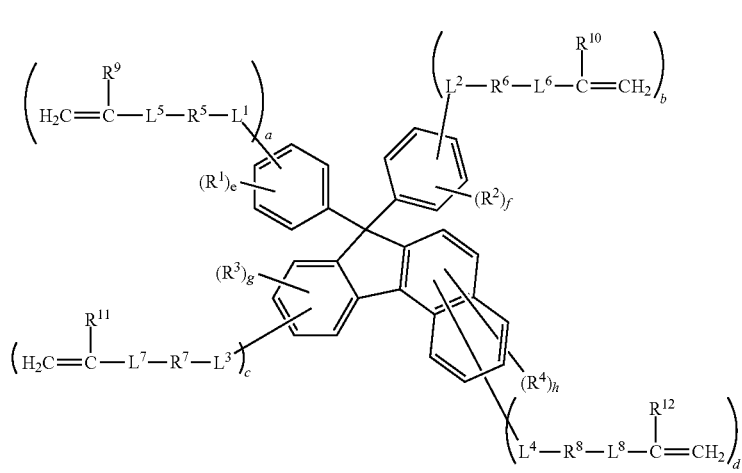

wherein in the general formulae (6A), (7A), (8A) and (9A), $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, and e, f, g and h each independently indicate an integer of 0 or more;

General Formula (6B)

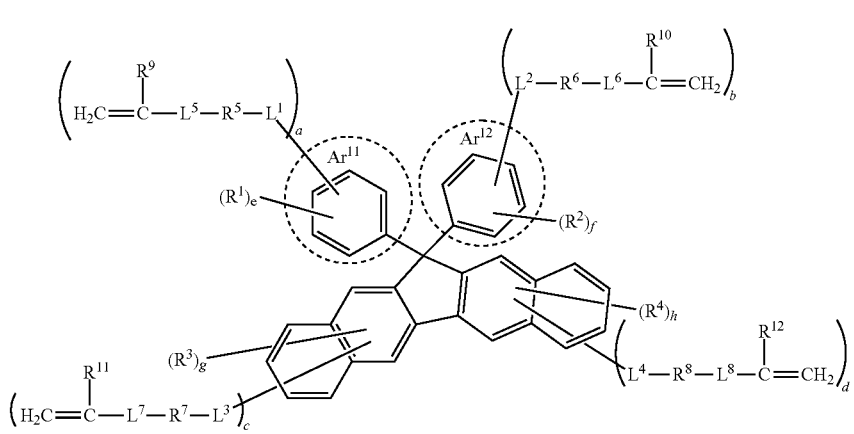

General Formula (7B)

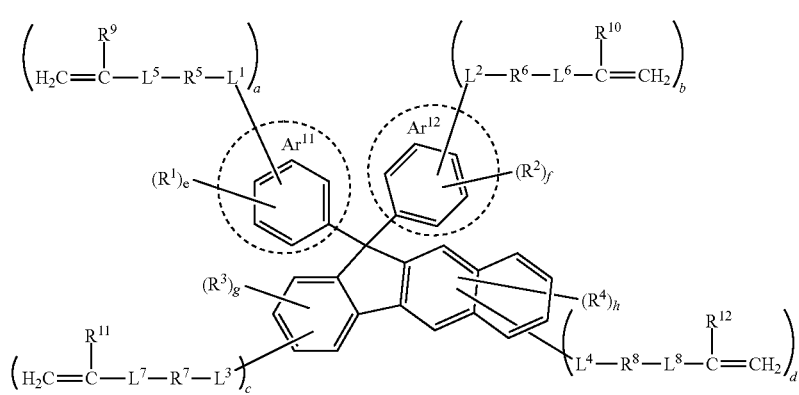

General Formula (8B)

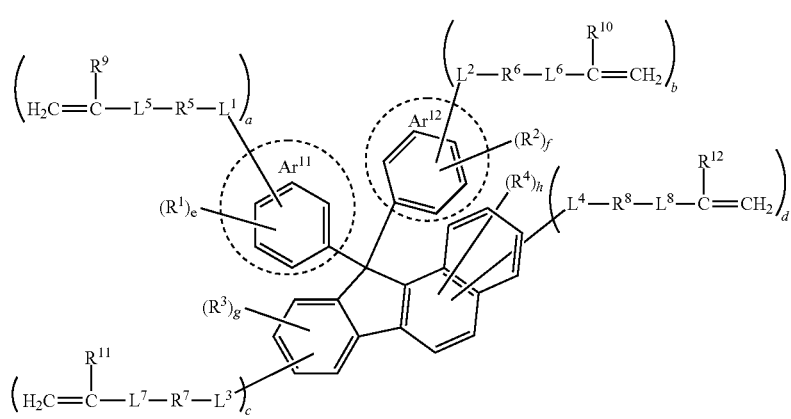

General Formula (9B)

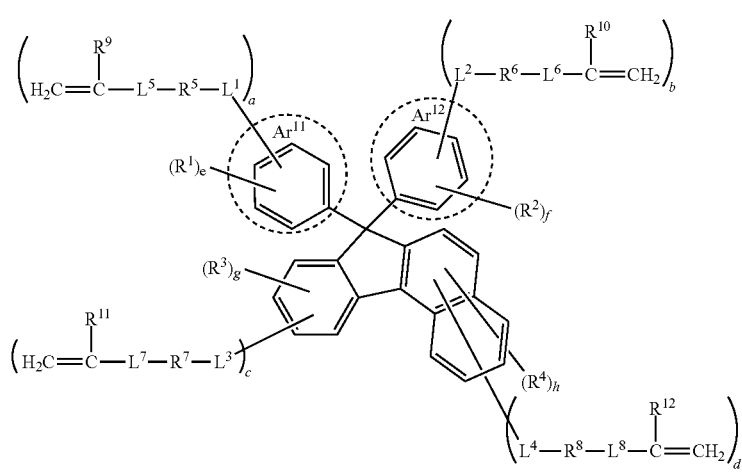

wherein in the general formulae (6B), (7B), (8B) and (9B), $Ar^{11}$ and $Ar^{12}$ each independently represent an aryl or heteroaryl group containing the benzene ring surrounded by the broken line, and at least one of $Ar^{11}$ and $Ar^{12}$ is an aromatic condensed ring group containing the benzene ring surrounded by the broken line as one condensed ring therein, $L^1$ to $L^4$ each independently represent a single bond, an oxygen atom or a sulfur atom, $R^5$ to $R^8$ each independently represent a single bond or an alkylene group optionally having a substituent, $L^5$ to $L^8$ each independently represent a single bond, an ester bond, a thioester bond or an amide bond, and $R^9$ to $R^{12}$ each independently represent a hydrogen atom or a methyl group, a and b each independently indicate an integer of from 1 to 5, and c and d each independently indicate an integer of from 0 to 5, $R^1$ to $R^4$ each independently represent a substituent, e, f, g and h each independently indicate an integer of 0 or more, provided that in a case where $Ar^{11}$ and $Ar^{12}$ each are an aromatic condensed ring group containing the benzene ring surrounded by the broken line as one condensed ring therein, the structures surrounded by a's or b's parentheses as well as $R^1$ and $R^2$ each may independently substitute on the benzene ring surrounded by the broken line or on any other ring than the benzene ring surrounded by the broken line.

12. The compound according to claim 8, wherein in the general formula (5), $L^1$ to $L^4$ each are independently an oxygen atom or a sulfur atom, $L^5$ to $L^8$ each are independently an ester bond, a thioester bond or an amide bond, and $R^5$ to $R^8$ each are independently an alkylene group optionally having a substituent.

13. The compound according to claim 8, wherein in any of the general formula (5), c and d are both 0.

14. The compound according to claim 8, wherein the compound represented by the general formula (5) is any of the following Xa-4 to Xa-15:

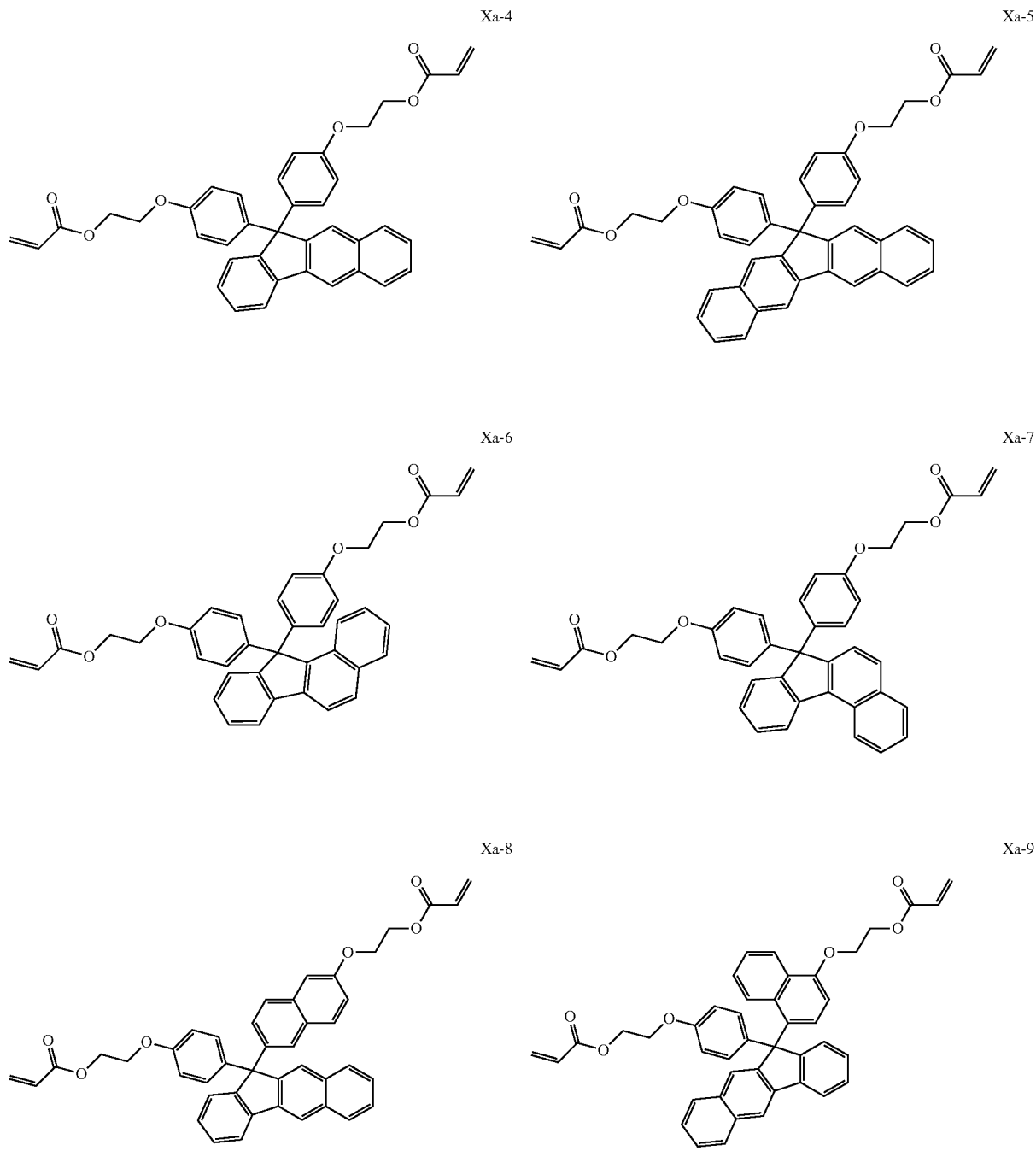

-continued
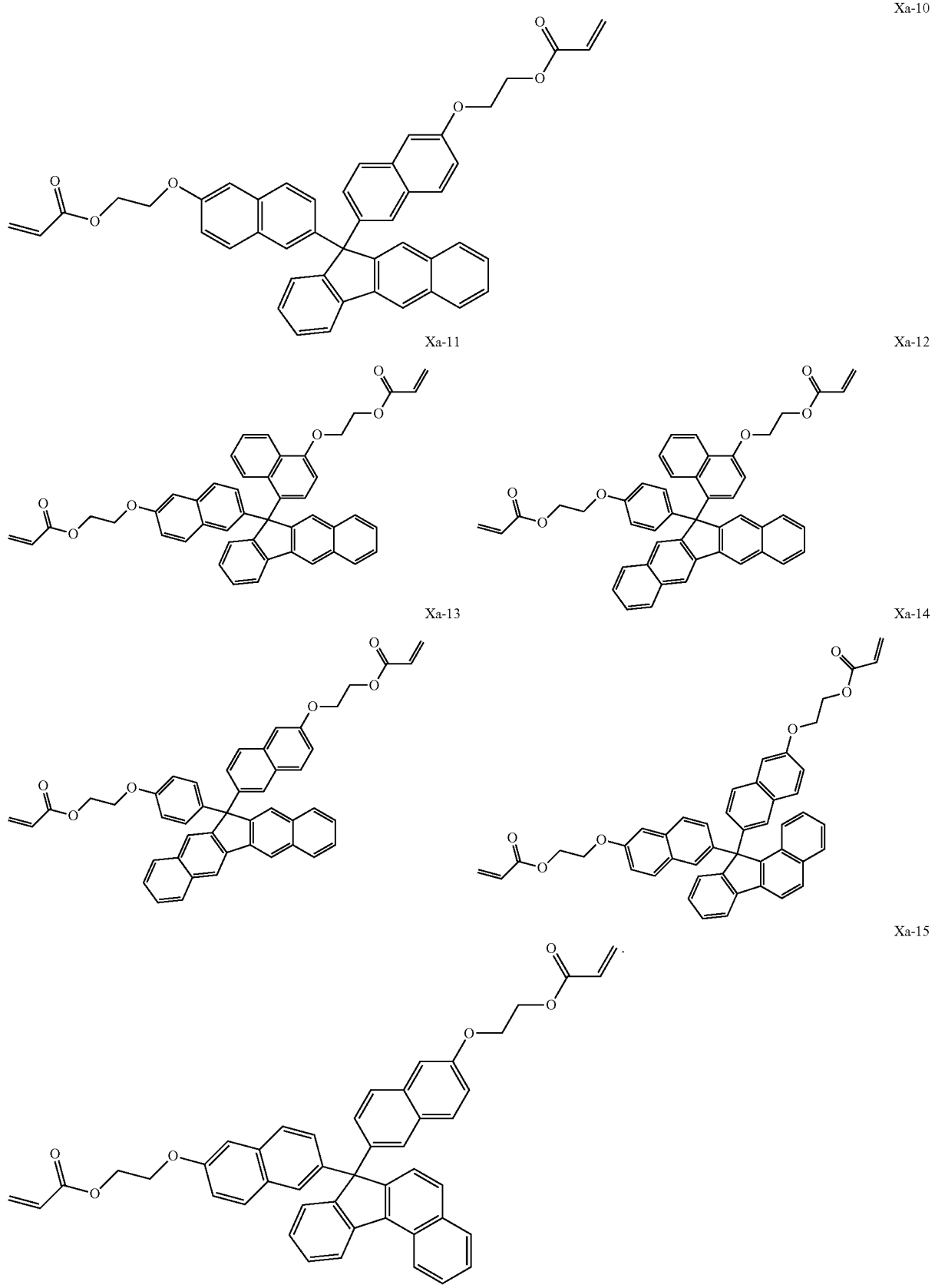
* * * * *